(12) United States Patent
Merrill et al.

(10) Patent No.: US 8,138,173 B2
(45) Date of Patent: Mar. 20, 2012

(54) PYRAZOLO[3,4-C]QUINOLINES, PYRAZOLO[3,4-C]NAPHTHYRIDINES, ANALOGS THEREOF, AND METHODS

(75) Inventors: Bryon A. Merrill, River Falls, WI (US); Michael E. Danielson, Saint Paul, MN (US); David S. Hays, Woodbury, MN (US); David T. Amos, Saint Paul, MN (US); Philip D. Heppner, Forest Lake, MN (US); Tushar A. Kshirsagar, Woodbury, MN (US); Gregory D. Lundquist, Jr., Eagan, MN (US); William H. Moser, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 856 days.

(21) Appl. No.: 11/887,526

(22) PCT Filed: Mar. 31, 2006

(86) PCT No.: PCT/US2006/012031
§ 371 (c)(1),
(2), (4) Date: Sep. 15, 2008

(87) PCT Pub. No.: WO2006/107771
PCT Pub. Date: Oct. 12, 2006

(65) Prior Publication Data
US 2009/0069299 A1    Mar. 12, 2009

Related U.S. Application Data

(60) Provisional application No. 60/667,879, filed on Apr. 1, 2005.

(51) Int. Cl.
*A61K 31/55* (2006.01)
*A61K 31/437* (2006.01)
*C07D 471/04* (2006.01)

(52) U.S. Cl. .................. 514/217.07; 514/303; 514/293; 546/119; 546/82; 540/597

(58) Field of Classification Search ........................ None
See application file for complete search history.

(56) References Cited

U.S. PATENT DOCUMENTS
7,544,697 B2    6/2009   Hayes et al.

OTHER PUBLICATIONS

STN_11887526_preliminary_(2011).*
Kunal Roy, QSAR & Combinatorial Science, (2003), vol. 22, p. 614-621.*
Mataka et al., Condensation reaction of 3,4-Dibenzoyl-l-methyl-2,5-diphenylpyrrole and -1-phenylpyrazole with methylamine derivatives affording pyrrolo [3,4-c] pyridine and 2H-pyrazolo[3,4-c]- and [4,3-c]pyridines. Journal of Heterocyclic Chemistry. 1981;18(6):1073-5.
Colatta, et al., "Synthesis and Structure—Activity Relationships of a New Set of 2-Arylpyrazolo[3,4-*c*]quinoline Derivatives as Adenosine Receptor Antagonists", J Med Chem 43, pp. 3118-3124 (2000).
Nagarajan, et al., "Condensed Heterotricycles: Synthesis of pyrazolo[3,4-*c*]quinoline derivatives", Indian journal of Chemistry 31B, pp. 316-321 (1992).
Cajipe, et al., "Reaction of Aminoquinones and Related Vinylogous Amides with Nitrous Acid, Synthesis and Chemistry of Cyclic Diazo Ketones", JOC, 40 pp. 3874-3878 (1975).
Catarzi, et al., "Tricyclic Heteroaromatic Systems, Pyrazolo[3,4-*c*]quinoline-4-ones and Pyrazolo[3,4-*c*]quinoline-1,4-diones: Synthesis and Benzodiazepine Receptor Activity", Arch Pharm Pharm Med Chem 330, pp. 383-386 (1997).
Cusmano, et al, "Synthesis of 2H-Pyrazolo[3,4-*c*]quinoline Derivatives by One pot Rearrangement of Phenylhydrazones of 3-Acylindoles", Heterocycles 24 pp. 3181-3186 (1986).

* cited by examiner

*Primary Examiner* — Young Chu

(57) ABSTRACT

Pyrazolo[3,4-c]quinolines, pyrazolo[4,5-c]naphthyridines, and analogs thereof, eg., 6,7,8,9-tetrahydro pyrazolo[3,4-c] quinolines, and, pharmaceutical compositions containing the compounds, intermediates, methods of making these compounds, and methods of use of these compounds as immunomodulators, for inhibiting cytokine biosynthesis in animals and in the therapeutic or prophylactic treatment of diseases by inhibiting cytokine biosynthesis are disclosed.

18 Claims, No Drawings

PYRAZOLO[3,4-C]QUINOLINES, PYRAZOLO[3,4-C]NAPHTHYRIDINES, ANALOGS THEREOF, AND METHODS

CROSS REFERENCE TO RELATED APPLICATIONS

This application is a national stage filing under 35 U.S.C. §371 of PCT International application PCT/US2006/012031 designating the United States of America, and filed Mar. 31, 2006. This application claims the benefit under 35 U.S.C. §119(e) of U.S. Provisional Application Ser. No. 60/667,879, filed Apr. 1, 2005, which is incorporated herein by reference.

BACKGROUND

Certain compounds have been found to be useful as immune response modifiers (IRMs), rendering them useful in the treatment of a variety of disorders. However, there continues to be interest in and a need for compounds that have the ability to modulate the immune response, by induction or inhibition of cytokine biosynthesis or other means.

SUMMARY OF THE INVENTION

A new class of compounds useful for modulating cytokine biosynthesis has now been found. In one aspect, the present invention provides such compounds, which are of the Formulas I and Ia:

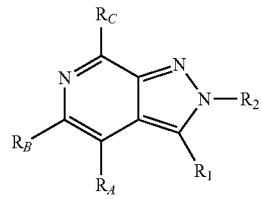

I

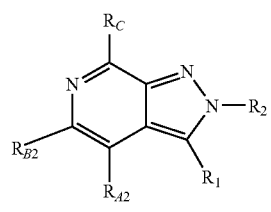

Ia and more specifically the following compounds of the Formulas II, III, IV, V, VI, VII, and VIII:

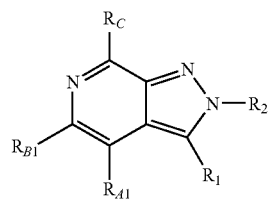

II

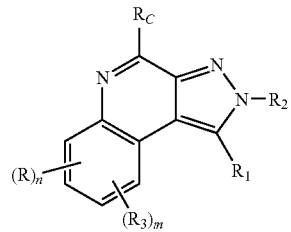

III

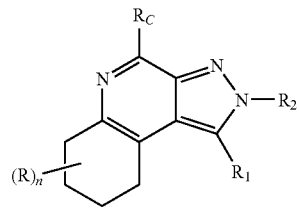

IV

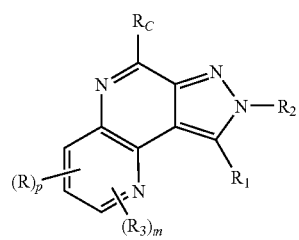

V

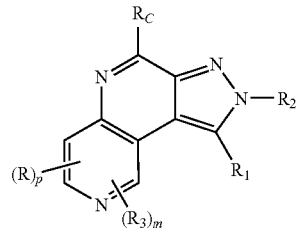

VI

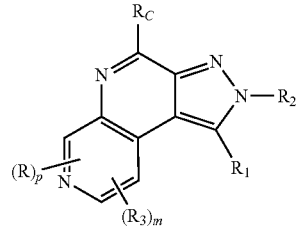

VII

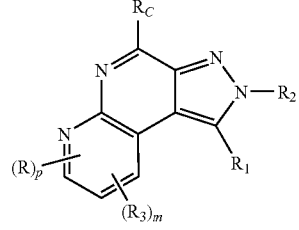

VIII wherein $R_A$, $R_B$, $R_C$, $R_{A1}$, $R_{B1}$, $R_{A2}$, $R_{B2}$, $R_1$, $R_2$, $R_3$, R, n, m, and p are as defined below; and pharmaceutically acceptable salts thereof.

The compounds of Formulas I, Ia, II, III, IV, V, VI, VII, and VIII are useful as immune response modifiers (IRMS) due to their ability to modulate cytokine biosynthesis (e.g., inhibit the biosynthesis or production of one or more cytokines) and otherwise modulate the immune response when administered to animals. The ability to modulate cytokine biosynthesis, for example, inhibit the biosynthesis of tumor necrosis factor (α) (TNF-α) or interleukin-1 (IL-1), makes the compounds useful for preventing or treating various conditions that are responsive to such changes in the immune response, for example, autoimmune diseases.

In another aspect, the present invention provides pharmaceutical compositions that contain the immune response modifier compounds, and methods of modulating (e.g., inhibiting) cytokine biosynthesis in an animal, prophylactic treatment of a disease by inhibiting cytokine biosynthesis, and therapeutic treatment of a disease by inhibiting cytokine biosynthesis in an animal, by administering an effective amount of one or more compounds of the Formulas I, Ia, II, III, IV, V, VI, VII, and/or VIII, and/or pharmaceutically acceptable salts thereof to the animal.

In another aspect, the invention provides methods of synthesizing compounds of the Formulas I, Ia, II, III, IV, V, VI, VII, and VIII and intermediates useful in the synthesis of these compounds.

As used herein, "a," "an," "the," "at least one," and "one or more" are used interchangeably.

The terms "comprising" and variations thereof do not have a limiting meaning where these terms appear in the description and claims.

The above summary of the present invention is not intended to describe each disclosed embodiment or every implementation of the present invention. The description that follows more particularly exemplifies illustrative embodiments. Guidance is also provided herein through lists of examples, which can be used in various combinations. In each instance, the recited list serves only as a representative group and should not be interpreted as an exclusive list.

DETAILED DESCRIPTION OF ILLUSTRATIVE EMBODIMENTS OF THE INVENTION

In one aspect, the present invention provides compounds of the Formula I:

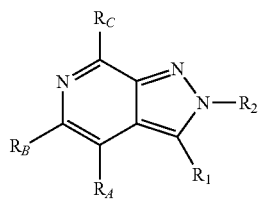

I wherein:

when taken together, $R_A$ and $R_B$ form a fused aryl ring or heteroaryl ring containing one heteroatom selected from the group consisting of N and S, wherein the aryl or heteroaryl ring is unsubstituted or substituted by one or more R' groups;

or when taken together, $R_A$ and $R_B$ form a fused 5 to 7 membered saturated ring, optionally containing one heteroatom selected from the group consisting of N and S, and unsubstituted or substituted by one or more R groups;

$R_C$ is selected from the group consisting of hydrogen, alkyl, alkoxy, phenyl, phenoxy, heteroaryl, heteroaryloxy, halogen, haloalkyl, hydroxy, cyano, mercapto, nitro, carboxy, alkylamino, dialkylamino, benzylamino, heteroarylmethylamino, and cyclic amino; wherein phenyl, phenoxy, heteroaryl, heteroaryloxy, the phenyl ring of the benzyl group, and heteroaryl in the heteroarylmethylamino group are unsubstituted or substituted by one or more substituents independently selected from the group consisting of methyl, methoxy, bromo, chloro, fluoro, trifluoromethyl, trifluoromethoxy, cyano, nitro, and hydroxy;

R' is a non-interfering substituent;

R is selected from the group consisting of halogen, hydroxy, alkyl, alkenyl, haloalkyl, alkoxy, alkylthio, and —$N(R_9)_2$;

$R_1$ is selected from the group consisting of:
—$R_4$,
—X—$R_4$,
—X—Y—$R_4$,
—X—Y—X—Y—$R_4$, and
—X—$R_5$;

$R_2$ is selected from the group consisting of hydrogen, halogen, hydroxy, —$N(R_9)$, nitro, alkyl, aryl, and heteroaryl wherein the alkyl, aryl, or heteroaryl group is unsubstituted or substituted by one or more substituents independently selected from the group consisting of alkyl, alkoxy, alkylthio, aryl, halogen, haloalkyl, haloalkoxy, cyano, nitro, amino, hydroxy, hydroxyalkyl, hydroxyalkoxy, acetyloxy, and alkoxycarbonylalkoxy;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:

—O—, —$S(O)_{0-2}$—, —$S(O)_2$—$N(R_8)$—,
—$C(R_6)$—, —$C(R_6)$—O—, —O—$C(R_6)$—,
—O—C(O)—O—, —$N(R_8)$—Q—,
—$C(R_6)$—$N(R_8)$—, —O—$C(R_6)$—$N(R_8)$—,
—$C(R_6)$—$N(OR_9)$—, —O—$N(R_8)$—Q—,
—O—N═$C(R_4)$—, —C(═N—O—$R_8$)—,
—C(═N—O—$R_8$)—NH—,
—CH(—N(—O—$R_8$)—Q—$R_4$)—,

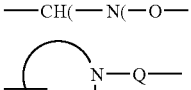
,
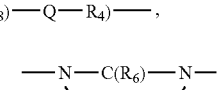
,
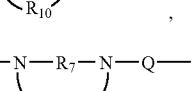
,
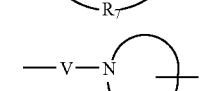
, and
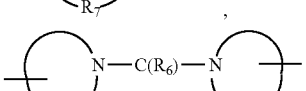
;

$R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo, and in the case of heterocyclyl, amidino and oximido;

$R_5$ is selected from the group consisting of:

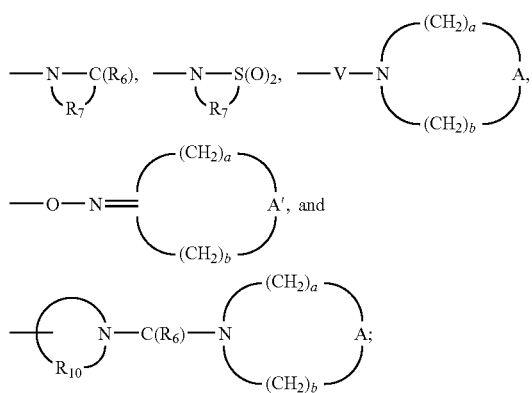

$R_6$ is selected from the group consisting of =O and =S;
$R_7$ is $C_{2-7}$ alkylene;
$R_8$ is selected from the group consisting of hydrogen, alkyl, alkoxyalkylenyl, hydroxyalkylenyl, arylalkylenyl, and heteroarylalkylenyl;
$R_9$ is selected from the group consisting of hydrogen and alkyl;
$R_{10}$ is $C_{3-8}$ alkylene;
A is selected from the group consisting of —O—, —C(O)—, —S(O)$_{0-2}$—, and —N(R$_4$)—;
A' is selected from the group consisting of —O—, —S(O)$_{0-2}$—, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_6$)—O—, —C(R$_6$)—S—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7;
with the proviso that $R_1$ is other than hydrogen, methyl, or phenyl; and with the further proviso that the compound is other than N-[1,1-dimethyl-2-(2-methyl-2H-pyrazolo[3,4-c]quinolin-1-yl)ethyl]benzamide;
or a pharmaceutically acceptable salt thereof.

In one embodiment, the present invention provides compounds of the Formula II:

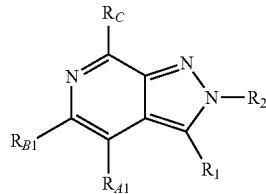

wherein:
when taken together, $R_{A1}$ and $R_{B1}$ form a fused aryl ring or heteroaryl ring containing one heteroatom selected from the group consisting of N and S, wherein the aryl or heteroaryl ring is unsubstituted or substituted by one or more R groups, or substituted by one $R_3$ group, or substituted by one $R_3$ group and one R group;
or when taken together, $R_{A1}$ and $R_{B1}$ form a fused 5 to 7 membered saturated ring, optionally containing one heteroatom selected from the group consisting of N and S, and unsubstituted or substituted by one or more R groups;
$R_C$, R, $R_1$, and $R_2$ are as defined in Formula I;
$R_3$ is selected from the group consisting of:
—Z—R$_4$,
—Z—X—R$_4$,
—Z—X—Y—R$_4$,
—Z—X—Y—X—Y—R$_4$, and
—Z—X—R$_5$;
X, Y, $R_4$, and $R_5$ are as defined in Formula I; and
Z is a bond or —O—;
with the proviso that $R_1$ is other than hydrogen, methyl, or phenyl; and with the further proviso that the compound is other than N-[1,1-dimethyl-2-(2-methyl-2H-pyrazolo[3,4-c]quinolin-1-yl)ethyl]benzamide;
or a pharmaceutically acceptable salt thereof.

In another embodiment, the present invention provides compounds of the Formula III:

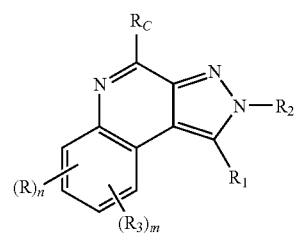

wherein:
$R_C$, $R_1$, $R_2$, R, and $R_3$ are as defined in Formula II;
n is an integer from 0 to 4;
m is 0 or 1, with the proviso that when m is 1 then n is 0 or 1;
with the proviso that $R_1$ is other than hydrogen, methyl, or phenyl; and with the further proviso that the compound is other than N-[1,1-dimethyl-2-(2-methyl-2H-pyrazolo[3,4-c]quinolin-1-yl)ethyl]benzamide;
or a pharmaceutically acceptable salt thereof.

In another embodiment, the present invention provides compounds of the Formula IV:

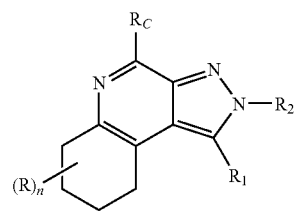

wherein:
$R_C$, $R_1$, $R_2$, and R are as defined in Formula I;
n is an integer from 0 to 4;
with the proviso that $R_1$ is other than hydrogen, methyl, or phenyl;
or a pharmaceutically acceptable salt thereof.

In other embodiments, the present invention provides compounds of the Formulas V, VI, VII, and VIII:

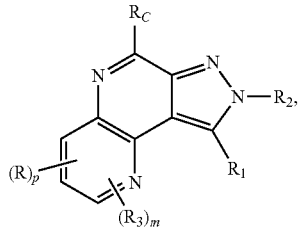
V

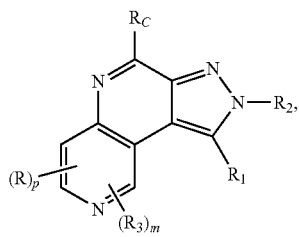
VI

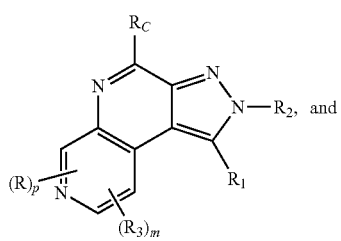
VII

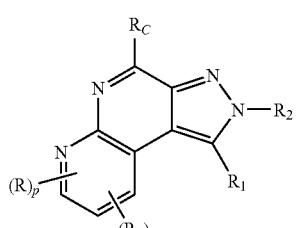
VIII wherein:

$R_C$, $R_1$, $R_2$, R, and $R_3$ are as defined in Formula II;

is an integer from 0 to 3;

m is 0 or 1, with the proviso that when m is 1 then p is 0 or 1;

with the proviso that $R_1$ is other than hydrogen;

or a pharmaceutically acceptable salt thereof.

In other embodiments, the present invention provides compounds of the Formulas IX, X, XI, and XII:

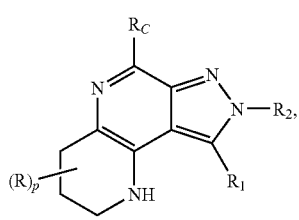
IX

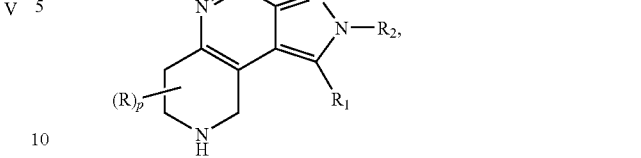
X

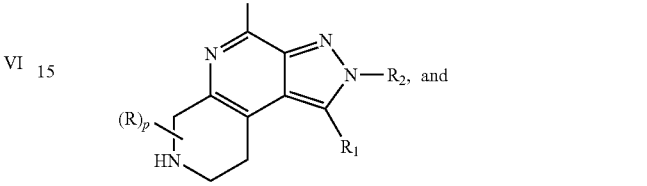
XI

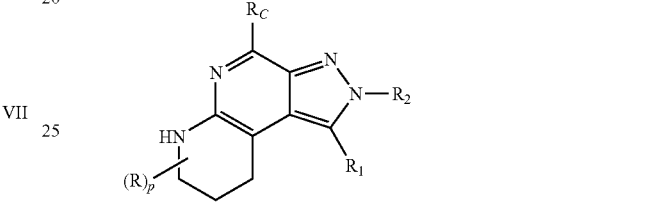
XII wherein:

$R_C$, $R_1$, $R_2$, and R are as defined in Formula I; and p is an integer from 0 to 3;

with the proviso that $R_1$ is other than hydrogen;

or a pharmaceutically acceptable salt thereof.

In another embodiment, the present invention provides a method of inhibiting cytokine biosynthesis comprising administering an effective amount of a compound of the Formula Ia:

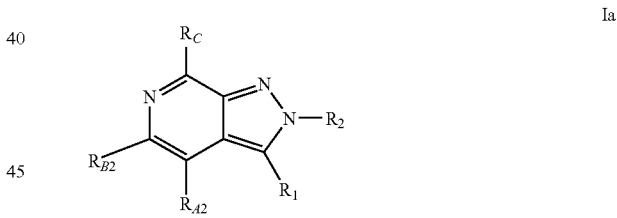
Ia wherein:

$R_{A2}$ and $R_{B2}$ are each independently selected from the group consisting of:
hydrogen,
halogen,
alkyl,
alkenyl,
alkoxy,
alkylthio, and
—N($R_9$)$_2$;

or when taken together, $R_{A2}$ and $R_{B2}$ form a fused aryl ring or heteroaryl ring containing one heteroatom selected from the group consisting of N and S, wherein the aryl or heteroaryl ring is unsubstituted or substituted by one or more R' groups;

or when taken together, $R_{A2}$ and $R_{B2}$ form a fused 5 to 7 membered saturated ring, optionally containing one heteroatom selected from the group consisting of N and S, and unsubstituted or substituted by one or more R groups; and $R_C$, R, R', $R_1$, and $R_2$ are as defined in Formula I;

or a pharmaceutically acceptable salt thereof to an animal.

Herein, "non-interfering" means that the ability of the compound or salt, which contains a non-interfering substituent, to modulate (e.g., inhibit) the biosynthesis of one or more cytokines is not destroyed by the non-interfering substitutent. Illustrative non-interfering R' groups include those described herein for R and $R_3$.

As used herein, the terms "alkyl", "alkenyl", "alkynyl" and the prefix "alk-" are inclusive of both straight chain and branched chain groups and of cyclic groups, e.g., cycloalkyl and cycloalkenyl. Unless otherwise specified, these groups contain from 1 to 20 carbon atoms, with alkenyl groups containing from 2 to 20 carbon atoms, and alkynyl groups containing from 2 to 20 carbon atoms. In some embodiments, these groups have a total of up to 10 carbon atoms, up to 8 carbon atoms, up to 6 carbon atoms, or up to 4 carbon atoms. Cyclic groups can be monocyclic or polycyclic and preferably have from 3 to 10 ring carbon atoms. Exemplary cyclic groups include cyclopropyl, cyclopropylmethyl, cyclopentyl, cyclohexyl, adamantyl, and substituted and unsubstituted bornyl, norbornyl, and norbornenyl.

Unless otherwise specified, "alkylene", "alkenylene", and "alkynylene" are the divalent forms of the "alkyl", "alkenyl", and "alkynyl" groups defined above. The terms, "alkylenyl", "alkenylenyl", and "alkynylenyl" are used when "alkylene", "alkenylene", and "alkynylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like.

The term "aryl" as used herein includes carbocyclic aromatic rings or ring systems. Examples of aryl groups include phenyl, naphthyl, biphenyl, fluorenyl and indenyl.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2-12 carbon atoms, 1-3 rings, 1-4 heteroatoms, and O, S, and N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

The term "heterocyclyl" includes non-aromatic rings or ring systems that contain at least one ring heteroatom (e.g., O, S, N) and includes all of the fully saturated and partially unsaturated derivatives of the above mentioned heteroaryl groups. In some embodiments, the term "heterocyclyl" includes a ring or ring system that contains 2-12 carbon atoms, 1-3 rings, 1-4 heteroatoms, and O, S, and N as the heteroatoms. Exemplary heterocyclyl groups include pyrrolidinyl, tetrahydrofuranyl, morpholinyl, thiomorpholinyl, 1,1-dioxothiomorpholinyl, piperidinyl, piperazinyl, thiazolidinyl, imidazolidinyl, isothiazolidinyl, tetrahydropyranyl, quinuclidinyl, homopiperidinyl (azepanyl), 1,4-oxazepanyl, homopiperazinyl (diazepanyl), 1,3-dioxolanyl, aziridinyl, azetidinyl, dihydroisoquinolin-(1H)-yl, octahydroisoquinolin-(1H)-yl, dihydroquinolin-(2H)-yl, octahydroquinolin-(2H)-yl, dihydro-1H-imidazolyl, 3-azabicyclo[3.2.2]non-3-yl, and the like.

The term "heterocyclyl" includes bicyclic and tricyclic heterocyclic ring systems. Such ring systems include fused and/or bridged rings and spiro rings. Fused rings can include, in addition to a saturated or partially saturated ring, an aromatic ring, for example, a benzene ring. Spiro rings include two rings joined by one spiro atom and three rings joined by two spiro atoms.

The term "cyclic amino" includes groups of the formula

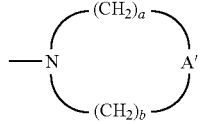

wherein a, b, and A' are as defined in Formula I above.

The terms "arylene", "heteroarylene", and "heterocyclylene" are the divalent forms of the "aryl", "heteroaryl", and "heterocyclyl" groups defined above. The terms, "arylenyl", "heteroarylenyl", and "heterocyclylenyl" are used when "arylene", "heteroarylene", and "heterocyclylene", respectively, are substituted. For example, an alkylarylenyl group comprises an arylene moiety to which an alkyl group is attached.

The term "fused aryl ring" includes fused carbocyclic aromatic rings or ring systems. Examples of fused aryl rings include benzo, naphtho, fluoreno, and indeno. In certain embodiments, the fused aryl ring is benzo.

The term "fused heteroaryl ring" includes the fused forms of 5 or 6 membered aromatic rings that contain one heteroatom selected from S and N. In certain embodiments, the fused heteroaryl ring is pyrido or thieno. In certain embodiments, the fused heteroaryl ring is pyrido. In certain of these embodiments, the pyrido ring is

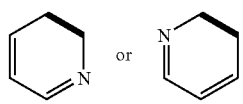

wherein the highlighted bond indicates the position where the ring is fused.

The term "fused 5 to 7 membered saturated ring" includes rings which are fully saturated except for the bond where the ring is fused. In certain embodiments, the ring is a cyclohexene ring. In certain embodiments wherein one heteroatom (N or S) is present, the ring is tetrahydropyrido or dihydrothieno. In certain embodiments, the ring is tetrahydropyrido. In certain of these embodiments, the ring is

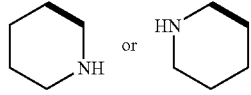

wherein the highlighted bond indicates the position where the ring is fused.

When a group (or substituent or variable) is present more than once in any formula described herein, each group (or substituent or variable) is independently selected, whether explicitly stated or not. For example, for the formula —N($R_8$)—C($R_6$)—N($R_8$)— each $R_8$ group is independently selected. In another example, when an $R_1$ and an $R_3$ group both contain an $R_4$ group, each $R_4$ group is independently selected. In a further example, when more than one Y group is present (i.e., $R_1$ and $R_3$ both contain a Y group) and each Y group contains one or more $R_8$ groups, then each Y group is independently selected, and each $R_8$ group is independently selected.

The invention is inclusive of the compounds described herein and salts thereof, in any of their pharmaceutically acceptable forms, including isomers (e.g., diastereomers and enantiomers), solvates, polymorphs, prodrugs, and the like. In particular, if a compound is optically active, the invention specifically includes each of the compound's enantiomers as well as racemic and scalemic mixtures of the enantiomers. It should be understood that the term "compound" or the term "compounds" includes any or all of such forms, whether explicitly stated or not (although at times, "salts" are explicitly stated).

The term "prodrug" means a compound that can be transformed in vivo to yield an immune response modifying compound, including any of the salt, solvated, polymorphic, or isomeric forms described above. The prodrug, itself, may be an immune response modifying compound, including any of the salt, solvated, polymorphic, or isomeric forms described above. The transformation may occur by various mechanisms, such as through a chemical (e.g., solvolysis or hydrolysis, for example, in the blood) or enzymatic biotransformation. A discussion of the use of prodrugs is provided by T. Higuchi and W. Stella, "Pro-drugs as Novel Delivery Systems," Vol. 14 of the A. C. S. Symposium Series, and in Bioreversible Carriers in Drug Design, ed. Edward B. Roche, American Pharmaceutical Association and Pergamon Press, 1987.

For example, if a compound of the present invention contains a carboxylic acid functional group, a prodrug can comprise an ester formed by the replacement of the hydrogen atom of the acid group with a group such as $C_{1-8}$ alkyl, $C_{2-12}$ alkanoyloxymethyl, 1-(alkanoyloxy)ethyl having from 4 to 9 carbon atoms, 1-methyl-1-(alkanoyloxy)ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—$C_{1-2}$ alkylamino$C_{2-3}$ alkyl (such as β-dimethylaminoethyl), carbamoyl-$C_{1-2}$ alkyl, N,N-di$C_{1-2}$ alkylcarbamoyl-$C_{1-2}$ alkyl and piperidino-, pyrrolidino-, or morpholino$C_{2-3}$ alkyl.

If a compound of the present invention contains an alcohol functional group, a prodrug can be formed by the replacement of the hydrogen atom of the alcohol group with a group such as $C_{1-6}$ alkanoyloxymethyl, 1-($C_{1-6}$ alkanoyloxy)ethyl, 1-methyl-1-($C_{1-6}$ alkanoyloxy)ethyl, $C_{1-6}$ alkoxycarbonyloxymethyl, N—($C_{1-6}$ alkoxycarbonyl)aminomethyl, succinoyl, $C_{1-6}$ alkanoyl, α-amino$C_{1-4}$ alkanoyl, arylacyl and α-aminoacyl, or α-aminoacyl-α-aminoacyl, where each α-aminoacyl group is independently selected from the naturally occurring L-amino acids, $P(O)(OH)_2$, $P(O)(O-C_{1-6}$ alkyl$)_2$ or glycosyl (the radical resulting from the removal of a hydroxyl group of the hemiacetal form of a carbohydrate).

If a compound of the present invention contains an amine functional group, a prodrug can be formed by the replacement of a hydrogen atom in the amine group with a group such as R"-carbonyl, R"-O-carbonyl, N(R")(R''')-carbonyl where R" and R''' are each independently $C_{1-10}$ alkyl, $C_{3-7}$ cycloalkyl, benzyl, or R"-carbonyl is a natural α-aminoacyl or natural α-aminoacyl-natural α-aminoacyl, —C(OH)C(O)OY' wherein Y' is H, $C_{1-6}$ alkyl or benzyl, —C(OY$_0$)Y$_1$ wherein Y$_0$ is $C_{1-4}$ alkyl and Y$_1$ is $C_{1-6}$ alkyl, carboxy$C_{1-6}$ alkyl, amino$C_{1-4}$ alkyl or mono-N— or di-N,N—$C_{1-6}$ alkylaminoalkyl, —C(Y$_2$)Y$_3$ wherein Y$_2$ is H or methyl and Y$_3$ is mon-N— or di-N,N—$C_{1-6}$ alkylamino, morpholino, piperidin-1-yl pyrrolidin-1-yl, or 4-$C_{1-4}$ alkylpiperazin-1-yl.

Compounds (including intermediates) of the present invention may exist in different tautomeric forms, and all such forms are embraced within the scope of the invention. The term "tautomer" or "tautomeric form" refers to structural isomers of different energies which are interconvertible via a low energy barrier. For example proton tautomers (prototropic tautomers) include interconversions via migration of a proton, such as keto-enol and imine-enamine isomerizations. When compounds of the present invention have a hydrogen atom at the 2-position, proton migration between the 2- and 3-positions may occur.

The compounds of the present invention may exist in unsolvated as well as solvated forms with pharmaceutically acceptable solvents such as water, ethanol, and the like. The present invention embraces both solvated and unsolvated forms.

For any of the compounds presented herein, each one of the following variables (e.g., $R_A$, $R_B$, $R_C$, R, R', $R_1$, $R_2$, $R_3$, n, m, p, A, X, Y, Z, and so on) in any of its embodiments can be combined with any one or more of the other variables in any of their embodiments and associated with any one of the formulas described herein, as would be understood by one of skill in the art. Each of the resulting combinations of variables is an embodiment of the present invention.

For certain embodiments of Formulas I or Ia, each R' is independently a non-interfering substituent.

For certain embodiments of Formula I, when taken together, $R_A$ and $R_B$ form a fused aryl ring or heteroaryl ring containing one heteroatom selected from the group consisting of N and S, wherein the aryl or heteroaryl ring is unsubstituted or substituted by one or more R' groups;

or when taken together, $R_A$ and $R_B$ form a fused 5 to 7 membered saturated ring, optionally containing one heteroatom selected from the group consisting of N and S, and unsubstituted or substituted by one or more R groups;

For certain embodiments of Formula I, $R_A$ and $R_B$ form a fused aryl or heteroaryl ring.

For certain embodiments of Formula I, $R_A$ and $R_B$ form a fused aryl ring.

For certain embodiments of Formula I, $R_A$ and $R_B$ form a fused heteroaryl ring.

For certain embodiments of Formula I, $R_A$ and $R_B$ form a fused 5 to 7 membered saturated ring.

For certain embodiments of Formula I, $R_A$ and $R_B$ form a fused 5 to 7 membered saturated ring containing one heteroatom selected from the group consisting of N and S. In certain embodiments the heteroatom is N.

For certain embodiments of Formula Ia, $R_{A2}$ and $R_{B2}$ are each independently selected from the group consisting of hydrogen, halogen, alkyl, alkenyl, alkoxy, alkylthio, and —N(R$_9$)$_2$;

or when taken together, $R_{A2}$ and $R_{B2}$ form a fused aryl ring or heteroaryl ring containing one heteroatom selected from the group consisting of N and S, wherein the aryl or heteroaryl ring is unsubstituted or substituted by one or more R' groups;

or when taken together, $R_{A2}$ and $R_{B2}$ form a fused 5 to 7 membered saturated ring, optionally containing one heteroatom selected from the group consisting of N and S, and unsubstituted or substituted by one or more R groups.

For certain embodiments of Formula Ia, $R_{A2}$ and $R_{B2}$ are each independently selected from the group consisting of hydrogen, halogen, alkyl, alkenyl, alkoxy, alkylthio, and —N(R$_9$)$_2$;

or when taken together, $R_{A2}$ and $R_{B2}$ form a fused aryl ring or heteroaryl ring containing one heteroatom selected from the group consisting of N and S, wherein the aryl or heteroaryl ring is unsubstituted or substituted by one or more R groups, or substituted by one $R_3$ group, or substituted by one $R_3$ group and one R group;

or when taken together, $R_{A2}$ and $R_{B2}$ form a fused 5 to 7 membered saturated ring, optionally containing one heteroatom selected from the group consisting of N and S, and unsubstituted or substituted by one or more R groups.

For certain embodiments of Formula Ia, $R_{A2}$ and $R_{B2}$ are each independently selected from the group consisting of hydrogen, halogen, alkyl, alkenyl, alkoxy, alkylthio, and —N(R$_9$)$_2$.

For certain embodiments of Formula Ia, $R_{A2}$ and $R_{B2}$ form a fused aryl or heteroaryl ring.

For certain embodiments of Formula Ia, $R_{A2}$ and $R_{B2}$ form a fused aryl ring.

For certain embodiments of Formula Ia, $R_{A2}$ and $R_{B2}$ form a fused heteroaryl ring.

For certain embodiments of Formula Ia, $R_{A2}$ and $R_{B2}$ form a fused 5 to 7 membered saturated ring.

For certain embodiments of Formula Ia, $R_{A2}$ and $R_{B2}$ form a fused 5 to 7 membered saturated ring containing one heteroatom selected from the group consisting of N and S. In certain embodiments the heteroatom is N.

For certain embodiments of Formula II, when taken together, $R_{A1}$ and $R_{B1}$ form a fused aryl ring or heteroaryl ring containing one heteroatom selected from the group consisting of N and S, wherein the aryl or heteroaryl ring is unsubstituted or substituted by one or more R groups, or substituted by one $R_3$ group, or substituted by one $R_3$ group and one R group; or when taken together, $R_{A1}$ and $R_{B1}$ form a fused 5 to 7 membered saturated ring, optionally containing one heteroatom selected from the group consisting of N and S, and unsubstituted or substituted by one or more R groups; wherein R is selected from the group consisting of halogen, hydroxy, alkyl, alkenyl, haloalkyl, alkoxy, alkylthio, and —N(R$_9$)$_2$; and $R_3$ is selected from the group consisting of —Z—R$_4$, —Z—X—R$_4$, —Z—X—Y—R$_4$, —Z—X—Y—X—Y—R$_4$, and —Z-X—R$_5$ For certain embodiments of Formula II, $R_{A1}$ and $R_{B1}$ form a fused aryl ring.

For certain embodiments of Formula II, $R_{A1}$ and $R_{B1}$ form a fused benzene ring which is unsubstituted.

For certain embodiments of Formula II, $R_{A1}$ and $R_{B1}$ form a fused heteroaryl ring.

For certain embodiments of Formula II, $R_{A1}$ and $R_{B1}$ form a fused pyridine ring which is unsubstituted.

For certain embodiments of Formula II, $R_{A1}$ and $R_{B1}$ form a fused 5 to 7 membered saturated ring, optionally containing one heteroatom selected from the group consisting of N and S, wherein the ring is unsubstituted.

For certain embodiments of Formula II, $R_{A1}$ and $R_{B1}$ form a fused 5 to 7 membered saturated ring.

For certain embodiments of Formula II, $R_{A1}$ and $R_{B1}$ form a fused 5 to 7 membered saturated ring containing one heteroatom selected from the group consisting of N and S. In certain embodiments the heteroatom is N.

For certain embodiments (e.g., of any one of Formulas IX through XII), R is selected from the group consisting of alkyl and haloalkyl.

For certain embodiments (e.g., of any one of the above embodiments of Formulas I, Ia, and II through VIII where R is present), R is selected from the group consisting of alkyl, alkoxy, halogen, and hydroxy.

For certain embodiments (e.g., of Formulas III or IV), n is 0.

For certain embodiments (e.g., of Formula III), m is 1 and n is 0.

For certain embodiments (e.g., of any one of Formulas V through XII), p is 0.

For certain embodiments (e.g., of any one of Formulas V through VIII), m is 1 and p is 0.

For certain embodiments (e.g., of any one of the above embodiments of Formulas III, or V through VIII where $R_3$ is present), $R_3$ is selected from the group consisting of aryl, arylalkyleneoxy, heteroarylalkyleneoxy, and heteroaryl, wherein aryl, arylalkyleneoxy, and heteroaryl are unsubstituted or substituted with one or more substituents selected from the group consisting of alkyl, alkoxy, hydroxyalkyl, and halogen.

For certain embodiments (e.g., of any one of Formulas III, or V through VIII), including the above embodiments, $R_3$ is selected from the group consisting of phenyl, 3-(hydroxymethyl)phenyl, benzyloxy, 3-furyl, pyridin-3-yl, 5-(hydroxymethyl)pyridin-3-yl, 6-chloropyridin-3-yl, 6-fluoropyridin-3-yl, 6-methylpyridin-3-yl, 3-quinolin-3-yl, thiazol-4-ylmethoxy, p-tolyl, (4-chlorobenzyl)oxy, and (4-methylbenzyl)oxy.

For certain embodiments (e.g., of any one of Formulas III, or V through VIII), including the above embodiments, $R_3$ is at the 7-position of the pyrazoloquinoline or pyrazolonaphthyridine.

For certain embodiments (e.g., of any one of Formulas III, or V through VIII), including the above embodiments, $R_3$ is selected from the group consisting of alkylsulfonylalkyleneoxy, alkylsulfonylaminoalkyleneoxy, alkylcarbonylaminoalkyleneoxy, aryl, arylalkyleneoxy, heteroaryl, heteroarylalkyleneoxy, heterocyclyl, heterocyclyloxy, heterocyclylalkyleneoxy, and heterocyclylcarbonylalkyleneoxy; wherein aryl and heteroaryl are unsubstituted or substituted by one or more substituents selected from the group consisting of alkyl, alkoxy, hydroxyalkyl, halogen, heterocyclylcarbonyl, and dialkylaminocarbonyl; and wherein heterocyclyl is unsubstituted or substituted by one or more substitutents selected from the group consisting of alkylsulfonyl, alkylcarbonyl, and oxo, except where this definition of $R_3$ is excluded.

For certain embodiments (e.g., of any one of Formulas III, or V through VIII), including the above embodiments, $R_3$ is pyridin-3-yl, pyridin-4-yl, 6-fluoropyridin-3-yl, 5-(hydroxymethyl)pyridin-3-yl, quinolin-3-yl, 2-ethoxyphenyl, or 3-(morpholine-4-carbonyl)phenyl, except where this definition is excluded.

For certain embodiments (e.g., of any one of Formulas III, or V through VIII), including the above embodiments, $R_3$ is 2-oxo-1,3-oxazolidin-3-yl, except where this definition is excluded.

For certain embodiments (e.g., of any one of Formulas III, or V through VIII), including the above embodiments, $R_3$ is 1,3-thiazol-4-ylmethoxy, (1-methyl-1H-imidazol-2-yl)methoxy, or pyridin-3-ylmethoxy, except where this definition is excluded.

For certain embodiments (e.g., of any one of Formulas III, or V through VIII), including the above embodiments, $R_3$ is 2-pyrrolidin-1-ylethoxy, 2-(2-oxopyrrolidin-1-yl)ethoxy, 2-(1,1-dioxidoisothiazolidin-2-yl)ethoxy, 2-morpholin-4-ylethoxy, 3-pyrrolidin-1-ylpropoxy, 3-(2-oxopyrrolidin-1- yl)propoxy, 3-(1,1-dioxidoisothiazolidin-2-yl)propoxy, 3-morpholin-4-ylpropoxy, 2-morpholin-4-yl-2-oxoethoxy, and

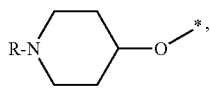

wherein R is alkylsulfonyl or alkylcarbonyl, except where this definition is excluded.

For certain embodiments (e.g., of any one of Formulas III, or V through VIII), including the above embodiments, $R_3$ is alkyl-S(O)$_2$—NH—(CH$_2$)$_{2-3}$—O—, alkyl-S(O)$_2$—(CH$_2$)$_{2-3}$—O—, or alkyl-C(O)—NH—(CH$_2$)$_{2-3}$—O—, except where this definition is excluded.

For certain embodiments (e.g., of any one of the above embodiments of Formulas III, or V through VIII where m is present), m is 0, except where this definition of m is excluded.

For certain embodiments (e.g., of any one of the above embodiments of Formulas I, Ia, and II through XII), $R_C$ is selected from the group consisting of hydroxy, halogen, alkyl, haloalkyl, phenyl, phenoxy, heteroaryl, and cyclic amino; wherein phenyl, phenoxy, and heteroaryl are unsubstituted or substituted by one or more substituents independently selected from the group consisting of methyl, methoxy, bromo, chloro, fluoro, trifluoromethyl, trifluoromethoxy, cyano, nitro, and hydroxy.

For certain embodiments (e.g., of any one of Formulas I, Ia, and II through XII), including any one of the above embodiments, $R_C$ is selected from the group consisting of hydroxy, chloro, methyl, trifluoromethyl, phenyl, phenoxy, 1-morpholino, 1-piperidino, 4-methylpiperazin-1-yl, and heteroaryl wherein heteroaryl is a 5 or 6 membered monocyclic ring containing one or two heteroatoms.

For certain embodiments (e.g., of any one of the above embodiments of Formulas I, Ia, and II through XII), $R_2$ is selected from the group consisting of hydrogen, alkyl, aryl, and heteroaryl wherein the alkyl, aryl, or heteroaryl group is unsubstituted or substituted by one or more substituents independently selected from the group consisting of alkyl, alkoxy, alkylthio, aryl, halogen, haloalkyl, haloalkoxy, cyano, nitro, amino, hydroxy, hydroxyalkyl, hydroxyalkoxy, acetyloxy, and alkoxycarbonylalkoxy.

For certain embodiments (e.g., of any one of the above embodiments of Formulas I, Ia, and II through XII), $R_2$ is selected from the group consisting of hydrogen, alkyl, aryl, and heteroaryl, wherein aryl and heteroaryl are unsubstituted or substituted by one or more substituents independently selected from the group consisting of alkyl, alkoxy, alkylthio, aryl, halogen, haloalkyl, haloalkoxy, cyano, nitro, amino, hydroxy, hydroxyalkyl, hydroxyalkoxy, acetyloxy, and alkoxycarbonylalkoxy. For certain of these embodiments, $R_2$ is $C_{1-4}$ alkyl.

For certain embodiments (e.g., of any one of Formulas I, Ia, and II through XII), including any one of the above embodiments, $R_2$ is aryl or heteroaryl, each of which is unsubstituted or substituted by one or more substituents independently selected from the group consisting of alkyl, alkoxy, alkylthio, aryl, halogen, haloalkyl, haloalkoxy, cyano, nitro, amino, hydroxy, hydroxyalkyl, hydroxyalkoxy, acetyloxy, and alkoxycarbonylalkoxy, except where this definition of $R_2$ is excluded.

For certain embodiments (e.g., of any one of Formulas I, Ia, and II through XII), including any one of the above embodiments, $R_2$ is heteroaryl which is unsubstituted or substituted by one or more substituents independently selected from the group consisting of alkyl, alkoxy, alkylthio, aryl, halogen, haloalkyl, haloalkoxy, cyano, nitro, amino, hydroxy, hydroxyalkyl, hydroxyalkoxy, acetyloxy, and alkoxycarbonylalkoxy, and wherein heteroaryl is a monocyclic, 5 or 6 membered ring containing 1 or two heteroatoms, except where this definition of $R_2$ is excluded.

For certain embodiments (e.g., of any one of Formulas I, Ia, and II through XII), including any one of the above embodiments, $R_2$ is selected from the group consisting of furan-2-yl, pyrrol-2-yl, 1-methylpyrrol-2-yl, thiophen-2-yl, 3-methylthiophen-2-yl, 5-methylthiophen-2-yl, imidazol-2-yl, thiazol-2-yl, pyridin-2-yl, pyridin-3-yl, and pyridin-4-yl, each of which is unsubstituted or substituted by one or more substituents independently selected from the group consisting of methyl, methoxy, bromo, chloro, fluoro, trifluoromethyl, trifluoromethoxy, cyano, nitro, hydroxy, except where this definition of $R_2$ is excluded.

For certain embodiments (e.g., of any one of Formulas I, Ia, and II through XII), including any one of the above embodiments, $R_2$ is phenyl which is unsubstituted or substituted by one or more substituents independently selected from the group consisting of alkyl, alkoxy, alkylthio, aryl, halogen, haloalkyl, haloalkoxy, cyano, nitro, amino, hydroxy, hydroxyalkyl, hydroxyalkoxy, acetyloxy, and alkoxycarbonylalkoxy, except where this definition of $R_2$ is excluded. For certain of these embodiments, phenyl is unsubstituted or substituted by one or more substituents independently selected from the group consisting of methyl, methoxy, bromo, chloro, fluoro, trifluoromethyl, trifluoromethoxy, cyano, nitro, and hydroxy, except where this definition of $R_2$ is excluded.

For certain embodiments (e.g., of any one of Formulas I, Ia, and II through XII), including any one of the above embodiments, $R_1$ is —X—$R_4$. For certain of these embodiments (e.g., of any one of Formulas I and II through XII), $R_1$ is other than hydrogen. For certain of these embodiments (e.g., of any one of Formulas I, II, III, and IV), $R_1$ is other than hydrogen, methyl, or phenyl. For certain of these embodiments (e.g., of any one of Formulas I, II, and III), $R_1$ is other than hydrogen, methyl, or phenyl; and the compound is other than N-[1,1-dimethyl-2-(2-methyl-2H-pyrazolo[3,4-c]quinolin-1-yl) ethyl]benzamide. For certain of these embodiments, X is —(CH$_2$)$_{1-3}$—, and $R_4$ is aryl, heteroaryl, or heterocyclyl, each of which is unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of heterocyclyl, oxo, amidino, and oximido. For certain of these embodiments, $R_4$ is a saturated, nitrogen-containing heterocyclyl group which is unsubstituted or substituted by oxo, amidino, or oximido. For certain of these embodiments, $R_4$ is selected from the group consisting of piperidin-1-yl, piperidin-2-yl, piperidin-3-yl, piperidin-4-yl, piperazin-1-yl, morpholin-4-yl, morpholin-2-yl, pyrrolidin-1-yl, and pyrrolidin-2-yl. For certain of these embodiments, $R_4$ is piperidin-4-yl or piperazin-1-yl. For certain of these embodiments, X is —CH$_2$— or —CH$_2$CH$_2$—.

For certain embodiments (e.g., of any one of Formulas I, Ia, and II through XII), including any one of the above embodi ments, except where $R_1$ is —X—$R_4$, $R_1$ is —X—Y—$R_4$. For certain of these embodiments, X is —$(CH_2)_{1-3}$—, Y is

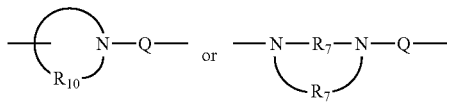

wherein Q is a bond, —$C(R_6)$—, —$S(O)_2$—, —$C(R_6)$—O—, $R_7$ is ethylene, $R_{10}$ is —$(CH_2)_{4-5}$—, and $R_4$ is $C_{1-4}$ alkyl, phenyl, 4-chlorophenyl, 4-fluorophenyl, benzyl, 4-chlorobenzyl, or 4-fluorobenzyl. For certain of these embodiments, $R_{10}$ is —$(CH_2)_5$—. For certain of these embodiments, X is —$CH_2CH_2$—. Alternatively, for certain of these embodiments where $R_1$ is —X—Y—$R_4$, X is —$CH_2$—, Y is —O— or —$N(R_8)$—, and $R_4$ is aryl, heteroaryl, or heterocyclyl.

For certain embodiments (e.g., of any one of Formulas I, Ia, and II through XII), including any one of the above embodiments, except where $R_1$ is —X—$R_4$ or —X—Y—$R_4$, $R_1$ is —X—Y—X—Y—$R_4$. For certain of these embodiments, $R_1$ is

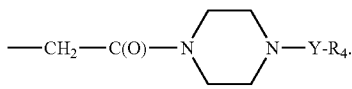

For certain of these embodiments, Y is —C(O)—, —$S(O)_2$—, —$S(O)_2$—$N(R_8)$—, or —C(O)—$N(R_8)$—. For certain of these embodiments, $R_4$ is $C_{1-5}$ alkyl, phenyl, or pyridyl.

For certain embodiments (e.g., of any one of Formulas I, Ia, and II through XII), including any one of the above embodiments, except where $R_1$ is —X—$R_4$, —X—Y—$R_4$, or —X—Y—X—Y—$R_4$, $R_1$ is —X—$R_5$. For certain of these embodiments, —X— is —$(CH_2)_{1-4}$—. For certain of these embodiments, $R_5$ is

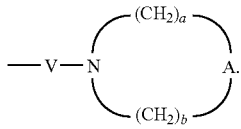

For certain of these embodiments, V is —C(O)—, A is —$N(R_4)$—, and a and b are both 2.

For certain embodiments, including any one of the above embodiments where $R_3$ is present, $R_3$ is at the 7-position of the pyrazoloquinoline or pyrazolonaphthyridine. In certain of these embodiments, m is 1, and n is 0.

Alternatively, for certain embodiments, including any one of the above embodiments where $R_3$ is present, $R_3$ is at the 8-position of the pyrazoloquinoline or pyrazolonaphthyridine. In certain of these embodiments, m is 1, and n is 0.

For certain embodiments, $R_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo, and in the case of heterocyclyl, amidino and oximido.

For certain embodiments, $R_4$ is aryl, heteroaryl, or heterocyclyl, each of which is unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of heterocyclyl, oxo, amidino, and oximido.

For certain embodiments, $R_4$ is a saturated, nitrogen-containing heterocyclyl group which is unsubstituted or substituted by oxo, amidino, or oximido.

For certain embodiments, $R_4$ is selected from the group consisting of piperidin-1-yl, piperidin-2-yl, piperidin-3-yl, piperidin-4-yl, piperazin-1-yl, morpholin-4-yl, morpholin-2-yl, pyrrolidin-1-yl, and pyrrolidin-2-yl.

For certain embodiments, $R_4$ is piperidin-4-yl or piperazin-1-yl.

For certain embodiments, $R_4$ is $C_{1-4}$ alkyl, phenyl, 4-chlorophenyl, 4-fluorophenyl, benzyl, 4-chlorobenzyl, or 4-fluorobenzyl.

For certain embodiments, $R_4$ is aryl, heteroaryl, or heterocyclyl.

For certain embodiments, $R_4$ is alkyl, aryl, or heteroaryl.

For certain embodiments, $R_4$ is $C_{1-5}$ alkyl, phenyl, or pyridyl.

For certain embodiments, $R_4$ is alkyl.

For certain embodiments, $R_4$ is aryl.

For certain embodiments, $R_4$ is heteroaryl.

For certain embodiments, $R_5$ is selected from the group consisting of

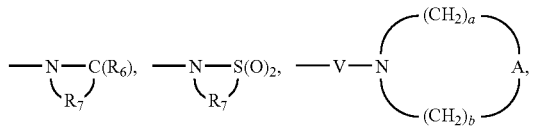

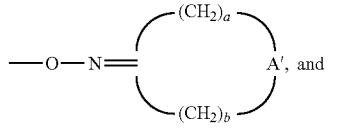

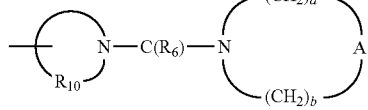

For certain embodiments, $R_5$ is selected from the group consisting of

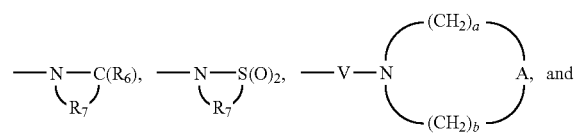

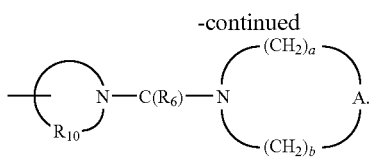

For certain embodiments, $R_5$ is selected from the group consisting of

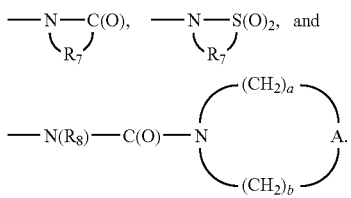

For certain embodiments, $R_5$ is

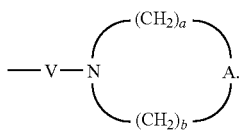

For certain of these embodiments, V is —C(O)—. For certain of these embodiments, A is —N($R_4$)—. For certain of these embodiments, a and b are both 2.

For certain embodiments, $R_6$ is selected from the group consisting of =O and =S.

For certain embodiments, $R_6$ is =O. For certain embodiments, $R_6$ is =S.

For certain embodiments, $R_7$ is $C_{2-7}$ alkylene. In certain embodiments, $R_7$ is $C_{3-4}$ alkylene. In certain embodiments, $R_7$ is ethylene.

For certain embodiments, $R_8$ is selected from the group consisting of hydrogen, alkyl, alkoxyalkylenyl, hydroxyalkylenyl, arylalkylenyl, and heteroarylalkylenyl. In certain embodiments, $R_9$ is hydrogen. In certain embodiments, $R_9$ is alkyl.

For certain embodiments, $R_9$ is selected from the group consisting of hydrogen and alkyl. In certain embodiments, $R_9$ is alkyl. In certain embodiments, $R_9$ is hydrogen.

For certain embodiments, $R_{10}$ is $C_{3-8}$ alkylene. In certain embodiments, $R_{10}$ is $C_{4-5}$ alkylene. In certain embodiments, $R_{10}$ is —$(CH_2)_{4-5}$—. In certain embodiments, $R_{10}$ is —$(CH_2)_5$—.

For certain embodiments, A is selected from the group consisting of —O—, —C(O)—, —S(O)$_{0-2}$—, and —N($R_4$)—. In certain embodiments, A is selected from the group consisting of —O—, —C(O)—, and —N($R_4$)—. In certain embodiments, A is —O—. In certain embodiments, A is —N($R_4$)—.

For certain embodiments, A' is selected from the group consisting of —O—, —S(O)$_{0-2}$—, —N(-Q-$R_4$)—, and —CH$_2$—. In certain embodiments, A' is —O—. In certain embodiments, A' is —CH$_2$—. In certain embodiments, A' is —N(-Q-$R_4$)—. In certain of these embodiments, Q is a bond and $R_4$ is alkyl.

For certain embodiments, Q is selected from the group consisting of a bond, —C($R_6$)—, —C($R_6$)—C($R_6$)—, —S(O)$_2$—, —C($R_6$)—N($R_8$)—W—, —S(O)$_2$—N($R_8$)—, —C($R_6$)—O—, —C($R_6$)—S—, and —C($R_6$)—N(O$R_9$)—.
In certain embodiments, Q is a bond, —C($R_6$)—, —S(O)$_2$—, or —C($R_6$)—O—. In certain embodiments, Q is a bond, —C(O)—, —S(O)$_2$—, —C($R_6$)—N($R_8$)—, or —S(O)$_2$—N($R_8$)—. In certain embodiments, Q is a bond, —C($R_6$)—, —S(O)$_2$—, or —C($R_6$)—N($R_8$)—W—. In certain embodiments, Q is a bond.

For certain embodiments, V is selected from the group consisting of —C($R_6$)—, —O—C($R_6$)—, —N($R_8$)—C($R_6$)—, and —S(O)$_2$—. In certain embodiments, V is —C($R_6$)—. In certain embodiments, V is —C(O)—. In certain embodiments, V is —N($R_8$)—C($R_6$)—.

For certain embodiments, W is selected from the group consisting of a bond, —C(O)—, and —S(O)$_2$—. In certain embodiments, W is selected from the group consisting of a bond and —C(O)—. In certain embodiments, W is a bond.

For certain embodiments, X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups.

For certain embodiments, X is alkylene. In certain embodiments, X is $C_{1-4}$ alkylene. In certain embodiments, —X— is —$(CH_2)_{1-4}$—. In certain embodiments, X is —$(CH_2)_{1-3}$—. In certain embodiments, X is —$CH_2CH_2$—. In certain embodiments, X is —$CH_2$—.

For certain embodiments, Y is selected from the group consisting of —O—, —S(O)$_{0-2}$—, —S(O)$_2$—N($R_8$)—, —C($R_6$)—, —C($R_6$)—O—, —O—C($R_6$)—, —O—C(O)—O—, —N($R_8$)-Q-, —C($R_6$)—N($R_8$)—, —O—C($R_6$)—N($R_8$)—, —C($R_6$)—N(O$R_9$)—, —O—N($R_8$)-Q-, —O—N=C($R_4$)—, —C(=N—O—$R_8$)—, —C(=N—O—$R_8$)—NH—, —CH(—N(—O—$R_8$)-Q-$R_4$)—,

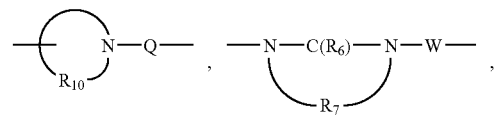

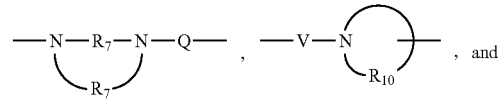

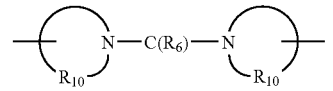

For certain embodiments, Y is

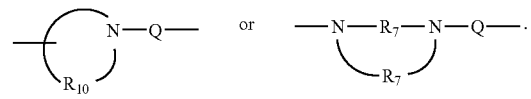

In certain of these embodiments, Q is a bond, —C($R_6$)—, —S(O)$_2$—, or —C($R_6$)—O—, $R_7$ is ethylene, and $R_{10}$ is —$(CH_2)_{4-5}$—.

For certain embodiments, Y is —C(O)—, —S(O)$_2$—, —S(O)$_2$—N($R_8$)—, or —C(O)—N($R_8$)—.

For certain embodiments, Y is —O— or —N($R_8$)—.

For certain embodiments, Z is a bond or —O—. In certain embodiments, Z is a bond. In certain embodiments, Z is —O—.

For certain embodiments, a and b are independently integers from 1 to 6 with the proviso that a+b is ≦7. For certain embodiments, a and b are each the integer 2.

For certain embodiments (e.g., of Formula III), n is 0, or m is 0.

For certain embodiments (e.g., of Formula III), m and n are 0.

For certain embodiments (e.g., of Formula III), m is 0, and n is 1.

For certain embodiments (e.g., of Formula III), m is 1, and n is 0.

For certain embodiments (e.g., of Formulas V through VIII), p is 0, or m is 0.

For certain embodiments (e.g., of Formulas V through VIII), m and p are 0.

For certain embodiments (e.g., of Formulas V through VIII), m is 0, and p is 1.

For certain embodiments (e.g., of Formulas V through VIII), m is 1, and p is 0.

For certain embodiments (e.g., of Formulas IV and IX through XII), n is 0.

For certain embodiments, the present invention provides a pharmaceutical composition comprising a therapeutically effective amount of a compound or salt of any one of Formulas I, Ia, II, III, IV, V, VI, VII, VIII, IX, X, XI, XII, or any one of the above embodiments in combination with a pharmaceutically acceptable carrier.

For certain embodiments, the present invention provides a method of inhibiting cytokine biosynthesis comprising administering an effective amount of a compound or salt of any one of Formulas I, Ia, II, III, IV, V, VI, VII, VIII, IX, X, XI, XII, or any one of the above embodiments or administering any one of the above pharmaceutical compositions to the animal. In certain of these embodiments the cytokine is TNF-α or IL-1.

For certain embodiments, the present invention provides a method of therapeutic treatment of a disease by inhibiting cytokine biosynthesis, comprising administering a therapeutically effective amount of a compound or salt of any one of Formulas I, Ia, II, III, IV, V, VI, VII, VIII, IX, X, XI, XII, or any one of the above embodiments or administering any one of the above pharmaceutical compositions to the animal. In certain of these embodiments the cytokine is TNF-α or IL-1.

For certain embodiments, the present invention provides a method of prophylactic treatment of a disease by inhibiting cytokine biosynthesis, comprising administering a therapeutically effective amount of a compound or salt of any one of Formulas I, Ia, II, III, IV, V, VI, VII, VIII, IX, X, XI, XII, or any one of the above embodiments or administering any one of the above pharmaceutical compositions to the animal. In certain of these embodiments the cytokine is TNF-α or IL-1.

Preparation of the Compounds

Compounds of the invention may be synthesized by synthetic routes that include processes analogous to those well known in the chemical arts, particularly in light of the description contained herein. The starting materials are generally available from commercial sources such as Aldrich Chemicals (Milwaukee, Wis., USA) or are readily prepared using methods well known to those skilled in the art (e.g. prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie*, 4, Aufl. Ed. Springer-Verlag, Berlin, Germany, including supplements (also available via the Beilstein online database)).

For illustrative purposes, the reaction schemes depicted below provide potential routes for synthesizing the compounds of the present invention as well as key intermediates. For more detailed description of the individual reaction steps, see the EXAMPLES section below. Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

Conventional methods and techniques of separation and purification can be used to isolate compounds of the invention, as well as various intermediates related thereto. Such techniques may include, for example, all types of chromatography (high performance liquid chromatography (HPLC), column chromatography using common absorbents such as silica gel, and thin layer chromatography), recrystallization, and differential (i.e., liquid-liquid) extraction techniques.

For some embodiments, compounds of the invention can be prepared according to Reaction Scheme I, where R, $R_1$, $R_2$, $R_3$, n and m are as defined above and $R_{C1}$ is a subset of $R_C$.

In step (1) of Reaction Scheme I, an indole of Formula XX is acylated to provide an oxalated indole of Formula XXI. The reaction can be carried out by adding ethyl chlorooxoacetate to a solution of an indole of Formula XX in a suitable solvent such as diethyl ether in the presence of pyridine. The reaction can be carried out at a sub-ambient temperature such as 0° C. Many indoles of Formula XX are known. Some are commercially available and others can be readily prepared using known synthetic methods.

In step (2) of Reaction Scheme I, an oxalated indole of Formula XXI is rearranged to a pyrazolo[3,4-c]quinolin-4-one of Formula XXII. The reaction can be carried out by adding a hydrazine of Formula $R_2NHNH_2$ to a solution of an oxalated indole of Formula XXI in a solvent or solvent mix such as ethanol/acetic acid in the presence of hydrochloric acid. The reaction can be carried out at an elevated temperature such as at reflux.

If step (2) is carried out using hydrazine, the resulting pyrazolo[3,4-c]quinolin-4-one of Formula XXII where $R_2$ is hydrogen can be further elaborated using known synthetic methods. For example, a pyrazolo[3,4-c]quinolin-4-one of Formula XXII where $R_2$ is hydrogen can be alkylated. The alkylation is conveniently carried out by treating a solution of a pyrazolo[3,4-c]quinolin-4-one of Formula XXII, where $R_2$ is hydrogen, with a base such as sodium ethoxide followed by the addition of an alkyl halide. The reaction can be run in a suitable solvent such as ethanol and can be carried out at an elevated temperature, for example, the reflux temperature of the solvent, or at ambient temperature. Alternatively, a pyrazolo[3,4-c]quinolin-4-one of Formula XXII where $R_2$ is hydrogen can undergo a Buchwald amination with an aryl halide or heteroaryl halide. Numerous alkyl halides, aryl halides, and heteroaryl halides are commercially available; others can be prepared using known synthetic methods.

Step (2) can also be carried out using a hydrazine that will install a removable group at $R_2$. Examples of such hydrazines include benzylhydrazine and tert-butylhydrazine. At a later point in the synthetic pathway the group can be removed using conventional methods to provide a compound in which $R_2$ is hydrogen. The compound may then be further elaborated using the methods described above.

In step (3) of Reaction Scheme I, an aldehyde group is installed on a pyrazolo[3,4-c]quinolin-4-one of Formula XXII to provide a pyrazolo[3,4-c]quinolin-4-one of Formula IIIa, which is a subgenus of Formula III. The reaction can be carried out by deprotonating a pyrazolo[3,4-c]quinolin-4-one of Formula XXII with 2 equivalents of n-butyl lithium followed by treatment with N,N-dimethylformamide (DMF) and quenching with hydrochloric acid. The reaction can be carried out at an elevated temperature such as 50° C. in a suitable solvent such as tetrahydrofuran.

In step (4) of Reaction Scheme I, a pyrazolo[3,4-c]quinolin-4-one of Formula IIIa undergoes further elaboration using conventional synthetic methods to provide a pyrazolo[3,4-c]quinolin-4-one of Formula IIIb, which is a subgenus of Formula III. For example, the aldehyde can be reacted with several different classes of nucleophiles such as phosphonium ylides (Wittig olefination) or phosphonates (Horner Wadsworth olefination) to provide alkenes; amines using reductive amination to provide secondary or tertiary amines; and Grignard reagents or lithiated alkynes or alkenes to provide alcohols which may then be oxidized to provide ketones. When reaction with a nucleophile provides a substituted olefin, the olefin may be reduced using conventional methods such as hydrogenation using a conventional heterogeneous hydrogenation catalyst such as palladium on carbon. Alternatively, the aldehyde can be reduced to the alcohol using known methods, for example, treating a solution of the aldehyde with sodium borohydride. The alcohol can then be converted to a halide or an oxygen based leaving group such as a triflate, mesylate, or tosylate using conventional methods. The halide or oxygen based leaving group can then be reacted with a variety of nucleophiles.

In step (5) of Reaction Scheme I, a pyrazolo[3,4-c]quinolin-4-one of Formula IIIb is chlorinated to provide to provide a 4-chloropyrazolo[3,4-c]quinoline of Formula IIIc, which is a subgenus of Formula III. The reaction can be carried out by combining a pyrazolo[3,4-c]quinolin-4-one of Formula IIIb with phosphorous oxychloride and heating.

In step (6) of Reaction Scheme I, a 4-chloropyrazolo[3,4-c]quinoline of Formula IIIc undergoes further elaboration using conventional synthetic methods to provide a pyrazolo [3,4-c]quinoline of Formula IIId, which is a subgenus of Formula III. For example, the chloro group can be displaced with nucleophiles such as alkoxides, phenoxides, or amines to provide compounds of Formula IIId wherein $R_{C1}$ is alkoxy, unsubstituted or substituted phenoxy, amino, alkylamino, dialkylamino, benzylamino, or cyclic amino. Alternatively, a 4-chloropyrazolo[3,4-c]quinoline of Formula IIIc can undergo a palladium-catalyzed coupling reaction such as a Suzuki coupling or Sonogoshira coupling with a boronic acid of Formula $R_D$—$B(OH)_2$, an anhydride thereof, or a boronic ester of Formula $R_D$—$B(O-alkyl)_2$ where $R_D$ is phenyl, substituted phenyl, or heteroaryl to provide compounds of Formula IIId wherein $R_{C1}$ is phenyl, substituted phenyl, or heteroaryl.

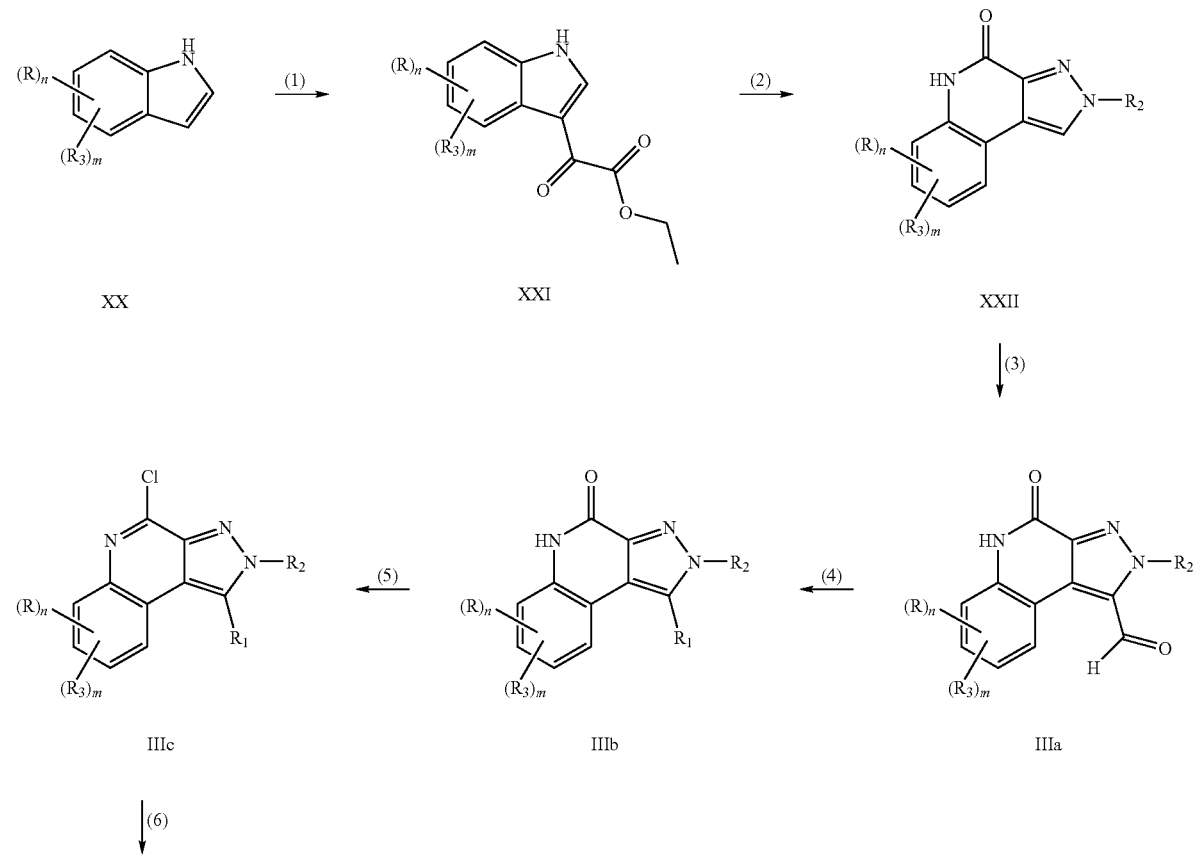

Reaction Scheme I

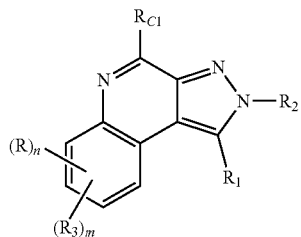

IIId

For some embodiments, compounds of the invention can be prepared according to Reaction Scheme II, where R, $R_1$, $R_2$, $R_3$, n and m are as defined above and $R_{C1}$ is a subset of $R_C$.

In step (1) of Reaction Scheme II, an ethyl indole carboxylate of Formula XXIII is converted to an aldehyde substituted indole of Formula XXIV. The carboxylate group is reduced to the alcohol using conventional methods, for example, by treating a solution of an indole of Formula XXIII with lithium aluminum hydride. The alcohol group is then oxidized to the aldehyde using conventional methods, for example, by treating a solution of the alcohol substituted indole with sulfur trioxide pyridine, dimethyl sulfoxide (DMSO), and triethylamine.

In step (2) of Reaction Scheme II, an aldehyde substituted indole of Formula XXIV is further elaborated using the methods described in step (4) of Reaction Scheme I to provide a substituted indole of Formula XXV.

In step (3) of Reaction Scheme II, a substituted indole of Formula XXV is acylated using the method described in step (1) of Reaction Scheme I to provide an oxalated indole of Formula XXVI.

In step (4) of Reaction Scheme II, an oxalated indole of Formula XXVI is rearranged to a pyrazolo[3,4-c]quinolin-4-one of Formula IIIb using the method described in step (2) of Reaction Scheme I.

Steps (5) and (6) of Reaction Scheme II are carried out using the methods of steps (5) and (6) of Reaction Scheme I.

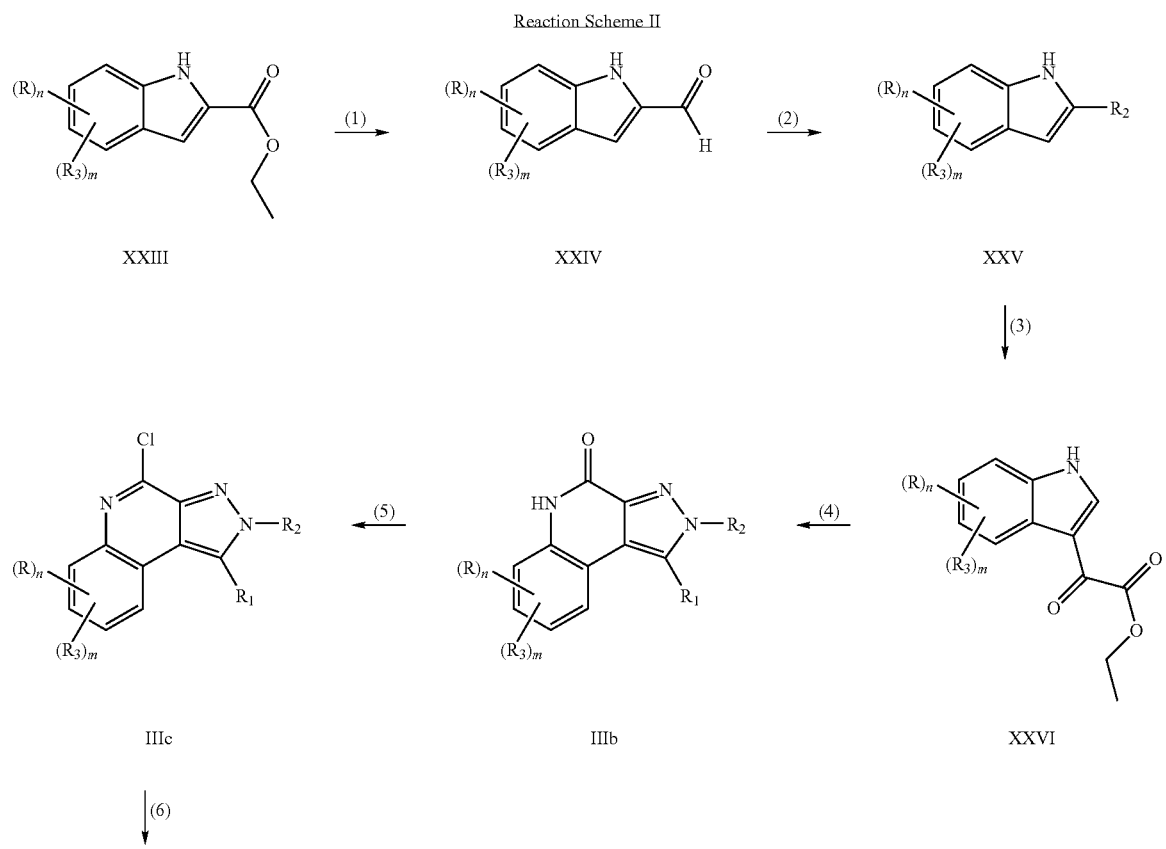

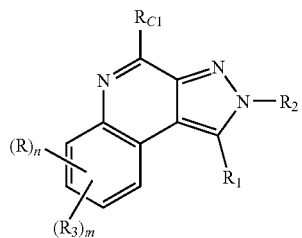

IIId

For some embodiments, compounds of the invention can also be prepared according to Reaction Scheme III, where n is defined as above and $R_a$, $R_{1a}$, $R_{2a}$, and $R_{3a}$ are subsets of R, $R_1$, $R_2$, and $R_3$ as defined above that do not include those substituents which one skilled in the art would recognize as being susceptible to oxidation in step (5). These susceptible substituents include —S— or heteroaryl groups.

Acetals of Formula XXVII are reported in the literature and can be prepared using known synthetic methods, Royals, E. E., Robinson, A. G. III, *J. Am. Chem. Soc.*, 78, 4161 (1956). For example, a ketone of Formula $CH_3C(O)R_{1a}$ can be condensed with ethyl diethoxyacetate under Claisen condensation conditions to provide an acetal of Formula XXVII. The reaction can be carried out by adding sodium tert-butoxide to a solution of ethyl diethoxyacetate and the ketone of Formula $CH_3C(O)R_{1a}$ in ethanol and heating the reaction at reflux. Numerous ketones of Formula $CH_3C(O)R_{1a}$ are commercially available. Others can be readily prepared using known synthetic methods. In step (1) of Reaction Scheme III, an acetal of Formula XXVII is reacted with a hydrazine of Formula $R_{2a}$—NH—$NH_2$ to provide a pyrazole of Formula XXVIII. The reaction can be carried out by slowly adding the hydrazine to a solution of an acetal of Formula XXVII in a suitable solvent such as ethanol. The reaction can be run at ambient temperature.

In step (2) of Reaction Scheme III, the acetal in the pyrazole of Formula XXVIII is converted to an aldehyde under acidic conditions. The reaction can be carried out by treating the acetal-substituted pyrazole of Formula XXVIII with hydrochloric acid in a suitable solvent such as tetrahydrofuran. The reaction can be carried out at ambient temperature to provide an aldehyde-substituted pyrazole of Formula XXIX.

In step (3) of Reaction Scheme III, a pyrazole of Formula XXIX is brominated to provide a bromo-substituted pyrazole of Formula XXX. The bromination can be carried out by adding bromine to a solution of the aldehyde-substituted pyrazole of Formula XXIX and potassium acetate in acetic acid. The reaction can be carried out at ambient temperature.

In step (4) of Reaction Scheme III, a bromo-substituted pyrazole of Formula XXX undergoes a transition-metal catalyzed cross coupling reaction with a reagent of Formula XXXI. Reagents of Formula XXXI, where M is, for example, —$B(OH)_2$, —$B(O\text{-alkyl})_2$, —$Sn(\text{alkyl})_3$, and —Zn-Halide, are known to undergo coupling reactions. Several reagents of Formula XXXI are commercially available; others can be prepared using known synthetic methods. For example, tert-butoxycarbonyl (Boc)-protected anilines undergo directed ortho metalation in the presence of butyllithium reagents. The resulting organolithium intermediate reacts with electrophiles such as $B(O\text{-alkyl})_3$ and $ClSn(\text{alkyl})_3$ to provide compounds of Formula XXXI, where M is —$B(O\text{-alkyl})_2$ or —$B(OH)_2$ and —$Sn(\text{alkyl})_3$, respectively, after removal of the Boc protecting group.

In step (4), a Suzuki coupling reaction is conveniently carried out by heating a mixture of the bromo-substituted pyrazole of Formula XXX, palladium (II) acetate, triphenylphosphine, and a boron reagent of Formula XXXI, where M is —$B(OH)_2$ or —$B(O\text{-alkyl})_2$, in the presence of a base such as sodium carbonate. The reaction is carried out in a suitable solvent or solvent mixture such as n-propanol:water and can be heated at an elevated temperature such as 100° C. Under these reaction conditions, intramolecular condensation of the amine with the aldehyde group takes place to form a pyrazolo[3,4-c]quinoline of Formula IIIe, which is a subgenus of Formula III.

In step (5) of Reaction Scheme III, a pyrazolo[3,4-c]quinoline of Formula IIIe is oxidized to provide a pyrazolo[3,4-c]quinoline-5N-oxide of Formula XXXII using a conventional oxidizing agent capable of forming N-oxides. The reaction can be carried out by adding 3-chloroperoxybenzoic acid to a solution of a compound of Formula IIIe in a solvent such as dichloromethane or chloroform. The reaction can be carried out at ambient temperature.

In step (6) of Reaction Scheme III, a pyrazolo[3,4-c]quinoline-5N-oxide of Formula XXXII is chlorinated to provide to provide a 4-chloropyrazolo[3,4-c]quinoline of Formula IIIf, which is a subgenus of Formula III. The reaction can be carried out as described in step (5) of Reaction Scheme I.

In step (7) of Reaction Scheme III, a 4-chloropyrazolo[3,4-c]quinoline of Formula IIIf undergoes further elaboration using conventional synthetic methods, as described in step (6) of Reaction Scheme I, to provide a pyrazolo[3,4-c]quinoline of Formula IIIg, which is a subgenus of Formula III.

Reaction Scheme III

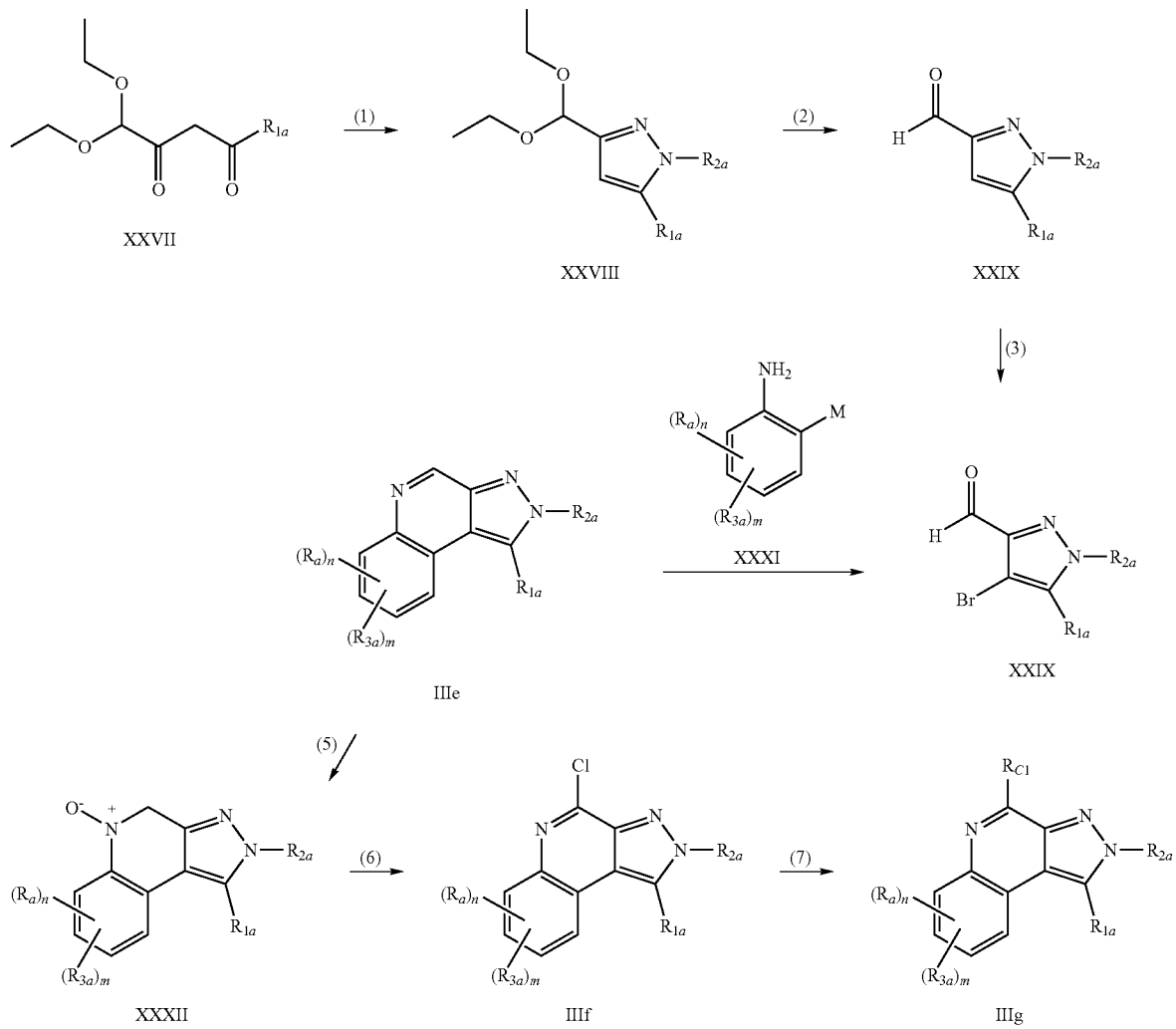

For some embodiments, compounds of the invention can be prepared according to Reaction Scheme IV, wherein $R_1$, $R_2$, and $R_{C1}$, are as defined above; R is selected from the group consisting of hydrogen, halogen, alkyl, alkenyl, haloalkyl, and dialkylamino; $R_{3b}$ and $R_{3c}$ are defined below, and $R_{4a}$ is methyl or benzyl.

Steps (1) through (6) of Reaction Scheme IV can be carried out as described for steps (1) through (6) of Reaction Scheme I or as described for steps (1) through (6) of Reaction Scheme II. Some benzyloxy-substituted indoles and methoxy-substituted indoles of Formula XXa are known; others can be prepared using known synthetic methods.

In step (7) of Reaction Scheme IV, the benzyl or methyl group of pyrazolo[3,4-c]quinoline of Formula IIIh, which is a subgenus of Formula III, is cleaved using conventional methods to provide a pyrazolo[3,4-c]quinolinol of Formula IIIi, which is a subgenus of Formula III. Cleavage of the benzyl group can be carried out on a Parr apparatus under hydrogenolysis conditions using a suitable heterogeneous catalyst such as palladium on carbon in a solvent such as ethanol. Alternatively, the reaction can be carried out by transfer hydrogenation in the presence of a suitable hydrogenation catalyst. The transfer hydrogenation can be carried out by adding ammonium formate to a solution of a pyrazolo[3,4-c] quinoline of Formula IIIh in a suitable solvent such as ethanol in the presence of a catalyst such as palladium on carbon. The reaction can be carried out at an elevated temperature, for example, the reflux temperature of the solvent. Demethylation can be carried out by treating a pyrazolo[3,4-c]quinoline of Formula IIIh with a solution of boron tribromide in a suitable solvent such as dichloromethane. The reaction can be carried out at a sub-ambient temperature such as 0° C. Alternatively, the demethylation can be carried out by heating a pyrazolo[3,4-c]quinoline of Formula IIIh with anhydrous pyridinium chloride at an elevated temperature, such as 210° C.

In step (8a) of Reaction Scheme IV, the hydroxy group of a pyrazolo[3,4-c]quinolinol of Formula IIIi is activated by conversion to a trifluoromethanesulfonate (triflate) group. The reaction can be carried out by treating a pyrazolo[3,4-c] quinolinol of Formula IIIi with N-phenyl-bis(trifluoromethanesulfonimide) in the presence of a tertiary amine such as triethylamine. The reaction can be carried out at ambient temperature in a suitable solvent such as DMF. The activation in step (8a) may also be accomplished by converting the hydroxy group to another good leaving group.

Step (9) of Reaction Scheme IV can be carried out using known palladium-catalyzed coupling reactions such as the Suzuki coupling, Heck reaction, the Stille coupling, and the Sonogashira coupling. For example, a triflate-substituted pyrazolo[3,4-c]quinoline of Formula XXXIII undergoes Suzuki coupling with a boronic acid of Formula $R_{3b}$—

B(OH)$_2$, an anhydride thereof, or a boronic acid ester of Formula R$_{3b}$—B(O-alkyl)$_2$; wherein R$_{3b}$ is —R$_{4b}$, —X$_e$—R$_4$, —X$_f$—Y—R$_4$, or —X$_f$—R$_5$; where X$_e$ is alkenylene; X$_f$ is arylene, heteroarylene, and alkenylene interrupted or terminated by arylene or heteroarylene; R$_{4b}$ is aryl or heteroaryl where the aryl or heteroaryl groups can be unsubstituted or substituted as defined in R$_4$ above; and R$_4$, R$_5$, and Y are as defined above. The coupling can be carried out by combining a triflate-substituted pyrazolo[3,4-c]quinoline of Formula XXXIII with a boronic acid or an ester or anhydride thereof in the presence of palladium (II) acetate, triphenylphosphine, and a base such as aqueous sodium carbonate in a suitable solvent such as n-propanol. The reaction can be carried out at an elevated temperature, for example, at the reflux temperature. Numerous boronic acids of Formula R$_{3b}$—B(OH)$_2$, anhydrides thereof, and boronic acid esters of Formula R$_{3b}$—B(O-alkyl)$_2$ are commercially available; others can be readily prepared using known synthetic methods.

Alternatively, the Heck reaction can be used in step (9) of Reaction Scheme IV to provide compounds of Formula IIIk, wherein R$_{3b}$ is —X$_e$—R$_{4b}$ or —X$_e$—Y—R$_4$, wherein X$_e$, Y, R$_4$, and R$_{4b}$ are as defined above. The Heck reaction can be carried out by coupling a triflate-substituted pyrazolo[3,4-c]quinoline of Formula XXXIII with a compound of the Formula H$_2$C=C(H)—R$_{4b}$ or H$_2$C=C(H)—Y—R$_4$. Several of these vinyl-substituted compounds are commercially available; others can be prepared by known methods. The reaction can be carried out by combining a triflate-substituted pyrazolo[3,4-c]quinoline of Formula XXXIII and the vinyl-substituted compound in the presence of palladium (II) acetate, triphenylphosphine or tri-ortho-tolylphosphine, and a base such as triethylamine in a suitable solvent such as acetonitrile or toluene. The reaction can be carried out at an elevated temperature such as 100-120° C. under an inert atmosphere.

Compounds of Formula IIIk, wherein R$_{3b}$ is —X$_g$—R$_4$, X$_g$ is alkynylene, and R$_4$ is as defined above, can also be prepared by palladium catalyzed coupling reactions such as the Stille coupling or Sonogashira coupling. These reactions are carried out by coupling a triflate-substituted pyrazolo[3,4-c]quinoline of Formula XXXIII with a compound of the Formula (alkyl)$_3$Sn—C≡C—R$_4$, (alkyl)$_3$Si—C≡C—R$_4$, or H—C≡C—R$_4$.

Compounds of Formula IIIk prepared as described above by palladium-mediated coupling reactions, wherein R$_{3b}$ is —X$_e$—R$_4$, —X$_e$—Y—R$_4$, —X$_{f2}$—Y—R$_4$, —X$_{f2}$—R$_5$, or —X$_g$—R$_4$, where X$_{f2}$ is alkenylene interrupted or terminated by arylene or heteroarylene, and X$_e$, X$_g$, Y, R$_4$, and R$_5$ are as defined above, can undergo reduction of the alkenylene or alkynylene group present to provide pyrazolo[3,4-c]quinolines of Formula IIIk wherein R$_{3b}$ is —X$_h$—R$_4$, —X$_h$—Y—R$_4$, —X$_i$—Y—R$_4$, or —X$_i$—R$_5$, where X$_h$ is alkylene; X$_i$ is alkylene interrupted or terminated by arylene or heteroarylene; and R$_4$, R$_5$, and Y are as defined above. The reduction can be carried out by hydrogenation using a conventional heterogeneous hydrogenation catalyst such as palladium on carbon. The reaction can be carried out on a Parr apparatus in a suitable solvent such as ethanol, methanol, or mixtures thereof.

In step (8b) of Reaction Scheme IV, a pyrazolo[3,4-c]quinolinol of Formula IIIi is converted to a pyrazolo[3,4-c]quinoline of Formula IIIj, wherein R$_{3c}$ is —O—R$_4$, —O—X—R$_4$, —O—X—Y—R$_4$, or —O—X—R$_5$, and X, Y, R$_4$, and R$_5$ are as defined above, using a Williamson-type ether synthesis. The reaction can be effected by treating a pyrazolo[3,4-c]quinolinol of Formula IIIi with an aryl, alkyl, or arylalkylenyl halide of Formula Halide-R$_4$, Halide-alkylene-R$_4$, Halide-alkylene-Y—R$_4$, or Halide-alkylene-R$_5$ in the presence of a base. Numerous alkyl, arylalkylenyl, and aryl halides of these formulas are commercially available, including substituted benzyl bromides and chlorides, substituted or unsubstituted alkyl or arylalkylenyl bromides and chlorides, bromo-substituted ketones, esters, and heterocycles, and substituted fluorobenzenes. Other halides of these formulas can be prepared using conventional synthetic methods. The reaction can be carried out by combining an alkyl, arylalkylenyl, or aryl halide with a pyrazolo[3,4-c]quinolinol of Formula IIIi in a solvent such as DMF or N,N-dimethylacetamide in the presence of a suitable base such as cesium carbonate. Optionally, catalytic tetrabutylammonium bromide can be added. The reaction can be carried out at ambient temperature or at an elevated temperature, for example 50° C. or 85° C., depending on the reactivity of the halide reagent.

Alternatively, step (8b) may be carried out using the Ullmann ether synthesis, in which an alkali metal aryloxide prepared from a pyrazolo[3,4-c]quinolinol of Formula IIIi reacts with an aryl halide in the presence of copper salts, to provide a pyrazolo[3,4-c]quinoline of Formula IIIj, where R$_{3c}$ is —O—R$_{4b}$, —O—X$_j$—R$_4$, or —O—X$_j$—Y—R$_4$, wherein X$_j$ is an arylene or heteroarylene and R$_{4b}$ is as defined above. Numerous substituted and unsubstituted aryl halides are commercially available; others can be prepared using conventional methods.

The methods described in steps (7) through (9) and (7) through (8b) can also be used to install R$_{3b}$ or R$_{3c}$ groups at an earlier stage in the synthetic pathway.

Reaction Scheme IV

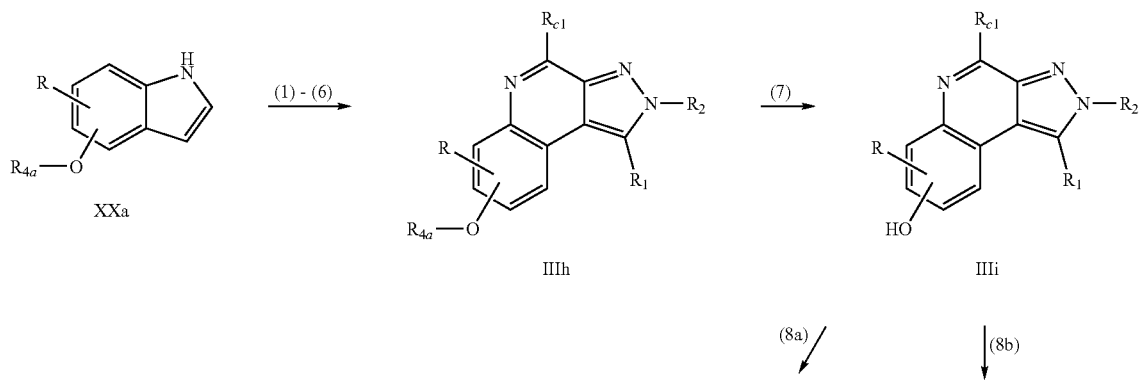

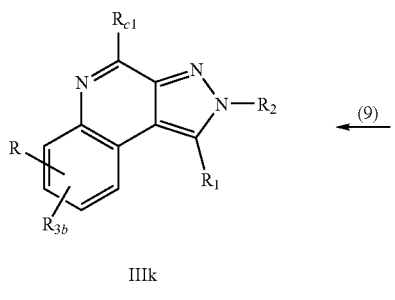 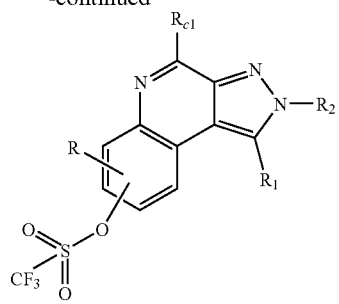 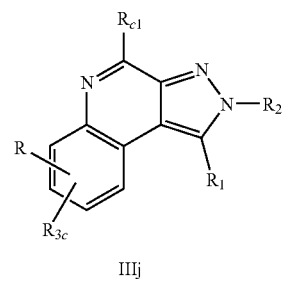

-continued

IIIk

XXXIII

IIIj

For some embodiments, compounds of the invention can be prepared according to Reaction Scheme V, where $R_b$, $R_{1b}$, $R_{2b}$, $R_{C2}$ are subsets of R, $R_1$, $R_2$, and $R_C$ as defined above that do not include those substituents which would be susceptible to reduction under the acidic hydrogenation conditions of the reaction and n is as defined above.

In Reaction Scheme V, a pyrazolo[3,4-c]quinoline of Formula IIIm is reduced to provide a 6,7,8,9-tetrahydro-2H-pyrazolo[3,4-c]quinoline of Formula IVa, which is a subgenus of Formula IV. The reaction may be carried out under heterogeneous hydrogenation conditions by adding platinum (IV) oxide to a solution or suspension of a pyrazolo[3,4-c]quinoline of Formula IIIm in a suitable solvent such as trifluoroacetic acid and placing the reaction under hydrogen pressure.

Alternatively, the reduction may be carried out at an earlier stage in the synthetic pathway.

Reaction Scheme V

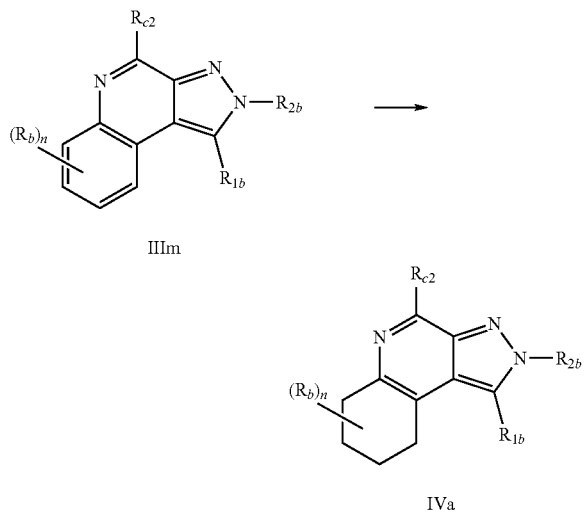

Pyrazolo[3,4-c]naphthyridines of the invention can be prepared by using an azaindole as the starting material in Reaction Schemes I, II, and IV. Azaindoles are known compounds. Some are commercially available and others can be prepared using known synthetic methods. Alternatively, pyrazolo[3,4-c]naphthyridines of the invention can be prepared by using an aminopyridine boronic acid in Reaction Scheme III. Aminopyridine boronic acids can be prepared using known methods, for example, by directed ortho metalation of Boc-protected aminopyridines and subsequent electrophilic substitution. Alternatively, for some isomers, halogen-lithium exchange and subsequent electrophilic substitution can be used. For example, halogen-lithium exchange can be carried out on a 2-bromopyridine that has a protected amino group in the 3-position; subsequent electrophilic substitution with tributyltin chloride and deprotection of the amino group provides 3-amino-2-tri-n-butylstannylpyridine.

6,7,8,9-Tetrahydro-2H-pyrazolo[3,4-c]naphthyridines can be prepared by reducing pyrazolo[3,4-c]naphthyridines using the method of Reaction Scheme V.

For some embodiments, compounds of the invention can be prepared according to Reaction Scheme VI where $R_2$ and $R_4$ are as described above, $X_1$ is —$(CH_2)_{1-4}$—, $Y_1$ is selected from —C(O)—, —S(O)$_2$—, —S(O)$_2$—N(R$_8$)—, and —C(O)—NH— where $R_8$ is as defined above, and Boc is tert-butoxycarbonyl.

In step (1) of Reaction Scheme VI, a pyrazolo[3,4-c]quinoline of Formula XXIIa is reacted with a Boc protected 4-(iodoalkyl)piperidine of Formula XXXIV to provide a pyrazolo[3,4-c]quinoline of Formula IIIn, a subgenus of Formula III. The reaction can be carried out by first deprotonating a pyrazolo[3,4-c]quinoline of Formula XXIIa by treating a solution of a compound of Formula XXIIa in a suitable solvent such as tetrahydrofuran with n-butyllithium optionally in the presence of N,N,N'N'-tetramethylethylenediamine. The reaction can be run at a sub-ambient temperature such as 0° C. The resulting anion is then treated with a Boc protected 4-(iodoalkyl)piperidine of Formula XXXIV. The reaction can be run at a sub-ambient temperature such as −78° C. Pyrazolo[3,4-c]quinolines of Formula XXIIa can be prepared as described in Reaction Scheme I. Boc protected 4-(iodoalkyl)piperidines of Formula XXXIV can be prepared using conventional synthetic methods.

In step (2) of Reaction Scheme VI, the Boc group on a pyrazolo[3,4-c]quinoline of Formula IIIn is removed under acidic conditions to provide a pyrazolo[3,4-c]quinoline of Formula IIIo, a subgenus of Formula III. The reaction can be carried out by combining a compound of Formula IIIn with concentrated hydrochloric acid and stirring the resulting mixture at ambient temperature.

In step (3a) of Reaction Scheme VI, a pyrazolo[3,4-c]quinoline of Formula IIIo is converted into an amide, sulfonamide, sulfamide, or urea of Formula IIIp, a subgenus of Formula III using conventional methods.

For example, a compound of Formula IIIo or a salt thereof can react with an acid chloride of Formula $R_4C(O)Cl$ to provide a compound of Formula IIIp in which $Y_1$ is —C(O)—. In addition, a compound of Formula IIIo can react with sulfonyl chloride of Formula $R_4S(O)_2Cl$ or a sulfonic anhydride of Formula $(R_4S(O)_2)_2O$ to provide a compound of Formula IIIp in which $Y_1$ is —S(O)$_2$—. Numerous acid chlorides of Formula $R_4C(O)Cl$, sulfonyl chlorides of Formula $R_4S(O)_2Cl$, and sulfonic anhydrides of Formula $(R_4S(O)_2)_2O$ are commercially available; others can be readily prepared using known synthetic methods. The reaction can be carried out by adding the acid chloride of Formula $R_4C(O)Cl$, sulfonyl chloride of Formula $R_4S(O)_2Cl$, or sulfonic anhydride of Formula $(R_4S(O)_2)_2O$ to a solution or suspension of a compound of Formula IIIo in a suitable solvent such as chloroform, dichloromethane, N,N-dimethylacetamide (DMA), or N,N-dimethylformamide (DMF). Optionally a base such as triethylamine or N,N-diisopropylethylamine can be added. The reaction can be carried out at ambient temperature or at a sub-ambient temperature such as 0° C.

Ureas of Formula IIIp, where $Y_1$ is —C(O)—NH— can be prepared by reacting a compound of Formula IIIo or a salt thereof with isocyanates of Formula $R_4N=C=O$. Numerous isocyanates of Formula $R_4N=C=O$ are commercially available; others can be readily prepared using known synthetic methods. The reaction can be carried out by adding the isocyanate of Formula $R_4N=C=O$ to a solution or suspension of a compound of Formula IIIo in a suitable solvent such as DMA, DMF, or chloroform. Optionally a base such as triethylamine or N,N-diisopropylethylamine can be added. The reaction can be carried out at ambient temperature or a sub-ambient temperature such as 0° C. Alternatively, a compound of Formula IIIo can be treated with a carbamoyl chloride of Formula Cl-C(O)-heterocyclyl, wherein heterocyclyl is attached at a nitrogen atom, to provide a compound of Formula IIIp, wherein $Y_1$ is —C(O)— and $R_4$ is heterocyclyl attached at a nitrogen atom.

Sulfamides of Formula IIIp, where $Y_1$ is —$S(O)_2$—N($R_8$)—, can be prepared by reacting a compound or salt of Formula IIIo with sulfuryl chloride to generate a sulfamoyl chloride in situ, and then reacting the sulfamoyl chloride with an amine of Formula $HN(R_8)R_4$. Alternatively, sulfamides of Formula IIIp can be prepared by reacting a compound of Formula IIIo with a sulfamoyl chloride of Formula $R_4(R_8)N$—$S(O)_2Cl$. Many sulfonyl chlorides of Formula $R_4S(O)_2Cl$ and amines of Formula $HN(R_8)R_4$, and some sulfamoyl chlorides of Formula $R_4(R_8)N$—$S(O)_2Cl$ are commercially available; others can be prepared using known synthetic methods.

In step (3b) of Reaction Scheme VI, a pyrazolo[3,4-c]quinoline of Formula IIIo undergoes reductive alkylation to provide a pyrazolo[3,4-c]quinoline of Formula IIIq, a subgenus of Formula III. The alkylation can be carried out in two parts by (i) adding an aldehyde or ketone to a solution of a compound of Formula IIIo or a salt thereof in a suitable solvent such as DMF, THF, or methanol in the presence of a base such as N,N-diisopropylethylamine. In part (ii) the reduction is carried out by adding a suitable reducing agent such as the borane-pyridine complex. Both part (i) and part (ii) can be carried out at ambient temperature.

Reaction Scheme VI

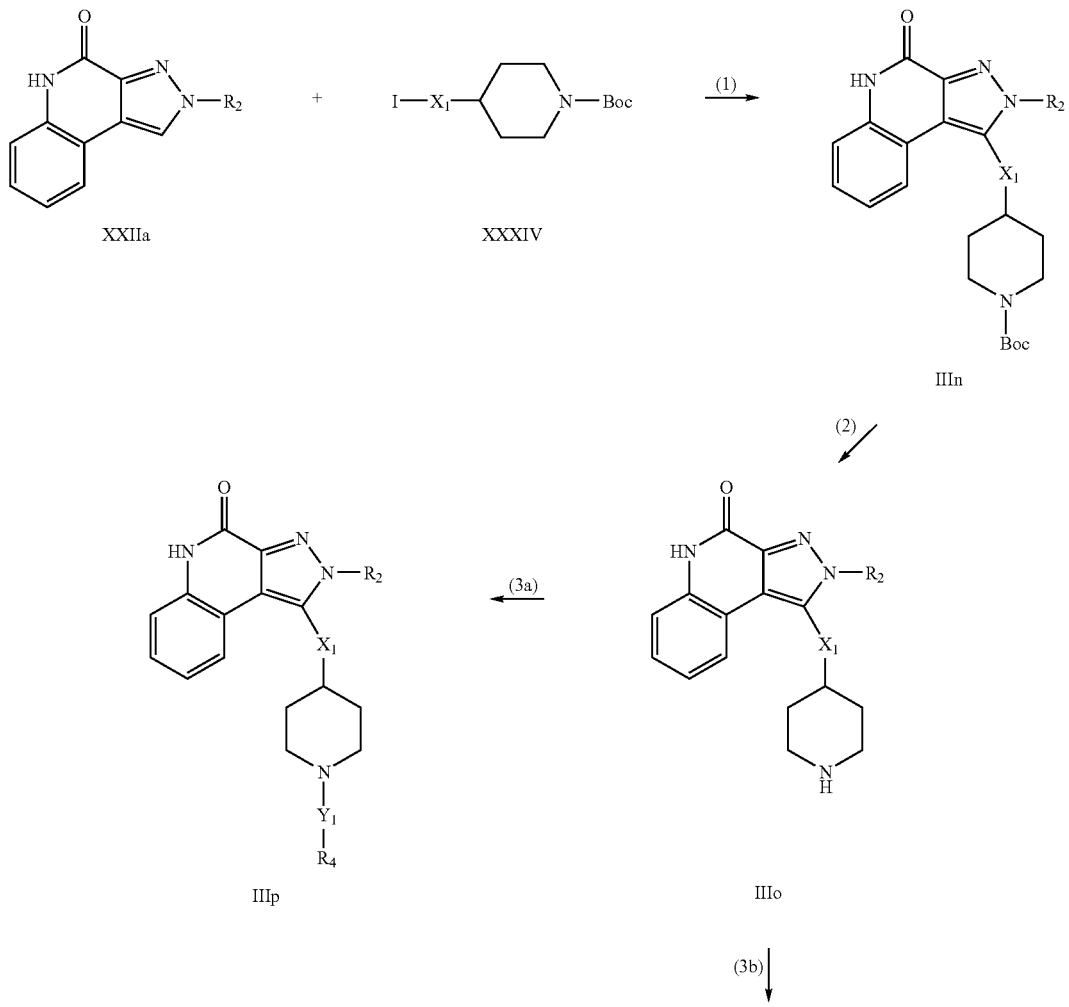

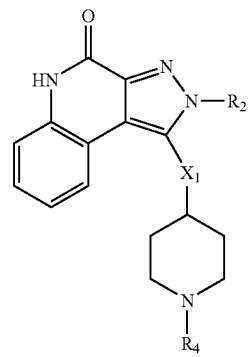

IIIq

For some embodiments, compounds of the invention can be prepared according to Reaction Scheme VII where $R_2$, $R_4$, $Y_1$, and Boc are as defined above.

In step (1) of Reaction Scheme VII, ethyl 1H-indol-2-ylacetate is reacted with ethyl chlorooxoacetate to provide ethyl (2-ethoxycarbonylmethyl-1H-indol-3-yl)oxoacetate. The reaction can be carried out using the general method described in step (1) of Reaction Scheme I. Ethyl 1H-indol-2-ylacetate is known.

In step (2) of Reaction Scheme VII, ethyl (2-ethoxycarbonylmethyl-1H-indol-3-yl)oxoacetate is rearranged to provide a pyrazolo[3,4-c]quinoline of Formula IIIr, a subgenus of Formula III. The reaction can be carried out using the general method described in step (2) of Reaction Scheme I.

In step (3) of Reaction Scheme VII, the ester group on a pyrazolo[3,4-c]quinoline of Formula IIIr is hydrolyzed to provide a pyrazolo[3,4-c]quinoline of Formula IIIs, a subgenus of Formula III. The reaction can be carried out by treating a solution of a compound of Formula IIIr in ethanol with a base such as aqueous sodium hydroxide. The reaction can be carried out at ambient temperature, In step (4) of Reaction Scheme VII, a pyrazolo[3,4-c]quinoline of Formula IIIs is coupled with N-Boc piperazine to provide a pyrazolo[3,4-c]quinoline of Formula IIIt, a subgenus of Formula III. The reaction can be carried out by treating a mixture of a compound of Formula IIIs and N-Boc piperazine in a suitable solvent such as DMF with N-(3-dimethylaminopropyl)-N'-ethylcarbodiimide hydrochloride and 1-hydroxybenzotriazole. The reaction can be carried out at ambient temperature.

In step (5) of Reaction Scheme VII, the Boc group on a pyrazolo[3,4-c]quinoline of Formula IIIt is removed to provide a pyrazolo[3,4-c]quinoline of Formula IIIu, a subgenus of Formula III. The reaction can be carried out by combining a compound of Formula IIIt with ethanol and hydrochloric acid and heating the resulting mixture at an elevated temperature such as 60° C.

In step (6a) of Reaction Scheme VII, a pyrazolo[3,4-c]quinoline of Formula IIIu is converted into an amide, sulfonamide, sulfamide, or urea of Formula IIIv, a subgenus of Formula III using conventional methods as described in step (3a) of Reaction Scheme VI.

In step (6b) of Reaction Scheme VII, a pyrazolo[3,4-c]quinoline of Formula IIIu undergoes reductive alkylation to provide a pyrazolo[3,4-c]quinoline of Formula IIIw, a subgenus of Formula III. The alkylation can be carried out as described in step (3b) of Reaction Scheme VI.

Reaction Scheme VII

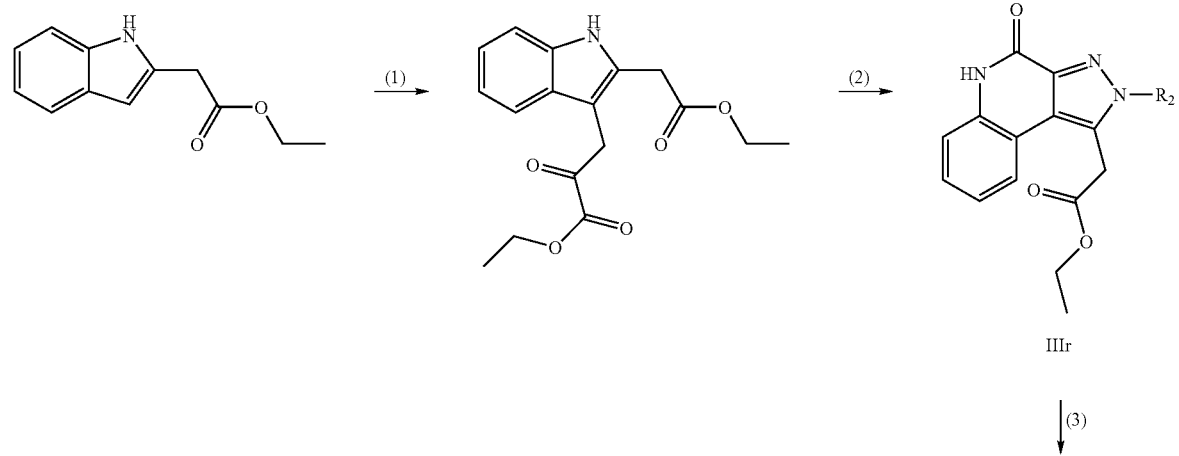

IIIr (3)

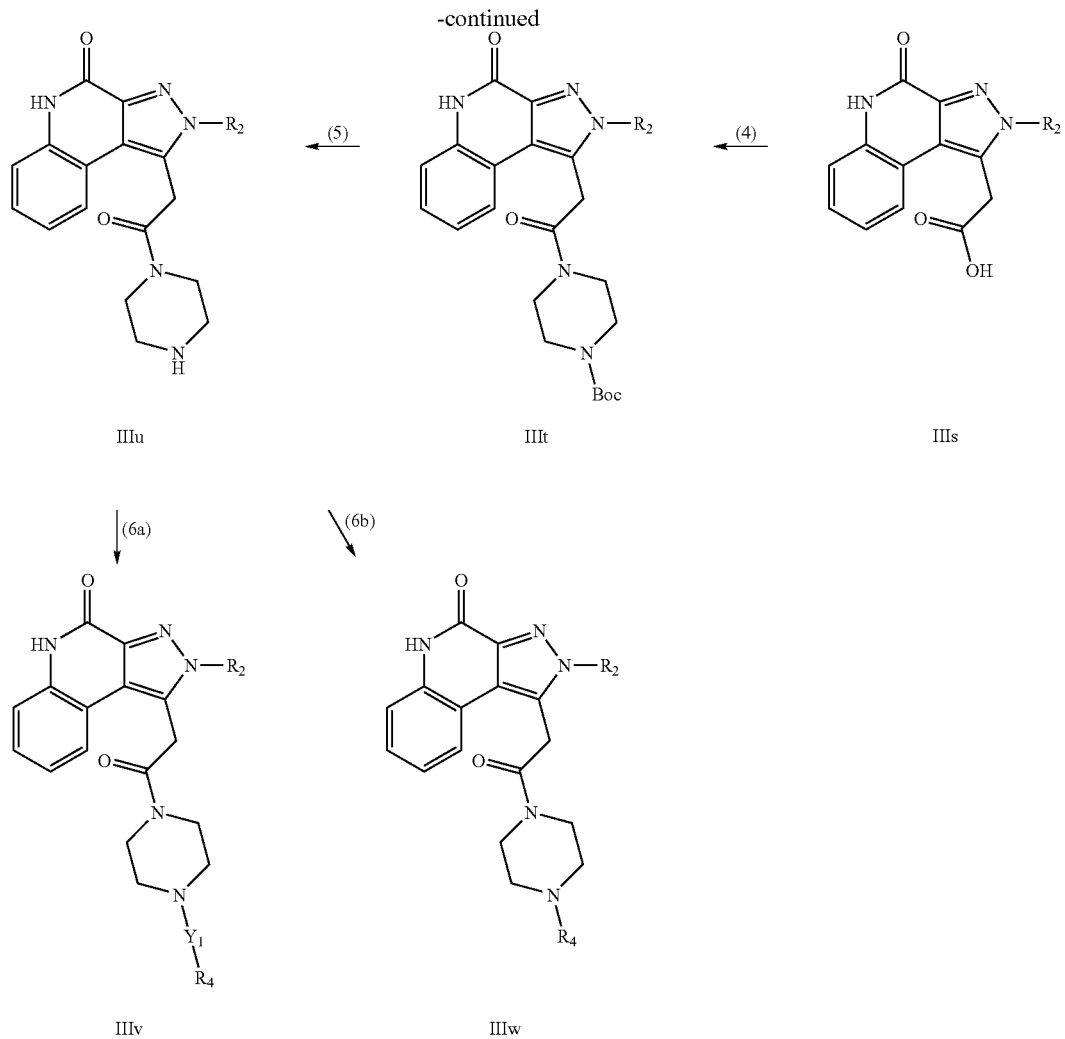

For some embodiments, compounds of the invention can be prepared using the synthetic methods described in the EXAMPLES below.

Pharmaceutical Compositions and Biological Activity

Pharmaceutical compositions of the invention contain a therapeutically effective amount of a compound or salt of the invention as described above in combination with a pharmaceutically acceptable carrier.

The terms "a therapeutically effective amount" and "effective amount" mean an amount of the compound or salt sufficient to induce a therapeutic or prophylactic effect, such as cytokine inhibition and immunomodulation. The exact amount of active compound or salt used in a pharmaceutical composition of the invention will vary according to factors known to those of skill in the art, such as the physical and chemical nature of the compound or salt, the nature of the carrier, and the intended dosing regimen.

In some embodiments, the compositions of the invention will contain sufficient active ingredient or prodrug to provide a dose of about 100 nanograms per kilogram (ng/kg) to about 50 milligrams per kilogram (mg/kg), preferably about 10 micrograms per kilogram (μg/kg) to about 5 mg/kg, of the compound or salt to the subject.

In other embodiments, the compositions of the invention will contain sufficient active ingredient or prodrug to provide a dose of, for example, from about 0.01 mg/m$^2$ to about 5.0 mg/m$^2$, computed according to the Dubois method, in which the body surface area of a subject (m$^2$) is computed using the subject's body weight: m$^2$=(wt kg$^{0.425}$×height cm$^{0.725}$)× 0.007184, although in some embodiments the methods may be performed by administering a compound or salt or composition in a dose outside this range. In some of these embodiments, the method includes administering sufficient compound to provide a dose of from about 0.1 mg/m$^2$ to about 2.0 mg/m$^2$ to the subject, for example, a dose of from about 0.4 mg/m$^2$ to about 1.2 mg/m$^2$.

A variety of dosage forms may be used, such as oral preparations in the forms of tablets, lozenges, capsules, fine granules, granules, powders, syrups, dry syrups, or parenteral preparations or formulations, for example in the forms of injections, suppositories, eye drops, eye ointments, ear drops, nasal drops, and inhalations such as aerosol formulations, or dermal preparations, for example, creams, ointments, transdermal patches, transmucosal patches and the like. These dosage forms can be prepared with conventional pharmaceutically acceptable carriers and additives using conventional methods, which generally include the step of bringing the active ingredient into association with the carrier.

The compounds or salts of the invention can be administered as the single therapeutic agent in the treatment regimen, or the compounds or salts of the invention may be administered in combination with one another or with other active agents, including additional immune response modifiers, antivirals, antibiotics, antibodies, proteins, peptides, oligonucleotides, etc.

Compounds or salts of the invention can inhibit the production of certain cytokines in experiments performed according to the tests set forth below. These results indicate that the compounds or salts are useful as immune response modifiers that can modulate the immune response in a number of different ways, rendering them useful in the treatment of a variety of disorders.

Cytokines whose production can be inhibited by the administration of compounds or salts of the invention include tumor necrosis factor-α (TNF-α) and IL-1. Among other effects, inhibition of TNF-α production can provide prophylaxis or therapeutic treatment of TNF-α mediated diseases in animals, making the compounds or salt useful in the treatment of, for example, autoimmune diseases. Accordingly, the invention provides a method of inhibiting TNF-α biosynthesis in an animal comprising administering an effective amount of a compound or salt or composition of the invention to the animal. The animal to which the compound or salt or composition is administered for inhibition of TNF-α biosynthesis may have a disease as described infra, for example an autoimmune disease, and administration of the compound or salt may provide therapeutic treatment. Alternatively, the compound or salt or composition may be administered to the animal prior to the animal acquiring the disease so that administration of the compound or salt may provide a prophylactic treatment.

Whether for prophylaxis or therapeutic treatment of a disease, and whether for effecting innate or acquired immunity, the compound or salt or composition may be administered alone or in combination with one or more active components as in, for example, a vaccine adjuvant. When administered with other components, the compound or salt and other component or components may be administered separately; together but independently such as in a solution; or together and associated with one another such as (a) covalently linked or (b) non-covalently associated, e.g., in a colloidal suspension.

Conditions for which IRMs identified herein may be used as treatments include, but are not limited to:

(a) chronic inflammatory diseases such as, for example, rheumatic arthritis and osteoarthritis;

(b) various autoimmune diseases such as, for example, autoimmune hemic diseases (e.g., hemolytic anemia, anaplastic anemia, idiopathic thrombocythemis), autoimmune intestinal diseases (e.g., ulcerative colitis, Crohn's disease), autoimmune comeitis (e.g., keratoconjunctivitis sicca, spring catarrh), endocrine opthalmopathy, Graves disease, sarcoid granuloma, multiple sclerosis, systemic erythematodes, multiple chondritis, pachydermia, active chronic hepatitis, myasthena gravis, psoriasis, interstitial pulmonary fibrosis, and the like; and (c) various conditions including allergic rhinitis, atopic dermatitis, contact dermatitis, asthma, sepsis, septic shock, diabetes, cancerous cachexia, HIV-infectious cachexia, and the like.

Thus, therapeutic or prophylactic treatment of one or more of the above diseases or types of diseases by inhibiting cytokine biosynthesis in an animal, can be provided by administering a therapeutically effective amount of a compound or salt of the invention to the animal.

An amount of a compound or salt effective to inhibit cytokine biosynthesis is an amount sufficient to cause one or more cell types, such as monocytes, macrophages, dendritic cells and B-cells to produce an amount of one or more cytokines such as, for example, TNF-α or IL-1 that is decreased (inhibited) over a level of such cytokines in the absence of the compound or salt. The precise amount will vary according to factors known in the art but is expected to be a dose of about 100 ng/kg to about 50 mg/kg, preferably about 10 μg/kg to about 5 mg/kg. In other embodiments, the amount is expected to be a dose of, for example, from about 0.01 mg/m$^2$ to about 5.0 mg/m$^2$, (computed according to the Dubois method as described above) although in some embodiments the inhibition of cytokine biosynthesis may be performed by administering a compound or salt in a dose outside this range.

Objects and advantages of this invention are further illustrated by the following examples, but the particular materials and amounts thereof recited in these examples, as well as other conditions and details, should not be construed to unduly limit this invention.

EXAMPLES

In the examples below automated flash chromatography on silica gel was carried out using a COMBIFLASH system (an automated high-performance flash purification product available from Teledyne Isco, Inc., Lincoln, Nebr., USA), a HORIZON HPFC system (an automated high-performance flash purification product available from Biotage, Inc, Charlottesville, Va., USA) or an INTELLIFLASH Flash Chromatography System (an automated flash purification system available from AnaLogix, Inc, Burlington, Wis., USA). The eluent used for each purification is given in the example. In some chromatographic separations, the solvent mixture 80/18/2 v/v/v chloroform/methanol/concentrated ammonium hydroxide (CMA) was used as the polar component of the eluent. In these separations, CMA was mixed with chloroform in the indicated ratio.

Example 1

4-Chloro-1-methyl-2-propyl-2H-pyrazolo[3,4-c]quinoline

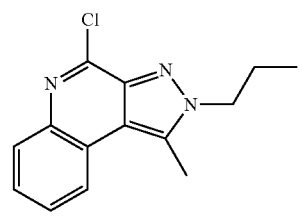

Part A

A solution of ethyl chlorooxoacetate (22.53 g, 0.165 mol) in diethyl ether (100 mL) was added over a period of 15 minutes to a cooled (0° C.) solution of 2-methylindole (19.7 g, 0.15 mol) and pyridine (14.2 g, 0.18 mol) in diethyl ether (200 mL). The reaction was stirred for two hours at 0° C. under a nitrogen atmosphere. Most of the diethyl ether had evaporated by the end of the two-hour reaction time, and a solid was present. Water (100 mL) was added, and the solid was isolated by filtration and washed with 1:1 diethyl ether/hexane. The solid (27.9 g) was then dissolved in boiling toluene (250 mL) and recrystallized upon cooling to 6° C. The crystals were isolated by filtration, washed with toluene, dried for two hours on the vacuum filter funnel, triturated with water at 75° C. for five minutes, isolated by filtration, and dried for three hours on the filter funnel to provide 17.8 g of ethyl (2-methyl-1H-indol-3-yl)(oxo)acetate as a rust-colored powder.

Part B

Ethyl (2-methyl-1H-indol-3-yl)(oxo)acetate (6.94 g, 30.0 mmol) and propylhydrazine oxalate (10.8 g, 66.0 mmol) were added to a solution of acetyl chloride (5.18 g, 66.0 mmol) in acetic acid (5 mL) and ethanol (150 mL), and the reaction was heated at reflux under nitrogen for 42.5 hours. The ethanol was removed under reduced pressure, and 2 M aqueous sodium carbonate was added. The mixture was stirred, and the resulting solid was isolated by filtration, washed with water, and dried for 90 minutes on the vacuum filter funnel to provide a dark semi-solid. The crude product was stirred with tert-butyl methyl ether (50 mL) and isolated by filtration, washed with tert-butyl methyl ether, and dried on the vacuum filter funnel to provide 6.10 g of an orange solid, which was stirred with boiling acetonitrile (50 mL), isolated by filtration, and purified by automated flash chromatography to provide 5.11 g of 1-methyl-2-propyl-2H-pyrazolo[3,4-c]quinolin-4-ol as a white solid.

Part C

A solution of 1-methyl-2-propyl-2H-pyrazolo[3,4-c]quinolin-4-ol (5.11 g, 21.2 mmol) in phosphorus oxychloride (50 mL) was heated at reflux for 30 minutes, allowed to cool to room temperature, and stirred for two days. The reaction mixture was poured into ice water (500 mL) with stirring, and concentrated ammonium hydroxide (169 mL) and ice were added. A solid was present and was isolated by filtration, washed with water, and purified by automated flash chromatography (eluting with 5% to 25% CMA in chloroform). The resulting orange solid (5.5 g) was recrystallized from acetonitrile (25 mL). The crystals were washed with acetonitrile and dried for five hours to provide 3.85 g of 4-chloro-1-methyl-2-propyl-2H-pyrazolo[3,4-c]quinoline as a white solid, mp 145-147° C. Anal. Calcd for $C_{14}H_{14}N_3Cl$: C, 64.74; H, 5.43; N, 16.18. Found: C, 64.50; H, 5.64; N, 16.20.

Example 2

2-Ethyl-4-oxo-4,5-dihydro-2H-pyrazolo[3,4-c]quinoline-1-carbaldehyde

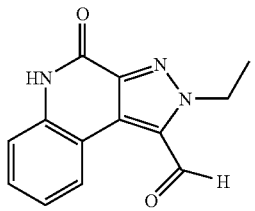

Part A

Acetyl chloride (0.7 mL, 9.8 mmol), acetic acid (1 mL), and ethylhydrazine (1.5 g, 9.8 mmol) were added sequentially to a suspension of methyl (1H-indol-3-yl)glyoxalate (1.0 g, 4.9 mmol) in ethanol (25 mL). The reaction mixture was heated at reflux for 18 hours. The reaction mixture was cooled to ambient temperature and then concentrated under reduced pressure. The residue was combined with acetonitrile. A pink solid was isolated by filtration and then purified by automated flash chromatography (Biotage, eluted with a gradient of 0-30% CMA in chloroform) to provide a white solid. This material was recrystallized from acetonitrile to provide 360 mg of 2-ethyl-2,5-dihydro-4H-pyrazolo[3,4-c]quinolin-4-one as white crystals, mp>250° C. MS (APCI) m/z 214 (M+H)$^+$; Anal. calcd for $C_{12}H_{11}N_3O$: C, 67.59; H, 5.20; N, 19.71. Found: C, 67.52; H, 5.14; N, 19.90.

Part B

Under a nitrogen atmosphere, a mixture of 2-ethyl-2,5-dihydro-4H-pyrazolo[3,4-c]quinolin-4-one (10 g, 46.8 mmol), N,N,N',N'-tetramethylethylenediamine (31 mL), and tetrahydrofuran (520 mL) was chilled to 0° C. A solution of n-butyllithium in hexanes (56 mL of 2.5 M) was added dropwise. After the addition was complete the reaction mixture was stirred for 5 minutes and then N,N-dimethylformamide (DMF, 72 mL) was added dropwise. The reaction mixture was warmed to ambient temperature and stirred for 1 hour. 1 N hydrochloric acid was added and the reaction mixture was stirred for 1 hour. The reaction mixture was concentrated under reduced pressure to about half the original volume and then diluted with water and extracted with dichloromethane. The combined extracts were dried over sodium sulfate, filtered, and then concentrated under reduced pressure to provide a dark yellow oil. The oil was combined with acetonitrile and stirred for 20 minutes. A bright yellow solid was isolated by filtration to provide 4 g of 2-ethyl-4-oxo-4,5-dihydro-2H-pyrazolo[3,4-c]quinoline-1-carbaldehyde as a yellow powder. MS (APCI) m/z 242 (M+H)$^+$; $^1$H NMR (300 MHz, DMSO-$d_6$) δ 11.67 (s, 1H), 10.52 (s, 1H), 8.72 (d, J=8.1 Hz, 1H), 7.49 (dt, J=1.4 and 7.3 Hz, 1H), 7.40 (dd, J1.4 and 8.3 Hz, 1H), 7.25 (dt, J=1.4 and 7.3 Hz, 1H), 4.82 (q, J=7.2 Hz, 2H), 1.52 (t, J=7.2 Hz, 3H). An additional 3 g of material was isolated from the mother liquor.

Example 3

4-Chloro-2-ethyl-2H-pyrazolo[3,4-c]quinoline-1-carbaldehyde

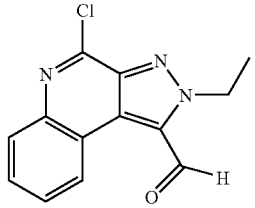

2-Ethyl-4-oxo-4,5-dihydro-2H-pyrazolo[3,4-c]quinoline-1-carbaldehyde (1 g) was combined with phosphorus oxychloride (10 mL) and heated at 100° C. for 30 minutes. The reaction mixture was cooled to ambient temperature, poured into a mixture of ammonium hydroxide and ice, and then stirred for 20 minutes. A solid was isolated by filtration and air dried to provide 4-chloro-2-ethyl-2H-pyrazolo[3,4-c]quinoline-1-carbaldehyde as a white powder. MS (APCI) m/z 260 (M+H)$^+$.

Example 4

(4-Chloro-2-ethyl-2H-pyrazolo[3,4-c]quinolin-1-yl)methanol

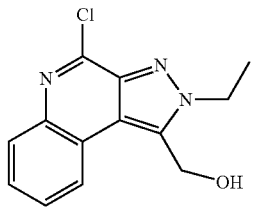

Part A

2-Ethyl-4-oxo-4,5-dihydro-2H-pyrazolo[3,4-c]quinoline-1-carbaldehyde (3.9 g) was combined with phosphorus oxychloride (32 mL) and heated at 100° C. for 30 minutes. Analysis by liquid chromatography/mass spectroscopy (LCMS) showed a 1:9 ratio of desired product to a trichloro species in which chloride had replaced the 4-hydroxy group and the aldehyde to provide a geminal dichloride group. The reaction mixture was cooled to ambient temperature, poured into a mixture of ammonium hydroxide and ice, and then stirred for 20 minutes. A solid was isolated by filtration and air dried to provide a tan solid.

Part B

Sodium borohydride (217 mg) was added in portions over a period of 30 minutes to a suspension of material from Part A (500 mg) in tetrahydrofuran (10 mL). After 1 hour, analysis by LCMS indicated a 1:1 ratio of the desired alcohol to the trichloro species. The reaction mixture was stirred overnight at which time analysis by LCMS indicated a 3:1 ratio of the desired alcohol to the trichloro species. A white solid was isolated by filtration to provide 200 mg of (4-chloro-2-ethyl-2H-pyrazolo[3,4-c]quinolin-1-yl)methanol as a white powder. MS (APCI) m/z 262 (M+H)$^+$; $^1$H NMR (300 MHz, DMSO-d$_6$) δ 8.40 (dd, J=1.9 and 7.8 Hz, 1H), 7.97 (dd, J=2.1 and 7.4 Hz, 1H), 7.62-7.72 (m, 2H), 5.74 (s, 1H), 5.13 (s, 2H), 4.63 (q, J=7.2 Hz, 2H), 1.53 (t, J=7.2 Hz, 3H).

Example 5

(2-Ethyl-4-methoxy-2H-pyrazolo[3,4-c]quinolin-1-yl)methanol

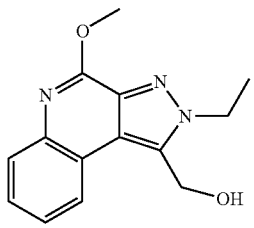

Part A

Sodium borohydride (465 mg) was added in portions over a period of 30 minutes to a suspension of 2-ethyl-4-oxo-4,5-dihydro-2H-pyrazolo[3,4-c]quinoline-1-carbaldehyde (4.1 mmol) in methanol (20 mL). After 1 hour analysis by LCMS showed that there was no starting material left; only the desired alcohol was observed. The reaction mixture was concentrated under reduced pressure and the residue (product, boron salts, sodium methoxide) was carried on to the next step.

Part B

The material from Part A was combined in a pressure vessel with a solution of ammonia in methanol (100 mL of 7 N). The vessel was sealed and heated at 150° C. for 20 hours. The reaction mixture was absorbed onto silica and then purified by automated flash chromatography (Analogix, eluted with a gradient of 0-30% CMA in chloroform) to provide a white solid. This material was recrystallized from acetonitrile to provide 170 mg of (2-ethyl-4-methoxy-2H-pyrazolo[3,4-c]quinolin-1-yl)methanol as white crystals, mp 219-220° C. Anal. calcd for C$_{14}$H$_{15}$N$_3$O$_2$: C, 65.36; H, 5.88; N, 16.33. Found: C, 65.22; H, 5.85; N, 16.57.

Example 6

2-Phenyl-1-(2-piperidin-4-ylethyl)-2,5-dihydro-4H-pyrazolo[3,4-c]quinolin-4-one

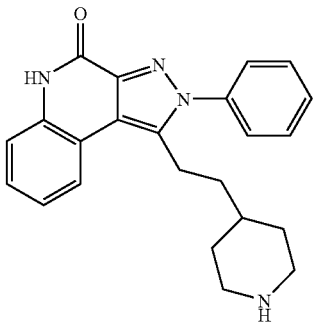

Part A

Pyridine (40 mL, 492 mmol) was added in a single portion to a chilled solution (0° C.) of indole (48 g, 410 mmol) in diethyl ether (820 mL). Ethyl chlorooxoacetate (50 mL, 451 mmol) was added dropwise. The resulting suspension was allowed to warm to ambient temperature over a period of 20 hours. The solid was isolated by filtration and washed with diethyl ether. The solid was combined with water (1 L), stirred for 1 hour, and then isolated by filtration to provide 75 g of ethyl (1H-indol-3-yl)(oxo)acetate.

Part B

Acetyl chloride (26 mL, 364 mmol), acetic acid (30 mL), and phenylhydrazine (36 mL, 364 mmol) were added sequentially to a suspension of material from Part A (37 g, 182 mmol) in ethanol (910 mL). The reaction mixture was heated at reflux for 18 hours. A white solid was isolated by filtration and washed with ethanol. Analysis of this material by $^1$H NMR indicated that this material was a 1:1 mixture of starting material and product. The solid was triturated with refluxing acetonitrile to provide 2-phenyl-2,5-dihydro-4H-pyrazolo[3,4-c]quinolin-4-one as a white powder, mp>250° C. MS (APCI) m/z 262 (M+H)$^+$; Anal. calcd for C$_{16}$H$_{11}$N$_3$O: C, 73.55; H, 4.24; N, 16.08. Found: C, 73.44; H, 4.21; N, 16.20.

Part C

To a mixture of 2-piperidin-4-ylethanol (10 g, 77 mmol) and dichloromethane (190 mL) at 0° C. was added di-(tert-butyl)dicarbonate (17.7 g, 81.3 mmol). The reaction was warmed to ambient temperature and stirred 4 hours. The reaction was washed with water, 10% aqueous potassium hydrosulfate, and brine. The organic layer was dried over sodium sulfate, filtered, and concentrated to 20 g of tert-butyl 4-(2-hydroxyethyl)piperidine-1-carboxylate as a clear oil. This clear oil was dissolved in dichloromethane (90 mL) and added dropwise over 20 minutes at 0° C. to a suspension of triphenylphosphine (20 g, 77 mmol), imidazole (5.3 g, 77 mmol), iodine (22 g, 85 mmol), and dichloromethane (300 mL). The reaction was stirred 5 hours at ambient temperature. The reaction was filtered and the filtrate was quenched with sodium bisulfite and diluted with water. The layers were separated. The aqueous layer was extracted with additional dichloromethane. The combined organic layers were dried over sodium sulfate, filtered, and concentrated to a brown oil. This oil was purified by chromatography (SiO$_2$, 20% hexanes/ethyl acetate) to obtain 22 g of tert-butyl 4-(2-iodoethyl)piperidine-1-carboxylate as a colorless oil.

Part D

Under a nitrogen atmosphere, a mixture of 2-phenyl-2,5-dihydro-4H-pyrazolo[3,4-c]quinoline-one (1.76 g, 6.76 mmol), N,N,N',N'-tetramethylethylenediamine (4.5 mL), and tetrahydrofuran (75 mL) was chilled to 0° C. A solution of n-butyllithium in hexanes (8.1 mL of 2.5 M) was added dropwise. After the addition was complete the reaction mixture was stirred for 5 minutes at 0° C. and then cooled to –78° C. To the cooled solution was added tert-butyl 4-(2-iodoethyl) piperidine-1-carboxylate (3.0 g, 8.8 mmol). The reaction mixture was warmed to ambient temperature and stirred for 30 minutes before quenching with saturated aqueous ammonium chloride. The aqueous layer was extracted with chloroform. The combined organic extracts were dried over sodium sulfate, filtered, and concentrated under reduced pressure to afford a yellow oil, The yellow oil was stirred in acetonitrile and filtered to provide 1.4 g (75% pure) of tert-butyl 4-[2-(4-oxo-2-phenyl-4,5-dihydro-2H-pyrazolo[3,4-c]quinolin-1-yl)ethyl]piperidine-1-carboxylate as a tan solid.

Part E

A mixture of tert-butyl 4-[2-(4-oxo-2-phenyl-4,5-dihydro-2H-pyrazolo[3,4-c]quinolin-1-yl)ethyl]piperidine-1-carboxylate (800 mg, 2.14 mmol) and concentrated hydrochloric acid (10 mL) was stirred at ambient temperature for 30 min. The reaction was poured over ice and the pH of the ice slurry was brought to 12 with 50% aqueous sodium hydroxide. After warming the reaction mixture to ambient temperature, the aqueous layer was extracted with chloroform. The combined organic extracts were dried over sodium sulfate, filtered, and concentrated under reduced pressure to afford crude 2-phenyl-1-(2-piperidin-4-ylethyl)-2,5-dihydro-4H-pyrazolo[3,4-c]quinolin-4-one as a yellow oily solid. The yellow oily solid was combined with additional 2-phenyl-1-(2-piperidin-4-ylethyl)-2,5-dihydro-4H-pyrazolo[3,4-c]quinolin-4-one (100 mg) and combined with phosphorous oxylchloride (12 mL). The resulting suspension was heated to 90° C. and stirred at this temperature for 5 minutes. The resulting reaction mixture was poured into a 1:1 mixture of saturated aqueous ammonium hydroxide and ice (200 mL). A solid formed that was isolated by filtration. The filtrate was extracted with dichloromethane. The isolated solid was dissolved in dichloromethane and methanol, combined with the organic extracts, dried over sodium sulfate, filtered, and concentrated under reduced pressure to afford a yellow oily solid. The yellow oily solid was purified by automated flash chromatography (AnaLogix, eluted with a gradient of 0-50% CMA in chloroform) to provide material that was stirred in acetonitrile and filtered to provide 130 mg of 2-phenyl-1-(2-piperidin-4-ylethyl)-2,5-dihydro-4H-pyrazolo[3,4-c]quinolin-4-one as a white powder, mp 250-252° C. MS (APCI) m/z 373 (M+H)$^+$; Anal. calcd for $C_{23}H_{24}N_4O.0.75H_2O$: C, 71.57; H, 6.66; N, 14.57. Found: C, 71.75; H, 6.58; N, 14.13.

Example 7

4-Chloro-2-phenyl-1-(2-piperidin-4-ylethyl)-2H-pyrazolo[3,4-c]quinoline

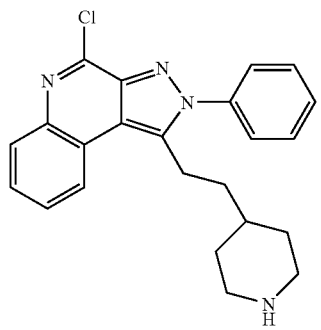

Thionyl chloride (1.0 mL) and DMF (1.0 mL) were combined and added dropwise to a mixture of 2-phenyl-1-(2-piperidin-4-ylethyl)-2,5-dihydro-4H-pyrazolo[3,4-c]quinolin-4-one (200 mg, 0.537 mmol) and dichloromethane (10 mL) at 0° C. The resulting suspension was stirred 5 minutes at 0° C. before warming to ambient temperature and stirring 55 minutes. The suspension was concentrated under reduced pressure to afford a light yellow oil that was stirred in acetonitrile and filtered to obtain a white solid. The solid was combined with additional acetonitrile and concentrated under reduced pressure to afford 100 mg of 4-chloro-2-phenyl-1-(2-piperidin-4-ylethyl)-2H-pyrazolo[3,4-c]quinoline.HCl as a white powder, mp 194° C. MS (APCI) m/z 391 (M+H)$^+$; Anal. calcd for $C_{23}H_{23}ClN_4.1.0H_2O.1.0HCl$: C, 62.02; H, 5.88; N, 12.58. Found: C, 61.91; H, 5.67; N, 12.48.

Example 8 tert-Butyl 4-[2-hydroxy-2-(4-oxo-2-phenyl-4,5-dihydro-2H-pyrazolo[3,4-c]quinolin-1-yl)ethyl]piperidine-1-carboxylate

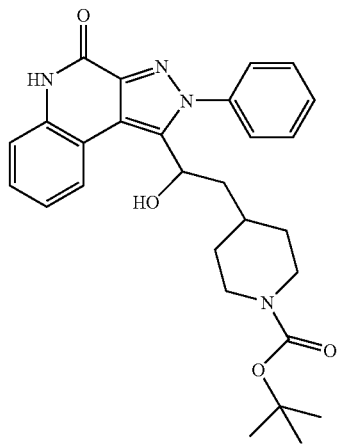

Part A

To a mixture of tert-butyl 4-(2-hydroxyethyl)piperidine-1-carboxylate (3.4 g, 15 mmol) and dichloromethane (18 mL) at 0° C. was added triethyl amine (10 mL), dimethyl sulfoxide (18 mL), and sulfur trioxide pyridine (5.9 g, 37 mmol). The reaction was stirred 2 hours before diluting with ethyl acetate and saturated aqueous ammonium chloride. The layers were separated and the aqueous layer was extracted with additional ethyl acetate. The combined organic layers were washed with brine, dried over sodium sulfate, filtered, and concentrated to 3.3 g of tert-butyl 4-(2-oxoethyl)piperidine-1-carboxylate as a colorless oil.

Part B

2-Phenyl-2,5-dihydro-4H-pyrazolo[3,4-c]quinoline-one (574 mg, 2.20 mmol) was combined with N,N,N'N'-tetramethylethylenediamine (1.5 mL), and tetrahydrofuran (24 mL) under an atmosphere of nitrogen. The mixture was chilled to 0° C. A solution of n-butyllithium in hexanes (2.0 mL of 2.5 M) was added dropwise. After the addition was complete the reaction mixture was stirred for 5 minutes at 0° C. and then cooled to –78° C. To the cooled solution was added tert-butyl 4-(2-oxoethyl)piperidine-1-carboxylate (1.0 g, 4.4 mmol). The reaction mixture was warmed to ambient temperature and stirred for 30 minutes before quenching with saturated aqueous ammonium chloride. The aqueous layer was extracted with chloroform. The combined organic extracts were dried over sodium sulfate, filtered, and concentrated under reduced pressure to afford a yellow oil. The oil was purified by automated flash chromatography (AnaLogix, eluted with a gradient of 0-30% CMA in chloroform) to provide an oily solid. The oily solid was stirred in acetonitrile and filtered to provide 450 mg of tert-butyl 4-[2-hydroxy-2-(4-oxo-2-phenyl-4,5-dihydro-2H-pyrazolo[3,4-c]quinolin-1-yl)ethyl]piperidine-1-carboxylate as a white solid, mp 253-254° C. MS (APCI) m/z 489 (M+H)+; Anal. calcd for $C_{28}H_{32}N_4O_4$: C, 68.83; H, 6.60; N, 11.47. Found: C, 68.49; H, 6.83; N, 11.67.

Example 9

1-(1-Hydroxy-2-piperidin-4-ylethyl)-2-phenyl-2,5-dihydro-4H-pyrazolo[3,4-c]quinolin-4-one

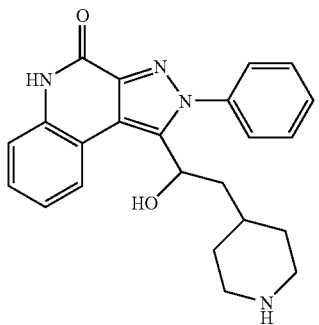

Tert-butyl 4-[2-hydroxy-2-(4-oxo-2-phenyl-4,5-dihydro-2H-pyrazolo[3,4-c]quinolin-1-yl)ethyl]piperidine-1-carboxylate (100 mg, 0.2 mmol) was combined with concentrated hydrochloric acid (1 mL) and stirred at ambient temperature for 30 min. The reaction was poured over ice and the pH of the ice slurry was brought to 12 with 50% aqueous sodium hydroxide. The aqueous layer was extracted with dichloromethane. The combined organic extracts were dried over sodium sulfate, filtered, and concentrated under reduced pressure. The resulting material was purified by automated flash chromatography (AnaLogix, eluted with a gradient of 0-60% CMA in chloroform) to provide an oily solid. The oily solid was stirred in acetonitrile. A solid was isolated by filtration to provide 40 mg of 1-(1-hydroxy-2-piperidin-4-yl-ethyl)-2-phenyl-2,5-dihydro-4H-pyrazolo[3,4-c]quinolin-4-one as a tan powder, mp 258-261° C. MS (APCI) m/z 389 (M+H)+; Anal. calcd for $C_{23}H_{24}N_4O_2 \cdot 0.6H_2O$: C, 69.19; H, 6.36; N, 14.03. Found: C, 69.02; H, 6.23; N, 14.11.

Example 10

1-(2-Cyclohexyl-1-hydroxyethyl)-2-phenyl-2,5-dihydro-4H-pyrazolo[3,4-c]quinolin-4-one

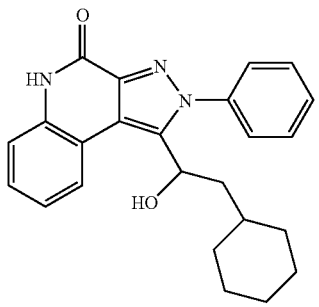

Part A

To a mixture of cyclohexylmethanol (5.0 mL, 36 mmol) and dichloromethane (27 mL) at 0° C. was added triethyl amine (27 mL), dimethyl sulfoxide (27 mL), and sulfur trioxide pyridine (8.5 g, 54 mmol). The reaction was stirred 2 hours before diluting with ethyl acetate and saturated aqueous ammonium chloride. The layers were separated and the aqueous layer was extracted with additional ethyl acetate. The combined organic layers were washed with brine, dried over sodium sulfate, filtered, and concentrated to 12 g of cyclohexylacetaldehyde as a yellow oil.

Part B

2-Phenyl-2,5-dihydro-4H-pyrazolo[3,4-c]quinoline-one (4.7 g, 17.9 mmol) was combined with N,N,N',N'-tetramethylethylenediamine (12 mL), and tetrahydrofuran (200 mL) under an atmosphere of nitrogen. The mixture was chilled to 0° C. A solution of n-butyllithium in hexanes (19 mL of 2.5 M) was added dropwise. After the addition was complete the reaction mixture was stirred for 5 minutes at 0° C. and then cooled to −78° C. To the cooled solution was added cyclohexylacetaldehyde (12 g, 35 mmol). The reaction mixture was warmed to ambient temperature and stirred for 30 minutes before quenching with saturated aqueous ammonium chloride. The aqueous layer was extracted with chloroform. The combined organic extracts were dried over sodium sulfate, filtered, and concentrated under reduced pressure to afford a yellow oily solid. The oily solid was purified by automated flash chromatography (AnaLogix, eluted with a gradient of 0-30% CMA in chloroform) to provide a yellow solid. The solid was boiled in acetonitrile and filtered. The filtrate was adsorbed onto silica gel and purified by automated flash chromatography (AnaLogix, eluted with a gradient of 0-20% CMA in chloroform) to provide a white foam. The foam was stirred in acetonitrile and filtered to provide 213 mg of 1-(2-cyclohexyl-1-hydroxyethyl)-2-phenyl-2,5-dihydro-4H-pyrazolo[3,4-c]quinolin-4-one as a white powder, mp 254-259° C. MS (APCI) m/z 388 (M+H)+; Anal. calcd for $C_{24}H_{25}N_3O_2$: C, 74.39; H, 6.50; N, 10.84. Found: C, 74.40; H, 6.37; N, 10.89.

Example 11

1-Methyl-2-phenyl-2,5-dihydro-4H-pyrazolo[3,4-c]quinolin-4-one

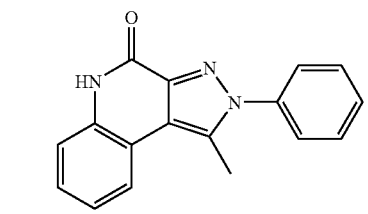

Acetyl chloride (11.0 mL, 152 mmol), acetic acid (13 mL), and phenylhydrazine (15 mL, 152 mmol) were added sequentially to a suspension of ethyl (2-methyl-1H-indol-3-yl)(oxo)acetate (17 g, 76 mmol) in ethanol (380 mL). The reaction mixture was heated at reflux for 18 hours. After cooling to ambient temperature a red solid was isolated by filtration. The solid was boiled in a 1:1 mixture of 0.5 M hydrochloric acid and methanol and filtered to provide 10.8 g of 1-methyl-2-phenyl-2,5-dihydro-4H-pyrazolo[3,4-c]quinolin-4-one as a tan solid, mp>250° C. MS (APCI) m/z 276 (M+H)⁺; Anal. calcd for $C_{17}H_{13}N_3O$: C, 74.17; H, 4.76; N, 15.26. Found: C, 73.95; H, 4.76; N, 15.04.

Example 12

4-Chloro-1-methyl-2-phenyl-2H-pyrazolo[3,4-c]quinoline

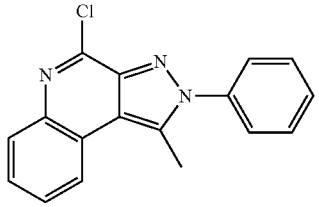

Thionyl chloride (17 mL) and DMF (17 mL) were combined and added dropwise to a mixture of 1-methyl-2-phenyl-2,5-dihydro-4H-pyrazolo[3,4-c]quinolin-4-one (9.78 g, 35.5 mmol) and dichloromethane (500 mL) at 0° C. The resulting suspension was stirred 5 minutes at 0° C. before warming to ambient temperature and stirring 2 hours. The suspension was concentrated under reduced pressure to afford a tan solid that was stirred in acetonitrile and filtered to obtain 8.8 g of 4-chloro-1-methyl-2-phenyl-2H-pyrazolo[3,4-c]quinoline as a tan solid, mp 208-209° C. MS (APCI) m/z 294 (M+H)⁺; Anal. calcd for $C_{17}H_{12}ClN_3 \cdot 0.05\ CH_2Cl_2$: C, 68.72; H, 4.09; N, 14.10. Found: C, 68.85; H, 3.95; N, 14.09.

Example 13

1-Methyl-2-phenyl-2H-pyrazolo[3,4-c]quinoline

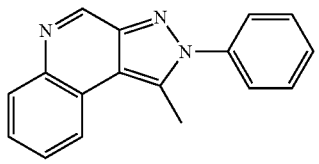

4-Chloro-1-methyl-2-phenyl-2H-pyrazolo[3,4-c]quinoline (250 mg, 0.85 mmol) was combined with ammonium formate (268 mg, 4.25 mmol), ethanol (4 mL), and palladium on carbon (10%, 25 mg). The resulting gray suspension was warmed to 60° C. and stirred at this temperature for 18 hours. The reaction was cooled to ambient temperature and filtered through CELITE filter agent. The methanol was removed under reduced pressure and the resulting material was purified by automated flash chromatography (AnaLogix, eluted with a gradient of 0-30% CMA in chloroform) to provide material that was stirred in acetonitrile. A solid was isolated by filtration to provide 40 mg of 1-methyl-2-phenyl-2H-pyrazolo[3,4-c]quinoline as a white powder, mp 128-130° C. MS (APCI) m/z 260 (M+H)⁺; Anal. calcd for $C_{17}H_{13}N_3 \cdot 0.15\ H_2O$: C, 77.93; H, 5.12; N, 16.04. Found: C, 78.09; H, 5.51; N, 16.27.

Example 14

1-Ethyl-2-phenyl-2,5-dihydro-4H-pyrazolo[3,4-c]quinolin-4-one

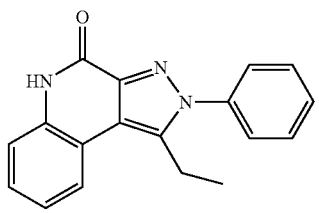

Under a nitrogen atmosphere, a mixture of 2-phenyl-2,5-dihydro-4H-pyrazolo[3,4-c]quinoline-one (3.0 g, 11.5 mmol), N,N,N'-tetramethylethylenediamine (7.7 mL), and tetrahydrofuran (128 mL) was chilled to 0° C. A solution of n-butyllithium in hexanes (12.0 mL of 2.86 M) was added dropwise. After the addition was complete the reaction mixture was stirred for 5 minutes at 0° C. and then cooled to −78° C. To the cooled solution was added iodoethane (5.3 mL, 34 mmol). The reaction mixture was warmed to ambient temperature and stirred for 30 minutes before quenching with saturated aqueous ammonium chloride. The layers were separated and the organic layer was concentrated under reduced pressure to afford a yellow oil. The yellow oil was stirred in acetonitrile and filtered to provide material that was recrystallized from methanol to provide 100 mg of 1-ethyl-2-phenyl-2,5-dihydro-4H-pyrazolo[3,4-c]quinolin-4-one as colorless needles., mp 331-334° C. MS (APCI) m/z 290 (M+H)⁺; Anal. calcd for $C_{18}H_{15}N_3O$: C, 74.72; H, 5.23; N, 14.52. Found: C, 74.51; H, 4.96; N, 14.62.

Example 15

4-Chloro-1-ethyl-2-phenyl-2H-pyrazolo[3,4-c]quinoline

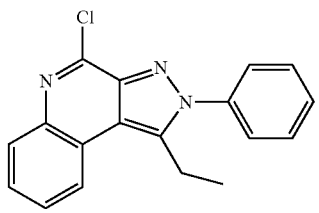

Thionyl chloride (4 mL) and DMF (4 mL) were combined and added dropwise to a mixture of 1-ethyl-2-phenyl-2,5-dihydro-4H-pyrazolo[3,4-c]quinolin-4-one (1.29 g, 4.40 mmol) and dichloromethane (80 mL) at 0° C. The resulting suspension was stirred 5 minutes at 0° C. before warming to ambient temperature and stirring 50 minutes. The suspension was concentrated under reduced pressure to afford an oily solid that was stirred in acetonitrile and filtered to obtain 450 mg of 4-chloro-1-ethyl-2-phenyl-2H-pyrazolo[3,4-c]quinoline as white crystals, mp 207-209° C. MS (APCI) m/z 308 (M+H)⁺; Anal. calcd for $C_{18}H_{14}ClN_3$: C, 70.24; H, 4.58; N, 13.65. Found: C, 69.94; H, 4.48; N, 13.54

Example 16

1-Butyl-4-chloro-2-phenyl-2H-pyrazolo[3,4-c]quinoline

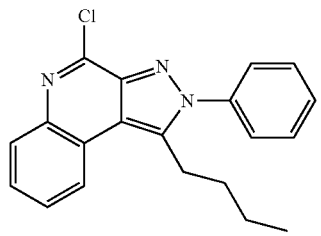

Part A

Under a nitrogen atmosphere, a mixture of 2-phenyl-2,5-dihydro-4H-pyrazolo[3,4-c]quinoline-one (3.0 g, 11.5 mmol), N,N,N'N'-tetramethylethylenediamine (7.7 mL), and tetrahydrofuran (128 mL) was chilled to 0° C. A solution of n-butyllithium in hexanes (12 mL of 2.86 M) was added dropwise. After the addition was complete the reaction mixture was stirred for 5 minutes at 0° C. and then cooled to −78° C. To the cooled solution was added iodobutane (3.9 mL, 34.5 mmol). The reaction mixture was warmed to ambient temperature and stirred for 30 minutes before quenching with saturated aqueous ammonium chloride. The aqueous layer was extracted with dichloromethane. The combined organic extracts were dried over sodium sulfate, filtered, and concentrated under reduced pressure to 100 mL of solvent. This was placed directly on a silica gel column and purified by automated flash chromatography (AnaLogix, eluted with a gradient of 0-50% CMA in chloroform) to provide 3.7 g of 1-butyl-2-phenyl-2,5-dihydro-4H-pyrazolo[3,4-c]quinolin-4-one as a 2:1 mixture of product to starting material.

Part B

Thionyl chloride (11 mL) and DMF (11 mL) were combined and added dropwise to a mixture of material obtained in Part A (3.7 g, 66% pure) and dichloromethane (200 mL) at 0° C. The resulting suspension was stirred 5 minutes at 0° C. before warming to ambient temperature and stirring 2 hours. The reaction was concentrated under reduced pressure to afford an oily solid that was stirred in acetonitrile and filtered to obtain a white solid that was recrystallized from acetonitrile to obtain 360 mg of 1-butyl-4-chloro-2-phenyl-2H-pyrazolo[3,4-c]quinoline as white crystals, mp 239-243° C. MS (APCI) m/z 336 (M+H)$^+$; Anal. calcd for $C_{20}H_{18}ClN_3$: C, 71.53; H, 5.40; N, 12.51. Found: C, 71.41; H, 5.44; N, 12.63.

Example 17

Ethyl (2-ethyl-4-oxo-4,5-dihydro-2H-pyrazolo[3,4-c]quinolin-1-yl)acetate

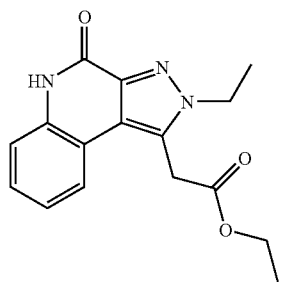

Part A

2-Nitrophenylacetic acid (15.0 g, 82.8 mmol) was dissolved in 330 mL of dichloromethane. Three drops of DMF were added, followed by dropwise addition of oxalyl chloride (14.4 mL, 165.6 mmol). The reaction was allowed to stir at ambient temperature for 3 hours, at which time the reaction was concentrated under reduced pressure to afford (2-nitrophenyl)acetyl chloride.

Part B

A mixture of the material obtained in Part A (82.8 mmol) and N,N-diisopropylethylamine (28.8 mL, 165.6 mmol) and dichloromethane (240 mL) was cooled to 0° C. Meldrum's acid (11.9 g, 82.8 mmol) was dissolved in 90 mL of dichloromethane and added dropwise to the cooled solution over 30 minutes. This mixture was allowed to stir overnight, slowly warming to ambient temperature. The reaction mixture was then washed with 100 mL of 1 N aqueous hydrochloric acid, 100 mL of saturated aqueous sodium chloride, dried over magnesium sulfate, and concentrated under reduced pressure to afford crude 2,2-dimethyl-5-[(2-nitrophenyl)acetyl]-1,3-dioxane-4,6-dione as a red oil.

Part C

The material from Part B was dissolved in ethanol (250 mL) and heated at reflux for 3 hours. The mixture was allowed to cool to ambient temperature and concentrated under reduced pressure. The red oil was passed through a layer of silica gel, eluting with chloroform. Concentration under reduced pressure afforded an orange oil that was crystallized from ethanol to afford 17.04 g of ethyl 4-(2-nitrophenyl)-3-oxobutanoate.

Part D

A mixture of ethyl 4-(2-nitrophenyl)-3-oxobutanoate (17.04 g, 67.8 mmol), 10% palladium on carbon (3.6 g), and ethanol (280 mL) was placed under hydrogen pressure (50 psi, $3.4 \times 10^5$ Pa) on a Parr apparatus for 96 hours. The reaction mixture was filtered through a layer of CELITE filter aid. The filtrate was concentrated under reduced pressure to provide crude ethyl 1H-indol-2-ylacetate.

Part E

The material from Part D was dissolved in dichloromethane (280 mL) and cooled to 0° C. Pyridine (6.9 mL, 85.7 mmol) and chloroethyloxalate (8.75 mL, 78.6 mmol) were added, and the reaction mixture was allowed to stir overnight, slowly warming to ambient temperature. 200 mL of water was added, and the aqueous layer was extracted with dichloromethane. The combined organic layers were dried over magnesium sulfate and then concentrated under reduced pressure. The residue was purified by automated flash chromatography eluting with a gradient of 0-10% CMA in chloroform to provide 15.5 g of ethyl (2-ethoxycarbonylmethyl-1H-indol-3-yl)-oxo-acetate.

Part F

A mixture of ethyl (2-ethoxycarbonylmethyl-1H-indol-3-yl)-oxo-acetate (6.28 g, 20.7 mmol), ethylhydrazine oxalate (4.67 g, 31.1 mmol), acetyl chloride (2.9 mL, 41.4 mmol), acetic acid (3.5 mL), and 80 mL of ethanol was heated at reflux for 36 hours. The mixture was allowed to cool to ambient temperature and concentrated under reduced pressure. The residue was taken up in 60 mL of saturated aqueous sodium bicarbonate, and the pH was adjusted to 8 with solid sodium bicarbonate. This mixture was extracted with chloroform, and the organic layer was dried over magnesium sulfate and concentrated under reduced pressure. The residue was triturated with acetonitrile, isolated by filtration, and dried to provide 5.05 g of solid. A sample was recrystallized from acetonitrile to afford 0.708 g of ethyl (2-ethyl-4-oxo-4,5-dihydro-2H-pyrazolo[3,4-c]quinolin-1-yl)acetate, mp 233-235° C. MS (ESI) m/z 300 (M+H)+; Anal. calcd for $C_{16}H_{17}N_3O_3$: C, 64.20; H, 5.72; N, 14.04. Found: C, 64.18; H, 5.56; N, 14.06.

Example 18

Ethyl (4-oxo-2-phenyl-4,5-dihydro-2H-pyrazolo[3,4-c]quinolin-1-yl)acetate

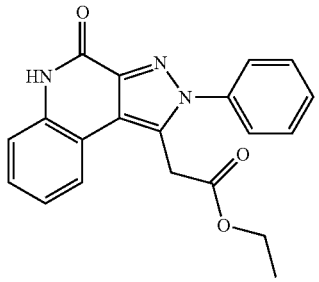

Ethyl (4-oxo-2-phenyl-4,5-dihydro-2H-pyrazolo[3,4-c]quinolin-1-yl)acetate was prepared according to the general method of Example 17 using phenylhydrazine in lieu of ethylhydrazine oxalate in Part F. The crude material was recrystallized from chloroform/methanol (80/20) to afford pure product as a white solid, mp 301-303° C. MS (ESI) m/z 348 (M+H)+; Anal. calcd for $C_{20}H_{17}N_3O_3$: C, 69.15; H, 4.93; N, 12.10. Found: C, 68.92; H, 4.82; N, 12.06.

Example 19

(4-Oxo-2-phenyl-4,5-dihydro-2H-pyrazolo[3,4-c]quinolin-1-yl)acetic acid

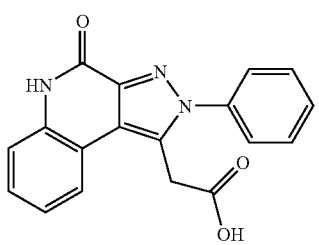

Ethyl (4-oxo-2-phenyl-4,5-dihydro-2H-pyrazolo[3,4-c]quinolin-1-yl)acetate (3.0 g, 8.64 mmol) was dissolved in 35 mL of ethanol and 2.9 mL of 6 N aqueous sodium hydroxide. The mixture was allowed to stir at ambient temperature overnight, and the pH was adjusted to 6 with 3 N aqueous hydrochloric acid. The mixture was filtered and dried to afford (4-oxo-2-phenyl-4,5-dihydro-2H-pyrazolo[3,4-c]quinolin-1-yl)acetic acid as a pale yellow solid, mp decomposed at 350° C. MS (ESI) m/z 320 (M+H)+; Anal. calcd for $C_{18}H_{13}N_3O_3$: C, 64.23; H, 4.47; N, 12.48. Found: C, 64.48; H, 4.38; N, 12.60.

Example 20

1-(2-Hydroxyethyl)-2-phenyl-2,5-dihydro-4H-pyrazolo[3,4-c]quinolin-4-one

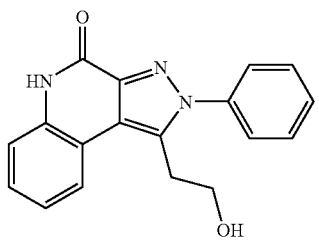

Ethyl (4-oxo-2-phenyl-4,5-dihydro-2H-pyrazolo[3,4-c]quinolin-1-yl)acetate (0.500 g, 1.44 mmol) was dissolved in 15 mL of tetrahydrofuran and cooled to 0° C. Lithium aluminum hydride (55 mg, 1.44) was added. The mixture was allowed to stir overnight, slowly warming to ambient temperature. An additional 55 mg of lithium aluminum hydride was added, and the mixture was stirred for 24 hours at ambient temperature. 0.15 mL of water, followed by 0.15 mL of 2 N aqueous sodium hydroxide and 0.45 mL of water was added. After stirring at ambient temperature for 1 hour, the mixture was dried over magnesium sulfate, filtered through a layer of CELITE filter aid, and concentrated under reduced pressure. The residue was purified by automated flash chromatography eluting with a gradient of 0-50% CMA in chloroform. The residue was triturated with methanol, isolated by filtration and dried to provide 0.211 g of 1-(2-hydroxyethyl)-2-phenyl-2,5-dihydro-4H-pyrazolo[3,4-c]quinolin-4-one as a white solid, mp 310-312° C. MS (ESI) m/z 306 (M+H)+; Anal. calcd for $C_{18}H_{15}N_3O_2$: C, 70.81; H, 4.95; N, 13.76. Found: C, 70.52; H, 4.83; N, 13.66.

Example 21

1-[2-(4-Benzylpiperazin-1-yl)-2-oxoethyl]-2-phenyl-2,5-dihydro-4H-pyrazolo[3,4-c]quinolin-4-one

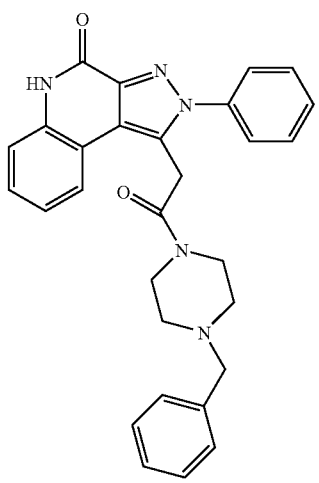

(4-Oxo-2-phenyl-4,5-dihydro-2H-pyrazolo[3,4-c]quinolin-1-yl)acetic acid (0.50 g, 1.6 mmol) was suspended in 5 mL of chloroform. Three drops of DMF were added followed by oxalyl chloride (0.20 mL, 2.3 mmol). The reaction mixture was stirred overnight at ambient temperature and concentrated under reduced pressure. The residue was dissolved in 10 mL of chloroform and N-benzylpiperazine (0.62 mL, 4.0 mmol) was added. The reaction was stirred at ambient temperature for 10 minutes and was then concentrated under reduced pressure. The residue was sequentially triturated and isolated by filtration with chloroform, 1% aqueous sodium carbonate, acetonitrile, and acetonitrile/water to provide 0.259 g of 1-[2-(4-benzylpiperazin-1-yl)-2-oxoethyl]-2-phenyl-2,5-dihydro-4H-pyrazolo[3,4-c]quinolin-4-one as off-white needles, mp 283-285° C. MS (ESI) m/z 478 (M+H)$^+$; Anal. calcd for $C_{29}H_{27}N_5O_2$: C, 72.94; H, 5.70; N, 14.66. Found: C, 72.73; H, 5.68; N, 14.57.

Example 22

1-[2-(4-Benzylpiperazin-1-yl)-2-oxoethyl]-4-chloro-2-phenyl-2H-pyrazolo[3,4-c]quinoline

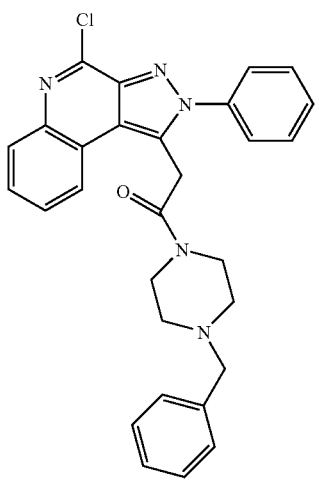

Part A (4-Oxo-2-phenyl-4,5-dihydro-2H-pyrazolo[3,4-c]quinolin-1-yl)acetic acid (8.83 g, 27.7 mmol) was suspended in 175 mL of chloroform. Twenty drops of DMF were added followed by oxalyl chloride (7.2 mL, 83.0 mmol). The reaction mixture was stirred at ambient temperature for 1 hour and concentrated under reduced pressure at 40° C. to afford crude (4-chloro-2-phenyl-2H-pyrazolo[3,4-c]quinolin-1-yl)acetyl chloride.

Part B

The material from Part A was dissolved in 200 mL of chloroform and N-benzylpiperazine (11.0 mL, 69.1 mmol). After stirring at ambient temperature for 10 minutes, the mixture was concentrated under reduced pressure. The residue was sequentially triturated and isolated by filtration with methanol, 1% aqueous sodium carbonate, and acetonitrile/water to provide 5.32 g of off-white needles. A sample was recrystallized from acetonitrile to provide 1-[2-(4-benzylpiperazin-1-yl)-2-oxoethyl]-4-chloro-2-phenyl-2H-pyrazolo[3,4-c]quinoline, mp 210.5-211.5° C. MS (APCI) m/z 496 (M+H)$^+$; Anal. calcd for $C_{29}H_{26}ClN_5O$: C, 70.22; H, 5.28; N, 14.12. Found: C, 70.44; H, 5.21; N, 14.22.

Example 23

1-[2-(4-Benzylpiperazin-1-yl)ethyl]-4-chloro-2-phenyl-2H-pyrazolo[3,4-c]quinoline

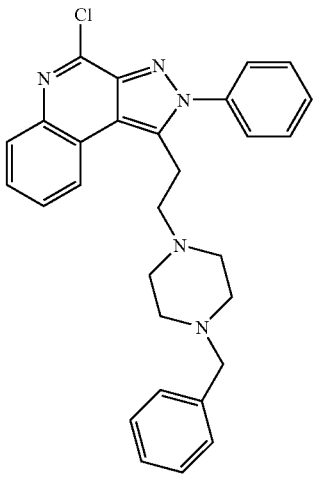

1-[2-(4-Benzylpiperazin-1-yl)-2-oxoethyl]-4-chloro-2-phenyl-2H-pyrazolo[3,4-c]quinoline (3.05 g, 6.1 mmol) was dissolved in 90 mL of tetrahydrofuran and cooled to 0° C. Lithium aluminum hydride (0.41 g, 10.75 mmol) was added. The mixture was allowed to stir at ambient temperature for 48 hours. A second portion of lithium aluminum hydride (0.17 g, 4.5 mmol) was added, and the mixture was stirred for 24 hours at ambient temperature. 0.6 mL of water, followed by 0.6 mL of 2 N aqueous sodium hydroxide and 1.8 mL of water was added. After stirring at ambient temperature for 30 minutes, the mixture was dried over magnesium sulfate, filtered through a layer of CELITE filter aid, and concentrated under reduced pressure. The residue was purified by automated flash chromatography eluting with a gradient of 4-18% CMA in chloroform, followed by automated flash chromatography eluting with a gradient of 10-67% ethyl acetate in hexanes to provide 0.46 g of 1-[2-(4-benzylpiperazin-1-yl)ethyl]-4-chloro-2-phenyl-2H-pyrazolo[3,4-c]quinoline as a yellow solid, mp 75-77° C. MS (ESI) m/z 482 (M+H)$^+$; Anal. calcd for $C_{29}H_{28}ClN_5$: C, 72.26; H, 5.85; N, 14.53. Found: C, 72.00; H, 5.67; N, 14.37.

Example 24

1-[2-(4-Benzylpiperazin-1-yl)ethyl]-2-phenyl-2,5-dihydro-4H-pyrazolo[3,4-c]quinolin-4-one

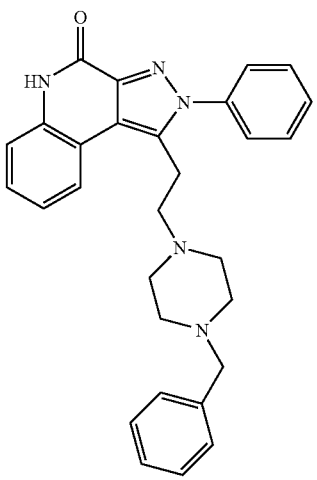

1-[2-(4-Benzylpiperazin-1-yl)ethyl]-4-chloro-2-phenyl-2H-pyrazolo[3,4-c]quinoline (0.32 g, 0.66 mmol) was refluxed in 5 mL of 6 N aqueous hydrochloric acid for 1 hour. The mixture was allowed to cool to ambient temperature, and the pH was adjusted to 10 with 10% w/v aqueous sodium carbonate. This mixture was concentrated under reduced pressure, and the residue was purified by automated flash chromatography eluting with a gradient of 0-15% CMA in chloroform. The residue was triturated with acetonitrile, isolated by filtration, and dried to afford 0.050 g of 1-[2-(4-benzylpiperazin-1-yl)ethyl]-2-phenyl-2,5-dihydro-4H-pyrazolo[3,4-c]quinolin-4-one as off-white needles, mp 211-212.5° C. MS (ESI) m/z 464 (M+H)$^+$; Anal. calcd for $C_{29}H_{29}N_5O$: C, 75.14; H, 6.31; N, 15.11. Found: C, 74.84; H, 6.35; N, 15.04.

Example 25 tert-Butyl 4-[2-(2-tert-butyl-4-oxo-4,5-dihydro-2H-pyrazolo[3,4-c]quinolin-1-yl)ethyl]piperidine-1-carboxylate

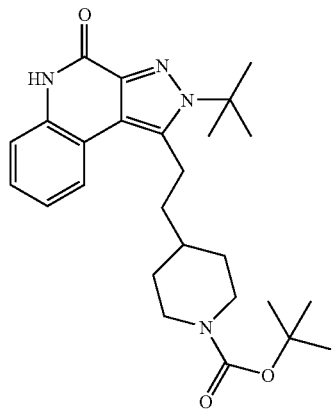

Part A 2-tert-Butyl-2,5-dihydro-pyrazolo[3,4-c]quinolin-4-one was synthesized using a procedure similar to that for Example 6 using tert-butylhydrazine hydrochloride in lieu of phenylhydrazine Part B.

Part B

To a round-bottomed flask containing 2-tert-butyl-2,5-dihydro-pyrazolo[3,4-c]quinolin-4-one (1.5 g, 6.2 mmol) was added tetrahydrofuran (20 mL) followed by N,N,N',N'-tetramethylethylenediamine (3.6 g, 31.1 mmol). The reaction was stirred under nitrogen in an ice bath. To this suspension n-butyllithium (2.5 M in hexanes, 7.47 mL, 18.67 mmol) was added dropwise. The reaction mixture was cooled to −78° C. in an acetone-dry ice bath and tert-butyl 4-(2-iodoethyl)piperidine-1-carboxylate (2.3 g, 6.84 mmol) was added to the reaction. The reaction was warmed to ambient temperature over 30 minutes and stirred at that temperature for another 2 hours. Methanol was carefully added to quench the reaction and the solvent was evaporated to afford a dark oil. The oil was taken up in ethyl acetate and the organic layer was washed with aqueous saturated sodium bicarbonate. The organic layer was separated, dried (magnesium sulfate), filtered, and evaporated to afford a dark oil. The product was purified twice by automated flash chromatography (Combiflash Separation System, eluted with a gradient of 0-5% methanol in dichloromethane with 1% ammonium hydroxide) to provide tert-butyl 4-[2-(2-tert-butyl-4-oxo-4,5-dihydro-2H-pyrazolo[3,4-c]quinolin-1-yl)-ethyl]-piperidine-1-carboxylate as a gray solid (0.17 g), mp 223-225° C.; MS (ESI) m/z 453 (M+H).

Example 26

2-tert-Butyl-1-(hydroxymethyl)-2,5-dihydro-4H-pyrazolo[3,4-c]quinolin-4-one

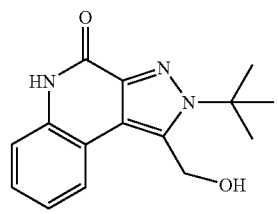

A stirring solution of 2-tert-butyl-2,5-dihydro-4H-pyrazolo[3,4-c]quinolin-4-one (10.0 g, 41.4 mmol) in tetrahydrofuran (400 mL) and N,N,N',N' tetramethylethylenediamine (28 mL) was placed under an atmosphere of nitrogen and cooled to 0° C. n-Butyllithium (2.5M solution in hexanes, 49.7 mL, 124 mmol) was added dropwise over 30 minutes via an addition funnel. The resulting suspension was stirred at 0° C. for 15 minutes at which point paraformaldehyde (10.0 g, 333 mmol) was added in portions over 2 minutes. The suspension was allowed to warm to ambient temperature and stir for 2 hours. Additional paraformaldehyde (5.0 g, 167 mmol) was added and the resulting suspension stirred for 1.5 hours. Saturated aqueous ammonium chloride (150 mL) was added carefully and the mixture transferred to a separatory funnel. The aqueous layer was extracted with dichloromethane (3×150 mL). The combined organic layers were concentrated to a brown solid which was triturated with acetonitrile (100 mL). The solid was isolated by filtration and the filter cake was washed with additional acetonitrile (100 mL). The cake was dried in a vacuum oven at 65° C. overnight to yield 5.0 g of 2-tert-butyl-1-(hydroxymethyl)-2,5-dihydro-4H-pyrazolo[3,4-c]quinolin-4-one as a tan solid. 500 mg of this material was crystallized from hot acetonitrile (100 mL) and isolated by filtration to yield 288 mg of 2-tert-butyl-1-(hydroxymethyl)-2,5-dihydro-4H-pyrazolo[3,4-c]quinolin-4-one as a tan solid, mp 295-297° C. Anal. calcd for $C_{15}H_{17}N_3O_2$: C, 66.40; H, 6.32; N, 15.49. Found: C, 66.26; H, 6.64; N, 15.54.

Example 27

1-Isobutyl-2-methyl-2H-pyrazolo[3,4-c]quinolin-4-ol

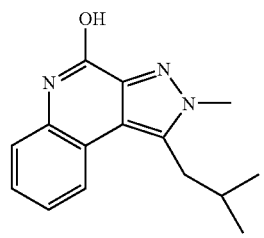

Part A

A 1 L round bottom flask was charged with ethyl 6-methyl-2,4-dioxoheptanoate sodium salt (30.0 g, 135 mmol) and acetic acid (200 mL). Methylhydrazine (7.20 mL, 135 mmol) was added dropwise via syringe, and the resultant solution was allowed to stir under a nitrogen atmosphere for 2 hours. The pH was then adjusted to 9 by addition of saturated aqueous sodium carbonate, and the reaction mixture was extracted with dichloromethane (3×100 mL). The combined organic layers were washed with brine, dried over magnesium sulfate, filtered, and concentrated to provide 27.5 g of ethyl 5-isobutyl-1-methyl-1H-pyrazole-3-carboxylate as a yellow oil. This material was utilized without any further purification.

Part B

A 1 L round bottom flask was charged with material from Part A (27.5 g, 131 mmol) and absolute ethanol (218 mL). An aqueous 6N aqueous sodium hydroxide solution (44 mL, 262 mmol) was added via pipette, and the resultant orange solution was heated at reflux overnight. The following morning, the solvents were removed by rotary evaporation. The residue was dissolved in water (200 mL) and extracted with dichloromethane (3×50 mL). The pH of the aqueous layer was then adjusted to 4 by addition of aqueous 1N aqueous hydrochloric acid, and extracted with ethyl acetate (3×75 mL). The combined ethyl acetate layers were washed with brine, dried over magnesium sulfate, filtered, and concentrated to afford 23.9 g of 5-isobutyl-1-methyl-1H-pyrazole-3-carboxylic acid as an orange oil. This material was utilized without any further purification.

Part C

A 200 mL round bottom flask was charged with material from Part B (5.00 g, 27.4 mmol) and anhydrous DMF (60 mL). N-ethyl-NA-(3-dimethylaminopropyl)carbodiimide (5.52 g, 28.8 mmol) and hydroxybenzotriazole hydrate (3.89 g, 28.8 mmol) were added, resulting in the formation of a cloudy mixture. After stirring at ambient temperature for 15 minutes, the solution again became homogeneous, and a solution of 2-bromoaniline (4.96 g, 28.8 mmol) in DMF (10 mL) was added via pipette. The resultant solution was allowed to stir overnight under nitrogen atmosphere. The following morning, most of the solvents were removed by rotary evaporation, and the residue was partitioned between water and dichloromethane. The aqueous layer was extracted with additional portions of dichloromethane (3×50 mL). The combined organic layers were then washed with brine, dried over magnesium sulfate, filtered, and concentrated to afford a tan oil. Purification via flash chromatography (silica gel, ramp eluent from 19/1 to 9/1 hexane/ethyl acetate) provided 4.87 g of N-(2-bromophenyl)-5-isobutyl-1-methyl-1H-pyrazole-3-carboxamide as a clear colorless oil that solidified to a white solid under vacuum.

Part D

The material obtained in Part C (5.65 g, 16.8 mmol) in anhydrous tetrahydrofuran (80 mL) was cooled to 0° C. in an ice bath, and a slurry of potassium hydride (2.70 g of a 30% dispersion in mineral oil, 20.2 mmol) in anhydrous tetrahydrofuran (10 mL) was carefully added via pipette. Evolution of hydrogen gas was readily apparent, and the reaction mixture slowly became purple in color. After stirring at 0° C. for 15 min. and at ambient temperature for 15 min., 4-methoxybenzyl chloride (3.42 mL, 25.2 mmol) was added via syringe, and the resultant solution was heated at reflux overnight. The following morning, the solution was partitioned between water and ethyl acetate, and the aqueous layer was extracted with additional portions of ethyl acetate (3×75 mL). The combined organic layers were washed with brine, dried over magnesium sulfate, filtered, and concentrated to afford an orange oil. Purification via flash chromatography (silica gel, ramp eluent from 3/2 to 1/1 hexane/ethyl acetate) afforded 6.23 g of N-(2-bromophenyl)-5-isobutyl-N-(4-methoxybenzyl)-1-methyl-1H-pyrazole-3-carboxamide as a viscous pale yellow oil.

Part E

A pressure tube was charged with material from Part D (2.00 g, 4.38 mmol) and anhydrous DMF (30 mL). Nitrogen was bubbled through the resultant solution for several minutes, and palladium acetate (294 mg, 1.31 mmol) and sodium bicarbonate (924 mg, 11.0 mmol) were then added. The pressure tube was sealed and heated in a 150° C. oil bath for 22 hours. The pressure tube was then cooled to ambient temperature and opened, and the reaction mixture was diluted with ethyl acetate (100 mL) and filtered through CELITE filter aid. The filtrate was washed with water (2×50 mL) and brine, then dried over magnesium sulfate, filtered, and concentrated to afford a yellow oil. Purification via flash chromatography (silica gel, 3% methanol in dichloromethane eluent) provided 1.38 g of 1-isobutyl-5-(4-methoxybenzyl)-2-methyl-2,5-dihydro-4H-pyrazolo[3,4-c]quinolin-4-one as a pale yellow oil that foams under vacuum.

Part F

A pressure tube was charged with material from Part E (730 mg, 1.94 mmol) and trifluoroacetic acid (10 mL). The pressure tube was sealed and placed in a 70° C. oil bath for 72 hours. After cooling to ambient temperature, the pressure tube was opened, and the reaction mixture was diluted with water. The pH was adjusted to 7 by addition of saturated aqueous sodium carbonate, and the resultant aqueous phase was extracted with dichloromethane (3×75 mL). The combined organic layers were washed with brine, dried over magnesium sulfate, filtered, and concentrated to a tan solid. Purification via flash chromatography (silica gel, ramp eluent from 3-5% methanol in dichloromethane) provided 220 mg of 1-isobutyl-2-methyl-2H-pyrazolo[3,4-c]quinolin-4-ol as a tan crystalline solid, mp>280° C. $^1$H NMR (300 MHz, CDCl$_3$) δ 11.1 (s, 1H), 7.80 (d, J=7.0 Hz, 1H), 7.53 (d, J=−7.0 Hz, 1H), 7.35 (t, J=7.4 Hz, 1H), 7.24 (t, J=7.3 Hz, 1H), 4.13 (s, 3H), 3.03 (d, J=7.5 Hz, 2H), 2.19 (septet, J=6.8 Hz, 1H), 1.06 (d, J=6.7 Hz, 6H); MS (APCI) m/z 256 (M+H)$^+$; Anal. calcd for C$_{15}$H$_{17}$N$_3$O: C, 70.56; H, 6.71; N, 16.46. Found: C, 70.41; H, 6.72; N, 16.54.

Example 28

2-Phenyl-1-propyl-2,5-dihydro-4H-pyrazolo[3,4-c]quinolin-4-one

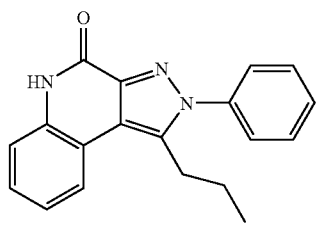

Part A

A mixture of 2-iodoaniline (500 mg, 2.28 mmol), 1-pentyne (0.27 mL, 2.74 mmol), bis(triphenylphosphine)palladium (II) chloride (77 mg, 0.11 mmol), copper iodide (21 mg, 0.11 mmol), triethylamine (0.95 mL, 6.84 mmol), and acetonitrile (10 mL) was stirred at ambient temperature for 2 hours.

The reaction mixture was concentrated under reduced pressure. The residue was stirred in diethyl ether and filtered. The filtrate was concentrated under reduced pressure to afford 0.25 g of 2-pent-1-ynylaniline.

Part B

A mixture of 2-pent-1-ynylaniline (0.25 g, 1.57 mmol), copper iodide (30 mg, 0.16 mmol), and N,N-dimethylformamide (6 mL) was heated at 140° C. for 4 hours and concentrated. The crude material was dissolved in diethyl ether, filtered through a layer of CELITE filter aid, and concentrated under reduced pressure. The residue was purified by automated flash chromatography eluting with a gradient of 0-20% ethyl acetate in hexanes to provide 0.20 g of 2-propyl-1H-indole.

Part C

2-Propyl-1H-indole (0.20 g, 1.27 mmol) was dissolved in dichloromethane (8 mL) and cooled to 0° C. Pyridine (0.12 mL, 1.53 mmol) and chloroethyloxalate (0.16 mL, 1.40 mmol) were added, and the reaction mixture was allowed to stir overnight, slowly warming to ambient temperature. 30 mL of water was added, and the aqueous layer was extracted with dichloromethane. The combined organic layers were dried over magnesium sulfate and then concentrated under reduced pressure.

Part D

A mixture of the material from Part C, phenylhydrazine (0.19 mL, 1.91 mmol), acetyl chloride (0.18 mL, 2.54 mmol), acetic acid (0.21 mL), and 8 mL of ethanol was heated at reflux for 18 hours. The mixture was allowed to cool to ambient temperature and concentrated under reduced pressure. The residue was taken up in 30 mL of water, and the pH was adjusted to 8 with solid sodium bicarbonate. The resulting solid was filtered, triturated with acetonitrile, isolated by filtration, and dried to provide 0.246 g of 2-phenyl-1-propyl-2,5-dihydro-4H-pyrazolo[3,4-c]quinolin-4-one as a white solid. mp>300° C.; MS (ESI) m/z 304 (M+H)$^+$; Anal. calcd for $C_{19}H_{17}N_3O$: C, 75.23; H, 5.65; N, 13.85. Found: C, 75.07; H, 5.52; N, 13.86.

Example 29

1-(2-Hydroxy-2-methylpropyl)-2-propyl-2H-pyrazolo[3,4-c]quinolin-4-ol

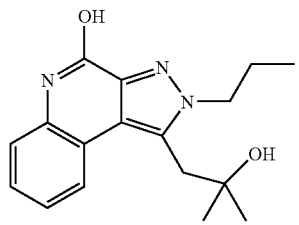

Part A

To a mixture of mesityl oxide (58.1 g, 500 mmol), dichloromethane (500 mL), and triethylamine (60.7 g, 600 mmol) at 0° C. was added chlorotrimethylsilane (60 g, 550 mmol). The reaction was warmed to ambient temperature over 2 hours and stirred at this temperature for 22 hours. The reaction was diluted with water. The layers were separated. The aqueous layer was extracted with additional dichloromethane. The combined organic layers were dried over magnesium sulfate, filtered, and concentrated to a brown oil. The oil was dissolved in hexanes and washed with water. The organic layer was dried over magnesium sulfate, filtered, and concentrated to 87.9 g of 4-methyl-4-[(trimethylsilyl)oxy]pentan-2-one as a pale brown oil.

Part B

To a solution of sodium tert-butoxide dissolved in ethanol (71 mL) was added diethyl oxalate (16.1 g, 110 mmol) followed by the material obtained in Part A (18.8 g, 100 mmol). The reaction was stirred 30 minutes at ambient temperature before cooling to 0° C. and adding acetic acid (100 mL) and propylhydrazine oxalate (16.4 g, 100 mmol). The reaction was allowed to warm to ambient temperature and stirred for 19 hours. The solvent was removed under reduced pressure. The resulting brown oil was purified by automated flash chromatography (AnaLogix, eluting with a gradient of 50-75% ethyl acetate in hexanes) to provide 9.6 g of ethyl 5-(2-hydroxy-2-methylpropyl)-1-propyl-1H-pyrazole-3-carboxylate as a yellow oil.

Part C

To a mixture of the material obtained in Part B (9.6 g, 38 mmol), acetic acid (75 mL), and potassium acetate (9.3 g, 94 mmol) was added bromine (8.44 g, 52.8 mmol). The reaction was allowed to stand for 1 week. Sodium bisulfite was added and the acetic acid was removed under reduced pressure. 2N aqueous sodium carbonate was added and the mixture was extracted with methyl t-butyl ether. The organic layer was dried over magnesium sulfate, filtered, and concentrated. The residue was purified by automated flash chromatography (AnaLogix, eluting with a gradient of 50-75% ethyl acetate in hexanes) to provide 11.5 g of ethyl 4-bromo-5-(2-hydroxy-2-methylpropyl)-1-propyl-1H-pyrazole-3-carboxylate as a yellow oil.

Part D

The material obtained in Part C (1.33 g, 4.00 mmol) was dissolved in 1,2-dimethoxyethane (15 mL) and water (7.5 mL). To the resulting solution was added potassium carbonate (1.82 g, 13.1 mmol), 2-aminophenylboronic acid hydrochloride (1.39 g, 8.0 mmol), and dichlorobis(triphenylphosphine)palladium(0) (140 mg, 0.2 mmol). The flask was evacuated and backfilled with nitrogen before stirring at reflux for 24 hours. The reaction was cooled to ambient temperature. The reaction was partitioned between water and methyl t-butyl ether. The layers were separated. The aqueous layer was extracted with additional methyl t-butyl ether. The combined organic layers were dried over magnesium sulfate, filtered, and concentrated to a brown oil. This material was purified by automated flash chromatography (AnaLogix, eluting with a gradient of 20-40% CMA in chloroform) and then recrystallized from acetonitrile to provide 98 mg of 1-(2-hydroxy-2-methylpropyl)-2-propyl-2H-pyrazolo[3,4-c]quinolin-4-ol as a white solid, mp 294-296° C. Anal. calcd for $C_{17}H_{21}N_3O_2$: C, 68.21; H, 7.07; N, 14.04. Found: C, 67.99; H, 7.46; N, 14.23.

Examples 30-36

A solution of 2-phenyl-1-(2-piperidin-4-ylethyl)-2,5-dihydro-4H-pyrazolo[3,4-c]quinolin-4-one (37 mg, 0.10 mmol, 1.0 eq) in methanol (1 mL) was added to a test tube containing an aldehyde (1.25 eq) from the table below. The reaction mixture was stirred for 15 minutes. Borane-pyridine complex (16 μL, 1.3 eq) was added and the reaction mixture was stirred overnight. The reaction was quenched with water (2 drops). The solvent was removed by vacuum centrifugation. The compounds were purified by preparative high performance liquid chromatography (prep HPLC) using a Waters Fraction-Lynx automated purification system. The prep HPLC fractions were analyzed using a Waters LC/TOF-MS, and the appropriate fractions were centrifuge evaporated to provide the trifluoroacetate salt of the desired compound. Reversed phase preparative liquid chromatography was performed with non-linear gradient elution from 5-95% B where A is 0.05% trifluoroacetic acid/water and B is 0.05% trifluoroacetic acid/acetonitrile. Fractions were collected by mass-selective triggering. The table below shows the aldehyde used for each example, the structure of the resulting compound, and the observed accurate mass for the isolated trifluoroacetate salt.

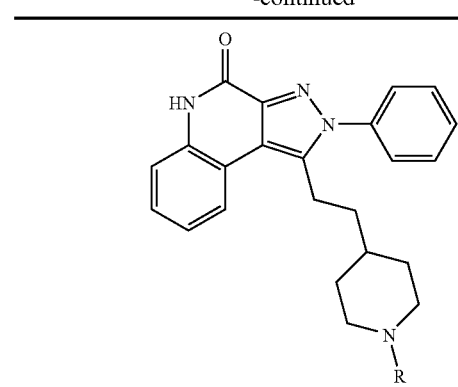

| Example | Reagent | R | Measured Mass (M + H) |
|---|---|---|---|
| 30 | Cyclopropane-carboxaldehyde | (cyclopropylmethyl) | 427.2497 |
| 31 | Isobutyraldehyde | (isobutyl) | 429.2643 |
| 32 | Butyraldehyde | (butyl) | 429.2641 |
| 33 | Benzaldehyde | (benzyl) | 463.2508 |
| 34 | Isonicotinaldehyde | (4-pyridylmethyl) | 464.2444 |
| 35 | Nicotinaldehyde | (3-pyridylmethyl) | 464.2426 |
| 36 | Cyclohexane carboxaldehyde | (cyclohexylmethyl) | 469.2957 |

Examples 37-43

A reagent (1.1 eq.) from the table below was added to a test tube containing a solution of 2-phenyl-1-(2-piperidin-4-yl-ethyl)-2,5-dihydro-4H-pyrazolo[3,4-c]quinolin-4-one (37 mg, 0.10 mmol, 1.0 eq) and N,N-diisopropylethylamine (34 μL, 2 eq) in N,N-dimethylacetamide (1 mL). The reaction mixture was stirred overnight and then quenched with water (2 drops). The solvent was removed by vacuum centrifugation. The compounds were purified using the method described in Examples 30-36. The table below shows the reagent used for each example, the structure of the resulting compound, and the observed accurate mass for the isolated trifluoroacetate salt.

| Example | Reagent | R | Measured Mass (M + H) |
|---|---|---|---|
| 37 | Cyclopropanecarbonyl chloride | cyclopropyl-C(=O)- | 441.2292 |
| 38 | Isobutyryl chloride | (CH3)2CH-C(=O)- | 443.2482 |
| 39 | Benzoyl chloride | Ph-C(=O)- | 477.2303 |
| 40 | Nicotinoyl chloride hydrochloride | 3-pyridyl-C(=O)- | 478.2249 |
| 41 | Isopropylsulfonyl chloride | (CH3)2CH-S(=O)2- | 479.2115 |
| 42 | 1-Piperidinecarbonyl chloride | piperidinyl-C(=O)- | 484.2711 |
| 43 | 4-Morpholinylcarbonyl chloride | morpholinyl-C(=O)- | 486.2493 |

Examples 44-70

Part A

Thionyl chloride (6.0 mL, 9.9 g, 82.9 mmol) was added dropwise to a stirring suspension of 2-tert-butyl-1-(hydroxymethyl)-2,5-dihydro-4H-pyrazolo[3,4-c]quinolin-4-one (4.5 g, 16.6 mmol) in 1,2-dichloroethane (160 mL) and the resulting suspension was stirred at ambient temperature overnight. The volatiles were removed under reduced pressure to yield 5.34 g of 2-tert-butyl-1-(chloromethyl)-2,5-dihydro-4H-pyrazolo[3,4-c]quinolin-4-one hydrochloride as a brown solid.

Part B

A solution of 2-tert-butyl-1-(chloromethyl)-2,5-dihydro-4H-pyrazolo[3,4-c]quinolin-4-one hydrochloride (33 mg, 0.11 mmol) in N,N-dimethylacetamide (1 mL) was added to a test tube containing a reagent (1.5 eq) from the table below and anhydrous potassium carbonate (55 mg, 4 eq). The reaction mixtures for examples 44-70 were heated at 75° C. for 23 hours. The reaction mixtures for examples 71-79 were heated at 105° C. for 24 hours. The reaction mixture was filtered and the filtrate was concentrated by vacuum centrifugation. The compounds were purified using the method described in Examples 30-36. The table below shows the reagent used for each example, the structure of the resulting compound, and the observed accurate mass for the isolated trifluoroacetate salt.

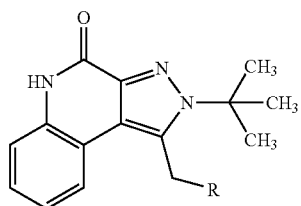

| Example | Reagent | R | Measured Mass (M + H) |
|---|---|---|---|
| 44 | Piperidine | piperidin-1-yl | 339.2202 |
| 45 | Thiazolidine | thiazolidin-3-yl | 343.1628 |
| 46 | 3-Methylpiperidine | 3-methylpiperidin-1-yl | 353.2358 |
| 47 | 2-Methylpiperidine | 2-methylpiperidin-1-yl | 353.2357 |
| 48 | 1-Methylpiperazine | 4-methylpiperazin-1-yl | 354.2278 |
| 49 | 4-Hydroxypiperidine | 4-hydroxypiperidin-1-yl | 355.2139 |
| 50 | N,N,N'-Trimethylethylenediamine | -N(CH₃)CH₂CH₂N(CH₃)₂ | 356.2470 |
| 51 | 2-(Propylamino)ethanol | -N(CH₂CH₂CH₃)(CH₂CH₂OH) | 357.2304 |
| 52 | N,N'-Dimethyl-3-aminopyrrolidine | -N(CH₃)(1-methylpyrrolidin-3-yl) | 368.2464 |

-continued
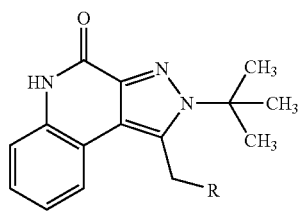
| Example | Reagent | R | Measured Mass (M + H) |
|---|---|---|---|
| 53 | N-Methylhomopiperazine | | 368.2482 |
| 54 | 3-Azabicyclo[3.2.2]nonane | | 379.2510 |
| 55 | Isonipecotamide | | 382.2249 |
| 56 | 1-Methyl-4-(methylamino)piperidine | | 382.2645 |
| 57 | 4-Piperidineethanol | | 383.2445 |
| 58 | N-(2-Hydroxyethyl)piperazine | | 384.2427 |
| 59 | 1,2,3,4-Tetrahydroisoquinoline | | 387.2225 |
| 50 | 4-(Ethylaminomethyl)pyridine | | 390.2295 |

-continued

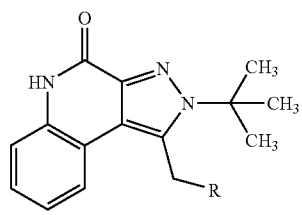

| Example | Reagent | R | Measured Mass (M + H) |
|---|---|---|---|
| 61 | 1-(2-Methoxyethyl)piperazine | *N-piperazine-CH2CH2-O-CH3* | 398.2564 |
| 62 | 4-(1-Pyrrolidinyl)piperidine | *N-piperidine-pyrrolidine* | 408.2799 |
| 63 | 1-(2-Ethoxyethyl)piperazine | *N-piperazine-CH2CH2-O-CH2CH3* | 412.2734 |
| 64 | 3-(3-Pyridylmethylamino)propionitrile | *N(Me)(CH2CH2CN)(CH2-3-pyridyl)* | 415.2245 |
| 65 | 1-Phenylpiperazine | *N-piperazine-phenyl* | 416.2475 |
| 66 | 1-(2-Pyridyl)piperazine | *N-piperazine-2-pyridyl* | 417.2432 |
| 67 | 1-(4-Pyridyl)piperazine | *N-piperazine-4-pyridyl* | 417.2388 |
| 68 | 1-Cyclohexylpiperazine | *N-piperazine-cyclohexyl* | 422.2949 |

-continued
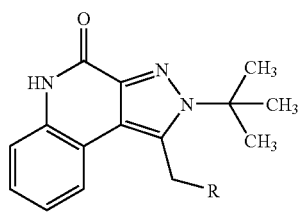
| Example | Reagent | R | Measured Mass (M + H) |
|---|---|---|---|
| 69 | 4-Piperidinopiperidine | 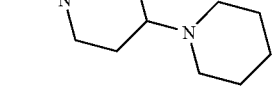 | 422.2934 |
| 70 | 1-(2-Fluorophenyl)piperazine | 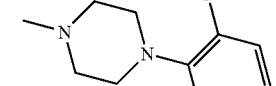 | 434.2396 |
| 71 | m-Cresol | 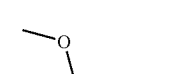 | 362.1897 |
| 72 | o-Cresol | 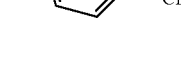 | 362.1903 |
| 73 | p-Cresol | 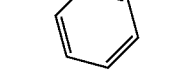 | 362.1897 |
| 74 | 2-Fluorophenol | 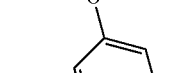 | 366.1648 |
| 75 | 3-Fluorophenol |  | 366.1654 |

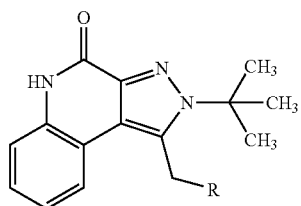

| Example | Reagent | R | Measured Mass (M + H) |
|---|---|---|---|
| 76 | 2-Dimethylaminomethylphenol | | 405.2308 |
| 77 | 4-Dimethylaminomethylphenol | | 405.2322 |
| 78 | 2,3-Dimethoxyphenol | | 408.1961 |
| 79 | 3-Hydroxybenzotrifluoride | | 416.1624 |

Examples 80-133

Part A 1-(Hydroxymethyl)-2,5-dihydro-2-phenyl-4H-pyrazolo[3,4-c]quinolin-4-one was prepared according to the general method of Example 26 using 2,5-dihydro-2-phenyl-4H-pyrazolo[3,4-c]quinolin-4-one in lieu of 2-tert-butyl-2,5-dihydro-4H-pyrazolo[3,4-c]quinolin-4-one.

Part B 1-(Chloromethyl)-2,5-dihydro-2-phenyl-4H-pyrazolo[3,4-c]quinolin-4-one hydrochloride was prepared according to the general method of Part A of Examples 44-79 using 1-(hydroxymethyl)-2,5-dihydro-2-phenyl-4H-pyrazolo[3,4-c]quinolin-4-one in lieu of 2-tert-butyl-1-(hydroxymethyl)-2,5-dihydro-4H-pyrazolo[3,4-c]quinolin-4-one.

Part C

A solution of 1-(chloromethyl)-2,5-dihydro-2-phenyl-4H-pyrazolo[3,4-c]quinolin-4-one hydrochloride (35 mg, 0.11 mmol) in N,N-dimethylacetamide (1 mL) was added to a test tube containing a reagent (1.5 eq) from the table below and anhydrous potassium carbonate (55 mg, 4 eq). The reaction mixtures for examples 80-132 were heated at 75° C. for 17 hours. The reaction mixture for example 133 was heated at 90° C. for 17 hours. The reaction mixture was filtered and the filtrate was concentrated by vacuum centrifugation. The compounds were purified using the method described in Examples 30-36. The table below shows the reagent used for each example, the structure of the resulting compound, and the observed accurate mass for the isolated trifluoroacetate salt.

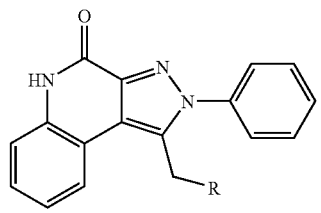

| Example | Reagent | R | Measured Mass (M + H) |
|---|---|---|---|
| 80 | Pyrrolidine | pyrrolidin-1-ylmethyl | 345.1719 |
| 81 | 2-(Methylamino)ethanol | N-methyl-N-(2-hydroxyethyl)aminomethyl | 349.1669 |
| 82 | 2-Methylpyrrolidine | 2-methylpyrrolidin-1-ylmethyl | 359.1899 |
| 83 | Piperidine | piperidin-1-ylmethyl | 359.1869 |
| 84 | Morpholine | morpholin-4-ylmethyl | 361.1652 |
| 85 | N-Methylbutylamine | N-methyl-N-butylaminomethyl | 361.2014 |
| 86 | 3-Methylpiperidine | 3-methylpiperidin-1-ylmethyl | 373.2025 |
| 87 | 4-Methylpiperidine | 4-methylpiperidin-1-ylmethyl | 373.2029 |
| 88 | Hexamethyleneimine | azepan-1-ylmethyl | 373.2047 |
| 89 | 2-Methylpiperidine | 2-methylpiperidin-1-ylmethyl | 373.2033 |

-continued
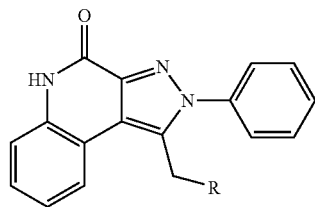
| Example | Reagent | R | Measured Mass (M + H) |
|---|---|---|---|
| 90 | 1-Methylpiperazine | (N-methylpiperazinyl) | 374.1987 |
| 91 | 3-Hydroxypiperidine | (3-hydroxypiperidinyl) | 375.1828 |
| 92 | 4-Hydroxypiperidine | (4-hydroxypiperidinyl) | 375.1807 |
| 93 | N-Methylpentylamine | —N(CH₃)(pentyl) | 375.2194 |
| 94 | 2-(Propylamino)ethanol | —N(propyl)(CH₂CH₂OH) | 377.1946 |
| 95 | Thiomorpholine | (thiomorpholinyl) | 377.1430 |
| 96 | Diethanolamine | —N(CH₂CH₂OH)₂ | 379.1761 |
| 97 | 3-Methylamino-1,2-propanediol | —N(CH₃)(CH₂CH(OH)CH₂OH) | 379.1787 |

-continued

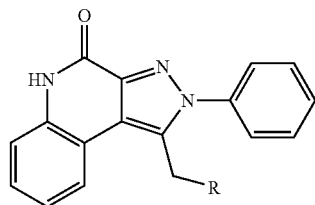

| Example | Reagent | R | Measured Mass (M + H) |
|---|---|---|---|
| 98 | N-Methylfurfurylamine | [CH3-N(CH3)-CH2-furan] | 385.1659 |
| 99 | N-Propylcyclopropanemethylamine | [N(CH3)(CH2CH2CH3)(CH2-cyclopropyl)] | 387.2178 |
| 100 | 3,5-Dimethylpiperidine | [3,5-dimethylpiperidinyl] | 387.2187 |
| 101 | N-Methylcyclohexylamine | [N(CH3)(cyclohexyl)] | 387.2198 |
| 102 | 3-(Dimethylamino)pyrrolidine | [3-(N(CH3)2)-pyrrolidinyl] | 388.2120 |
| 103 | N-Ethylpiperazine | [4-ethylpiperazinyl] | 388.2126 |
| 104 | N-Methylhomopiperazine | [4-methylhomopiperazinyl] | 388.2141 |
| 105 | 3-(Hydroxymethyl)piperidine | [3-(hydroxymethyl)piperidinyl] | 389.1974 |

-continued
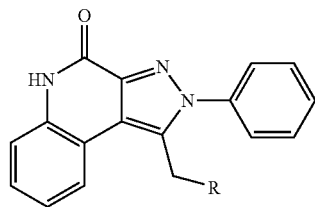
| Example | Reagent | R | Measured Mass (M + H) |
|---|---|---|---|
| 106 | 4-(Hydroxymethyl)piperidine | *N*-methylpiperidin-4-yl-CH2OH | 389.1992 |
| 107 | N,N,N'-Trimethyl-1,3-propanediamine | -N(CH3)CH2CH2CH2N(CH3)2 | 390.2271 |
| 108 | N,N-Dimethyl-N'-ethylethylenediamine | -N(Et)CH2CH2N(CH3)2 | 390.2275 |
| 109 | 4-Ethylamino-1-butanol | -N(Et)CH2CH2CH2CH2OH | 391.2154 |
| 110 | N-(2-Methoxyethyl)-N-propylamine | -N(nPr)CH2CH2OCH3 | 391.2159 |
| 111 | 2-(Butylamino)ethanol | -N(CH2CH2OH)(nBu) | 391.2133 |

-continued
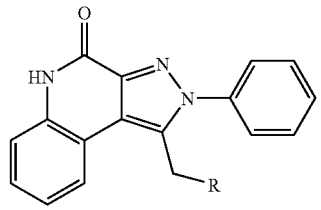
| Example | Reagent | R | Measured Mass (M + H) |
|---|---|---|---|
| 112 | 3-Azabicyclo[3.2.2]nonane | | 399.2173 |
| 113 | N-Ethylcyclohexylamine | | 401.2334 |
| 114 | Isonipecotamide | | 402.1919 |
| 115 | Nipecotamide | | 402.1933 |
| 116 | 1-Acetylpiperazine | | 402.1926 |
| 117 | 1-Methyl-4-(methylamino)piperidine | | 402.2262 |
| 118 | Isonipecotic acid | | 403.1795 |

-continued

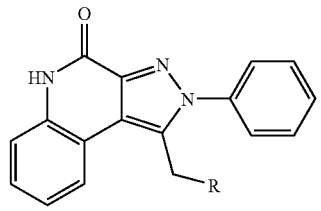

| Example | Reagent | R | Measured Mass (M + H) |
|---|---|---|---|
| 119 | Nipecotic acid | 1-methylpiperidine-3-carboxylic acid | 403.1768 |
| 120 | 2-(Ethylamino)-1,3,4-thiadiazole | N-ethyl-N-methyl-1,3,4-thiadiazol-2-amine | 403.1351 |
| 121 | 4-Piperidineethanol | 2-(1-methylpiperidin-4-yl)ethanol | 403.2132 |
| 122 | N-(2-Hydroxyethyl)piperazine | 2-(4-methylpiperazin-1-yl)ethanol | 404.2105 |
| 123 | 2-(N-Amylamino)ethanol | 2-(methyl(pentyl)amino)ethanol | 405.2289 |
| 124 | Bis (2-Methoxyethyl)amine | N,N-bis(2-methoxyethyl)methylamine | 407.2073 |

-continued

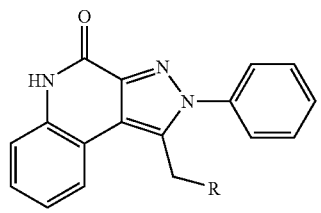

| Example | Reagent | R | Measured Mass (M + H) |
|---|---|---|---|
| 125 | 4-(3-Hydroxybutylamino)butan-2-ol | bis(2-hydroxypropyl)methylamino group | 407.2078 |
| 126 | (R)-(+)-N-Methyl-1-phenylethylamine | N,N-dimethyl-(R)-1-phenylethylamino | 409.2044 |
| 127 | N-Methylphenethylamine | N-methyl-N-phenethylamino | 409.2029 |
| 128 | 4-(Ethylaminomethyl)pyridine | N-ethyl-N-(pyridin-4-ylmethyl)amino | 410.1984 |
| 129 | 1-(4-Pyridyl)piperazine | 4-(pyridin-4-yl)piperazin-1-yl | 437.2082 |
| 130 | 1-Cyclohexylpiperazine | 4-cyclohexylpiperazin-1-yl | 442.2585 |
| 131 | 4-Piperidinopiperidine | 4-piperidin-1-ylpiperidin-1-yl | 442.2600 |

-continued

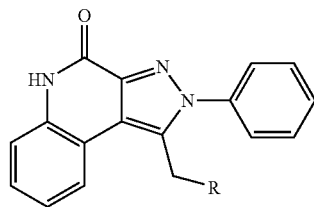

| Example | Reagent | R | Measured Mass (M + H) |
|---|---|---|---|
| 132 | 4-(4-Fluorophenyl)-1,2,3,6-tetrahydropyridine hydrochloride | (4-fluorophenyl-tetrahydropyridinyl group) | 451.1941 |
| 133 | 3-Fluorophenol | (3-fluorophenoxy group) | 386.1310 |

Examples 134-140

Part A

To a round-bottomed flask containing 2-tert-butyl-2,5-dihydropyrazolo[3,4-c]quinolin-4-one (20.0 g, 82.99 mmol) was added THF (500 mL) followed by N,N,N',N'-tetramethylethylenediamine (48.13 g, 414.94 mmol). The reaction was stirred under a nitrogen atmosphere in an ice bath. To this suspension n-butyl lithium (2.5 M in hexanes, 130.0 mL, 324.91 mmol) was added dropwise. The reaction mixture was stirred in the ice bath for 2 minutes and then ethyl iodide (258.38 g, 1.66 mol) was added to the reaction. The reaction was stirred in the ice bath for 10 minutes and then the ice bath was removed. The reaction was stirred at ambient temperature overnight. Methanol (60 mL) was carefully added to quench the reaction and the solvent was evaporated to afford a dark oil. The oil was taken up in ethyl acetate (800 mL) and the organic layer was washed with water (3×600 mL). The organic layer was separated, dried (MgSO$_4$), filtered, and evaporated to afford 2-tert-butyl-1-ethyl-2,5-dihydro-pyrazolo[3,4-c]quinolin-4-one (20.4 g) as a brown solid. A portion of this solid (15.2 g) was transferred to a round-bottomed flask and concentrated hydrochloric acid (410 mL) was added. The reaction was heated to 120° C. for 1 hour and then stirred at ambient temperature overnight. The solids in the reaction mixture were separated by filtration and washed with water. The solids were transferred to a round-bottomed flask and stirred in diethyl ether (100 mL) for 15 minutes. The product was isolated by filtration to afford 1-ethyl-2,5-dihydro-pyrazolo[3,4-c]quinolin-4-one as the hydrochloride salt. The product was stirred in 2N sodium hydroxide (60 mL) for 1.5 hours, filtered, washed with diethyl ether (600 mL), and dried under reduced pressure to afford 1-ethyl-2,5-dihydro-pyrazolo[3,4-c]quinolin-4-one as a tan brown solid (4.23 g).

Part B

A test tube was charged sequentially with copper iodide (4 mg, 0.2 eq), L-proline (5 mg, 0.4 eq), a reagent (1.5 eq) from the table below, potassium carbonate (55 mg, 4 eq), and a solution of 1-ethyl-2,5-dihydro-pyrazolo[3,4-c]quinolin-4-one (21 mg, 0.10 mmol, 1.0 eq) in dimethylsulfoxide (2 mL). The reaction mixture was purged with nitrogen and then heated at 100° C. overnight. The reaction mixture was filtered and the filtrate was concentrated by vacuum centrifugation. The compounds were purified using the method described in Examples 30-36. The table below shows the reagent used for each example, the structure of the resulting compound, and the observed accurate mass for the isolated trifluoroacetate salt.

| Example | Reagent | R | Measured Mass (M + H) |
|---|---|---|---|
| 134 | 3-Iodopyridine | (3-pyridyl) | 291.1258 |
| 135 | 4-Iodo-1-methyl-1H-imidazole | (1-methyl-1H-imidazol-4-yl) | 294.1359 |
| 136 | 5-Iodo-1-methyl-1H-imidazole | (1-methyl-1H-imidazol-5-yl) | 294.1360 |

-continued

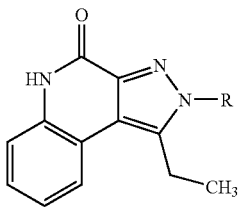

| Example | Reagent | R | Measured Mass (M + H) |
|---|---|---|---|
| 137 | 2-Bromothiazole | | 297.0840 |
| 138 | 2-Bromo-4-methylpyridine | | 305.1397 |
| 139 | 2-Acetyl-5-bromothiophene | | 338.0988 |
| 140 | Ethyl 3-iodobenzoate | | 362.1527 |

Examples 141-152

Part A

A mixture of (4-oxo-2-phenyl-4,5-dihydro-2H-pyrazolo[3,4-c]quinolin-1-yl)acetic acid (1.50 g, 4.70 mmol), N-Boc piperazine (0.96 g, 5.17 mmol), N-(3-dimethylaminopropyl)-N'-ethylcarbodiimide hydrochloride (1.35 g, 7.05 mmol), 1-hydroxybenzotriazole (0.95 g, 7.05 mmol) and 20 mL of DMF was stirred at ambient temperature overnight. The mixture was concentrated under reduced pressure. The residue was triturated with acetonitrile, isolated by filtration, and dried to afford 1.96 g of tert-butyl 4-[(4-oxo-2-phenyl-4,5-dihydro-2H-pyrazolo[3,4-c]quinolin-1-yl)acetyl]piperazine-1-carboxylate as a pale yellow solid.

Part B

A mixture of tert-butyl 4-[(4-oxo-2-phenyl-4,5-dihydro-2H-pyrazolo[3,4-c]quinolin-1-yl)acetyl]piperazine-1-carboxylate, 4 mL of 6 N aqueous hydrochloric acid, and 12 mL of ethanol was heated at 60° C. for 5 hours. The mixture was allowed to cool to ambient temperature and was concentrated under reduced pressure. The residue was triturated with acetonitrile, isolated by filtration, and dried to afford 1.60 g of 1-(2-oxo-2-piperazin-1-ylethyl)-2-phenyl-2,5-dihydro-4H-pyrazolo[3,4-c]quinolin-4-one; hydrochloride as a white solid.

Part C

A solution of 1-(2-oxo-2-piperazin-1-ylethyl)-2,5-dihydro-2-phenyl-4H-pyrazolo[3,4-c]quinolin-4-one dihydrochloride (45 mg, 0.10 mmol, 1.0 eq) and N,N-diisopropylethylamine (34 μL, 2 eq) in methanol (1 mL) was added to a test tube containing an aldehyde (1.25 eq) from the table below. The reaction mixture was stirred for 15 minutes. Borane-pyridine complex (16 μL, 1.3 eq) was added and the reaction mixture was stirred overnight. The reaction was quenched with water (100 μL). The solvent was removed by vacuum centrifugation. The compounds were purified as described in Examples 30-36. The table below shows the aldehyde used for each example, the structure of the resulting compound, and the observed accurate mass for the isolated trifluoroacetate salt.

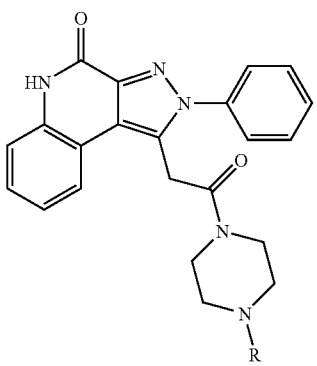

| Example | Reagent | R | Measured Mass (M + H) |
|---|---|---|---|
| 141 | None | | 388.1764 |
| 142 | Cyclopropane-carboxaldehyde | | 442.2240 |
| 143 | Isobutyraldehyde | | 444.2392 |
| 144 | Butyraldehyde | | 444.2365 |
| 145 | Trimethylacetaldehyde | | 458.2568 |

97

-continued

| Example | Reagent | R | Measured Mass (M + H) |
|---------|---------|---|------------------------|
| 146 | Benzaldehyde | | 478.2248 |
| 147 | Nicotinaldehyde | | 479.2180 |
| 148 | Picolinaldehyde | | 479.2172 |
| 149 | 1-Methyl-2-imidazolecarboxaldehyde | | 482.2318 |
| 150 | Cyclohexane-carboxaldehyde | | 484.2701 |

98

-continued

| Example | Reagent | R | Measured Mass (M + H) |
|---------|---------|---|------------------------|
| 151 | 5-Norbornene-2-carboxaldehyde | | 494.2545 |
| 152 | 3-Methoxybenzaldehyde | | 508.2367 |

Examples 153-163

Part A (2-Ethyl-4-oxo-4,5-dihydro-2H-pyrazolo[3,4-c]quinolin-1-yl)acetic acid was prepared according to the general method of Example 19 using ethyl (2-ethyl-4-oxo-4,5-dihydro-2H-pyrazolo[3,4-c]quinolin-1-yl)acetate in lieu of ethyl (4-oxo-2-phenyl-4,5-dihydro-2H-pyrazolo[3,4-c]quinolin-1-yl)acetate.

Part B (2-Ethyl-4-oxo-4,5-dihydro-2H-pyrazolo[3,4-c]quinolin-1-yl)acetic acid was then converted to 2-ethyl-1-(2-oxo-2-piperazin-1-ylethyl)-2,5-dihydro-4H-pyrazolo[3,4-c]quinolin-4-one hydrochloride according to the general method of Parts A and B of Examples 141-152.

Part C

The examples in the table below were prepared and purified according to the general method of Examples 37-43 using 2-ethyl-1-(2-oxo-2-piperazin-1-ylethyl)-2,5-dihydro-4H-pyrazolo[3,4-c]quinolin-4-one dihydrochloride in lieu of 2-phenyl-1-(2-piperidin-4-ylethyl)-2,5-dihydro-4H-pyrazolo[3,4-c]quinolin-4-one and 5 equivalents of N,N-diisopropylethylamine instead of 2 equivalents. The table below shows the reagent used for each example, the structure of the resulting compound, and the observed accurate mass for the isolated trifluoroacetate salt.

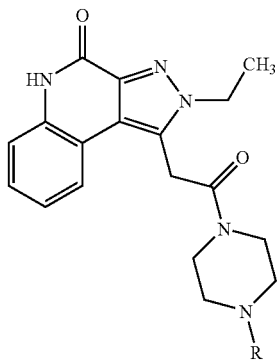
| Example | Reagent | R | Measured Mass (M + H) |
|---|---|---|---|
| 153 | Acetyl chloride | (acetyl) | 382.1859 |
| 154 | Isonicotinoyl chloride hydrochloride | (isonicotinoyl) | 445.1991 |
| 155 | Methanesulfonyl chloride | (methanesulfonyl) | 418.1535 |
| 156 | 1-Methylimidazole-4-sulfonyl chloride | (1-methylimidazole-4-sulfonyl) | 484.1754 |
| 157 | 3-Pyridinesulfonyl chloride hydrochloride | (3-pyridinesulfonyl) | 481.1660 |
| 158 | Methyl isocyanate | (methylcarbamoyl) | 397.1961 |

-continued

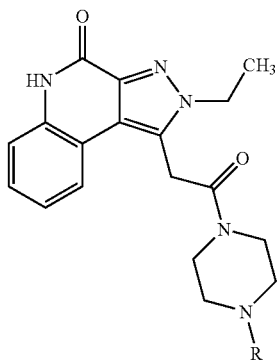

| Example | Reagent | R | Measured Mass (M + H) |
|---|---|---|---|
| 159 | Isopropyl isocyanate | ![HN-C(=O)-CH(CH3)2 acetyl group] | 425.2316 |
| 160 | Phenyl isocyanate | ![HN-C(=O)-Ph acetyl group] | 459.2136 |
| 161 | 1-Piperidinecarbonyl chloride | ![piperidine-C(=O)- acetyl] | 451.2434 |
| 162 | 4-Morpholinylcarbonyl chloride | ![morpholine-C(=O)- acetyl] | 453.2244 |
| 163 | 4-Methyl-1-piperazinecarbonyl chloride | ![N-methylpiperazine-C(=O)- acetyl] | 466.2554 |

Examples 164-176

The examples in the table below were prepared and purified according to the general method of Examples 37-43 using 1-(2-oxo-2-piperazin-1-ylethyl)-2,5-dihydro-2-phenyl-4H-pyrazolo[3,4-c]quinolin-4-one dihydrochloride in lieu of 2-phenyl-1-(2-piperidin-4-ylethyl)-2,5-dihydro-4H-pyrazolo[3,4-c]quinolin-4-one and 5 equivalents of N,N-diisopropylethylamine instead of 2 equivalents. The table below shows the reagent used for each example, the structure of the resulting compound, and the observed accurate mass for the isolated trifluoroacetate salt.

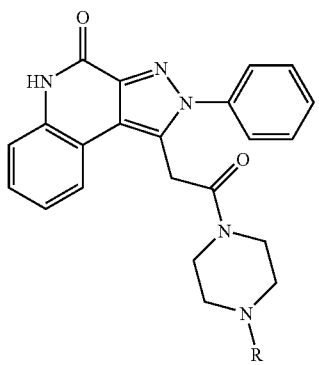

| Example | Reagent | R | Measured Mass (M + H) |
|---|---|---|---|
| 164 | Methyl chloroformate | —C(=O)OCH₃ | 446.1791 |
| 165 | Cyclopropanecarbonyl chloride | —C(=O)-cyclopropyl | 456.2038 |
| 166 | Isobutyryl chloride | —C(=O)CH(CH₃)₂ | 458.2212 |
| 167 | Nicotinoyl chloride hydrochloride | —C(=O)-(3-pyridyl) | 493.1971 |
| 168 | Methanesulfonyl chloride | —S(=O)₂CH₃ | 466.1559 |
| 169 | Isopropylsulfonyl chloride | —S(=O)₂CH(CH₃)₂ | 494.1854 |
| 170 | Dimethylsulfamoyl chloride | —S(=O)₂N(CH₃)₂ | 495.1813 |
| 171 | 1-Methylimidazole-4-sulfonyl chloride | —S(=O)₂-(1-methylimidazol-4-yl) | 532.1763 |

-continued

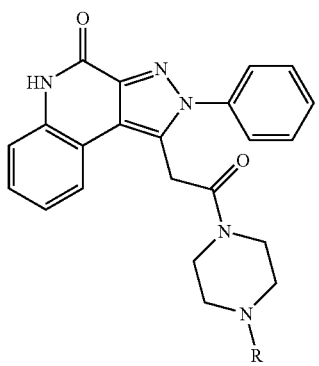

| Example | Reagent | R | Measured Mass (M + H) |
|---|---|---|---|
| 172 | 3-Pyridine sulfonyl chloride hydrochloride | (3-pyridyl sulfonyl group) | 529.1634 |
| 173 | Isopropyl isocyanate | (isopropyl carbamoyl group) | 473.2292 |
| 174 | Cyclopentyl isocyanate | (cyclopentyl carbamoyl group) | 499.2485 |
| 175 | 1-Piperidinecarbonyl chloride | (piperidinyl carbonyl group) | 499.2461 |
| 176 | 4-Morpholinylcarbonyl chloride | (morpholinyl carbonyl group) | 501.2255 |

Examples 177-187

A solution of 4-chloro-1-methyl-2-phenyl-2H-pyrazolo[3,4-c]quinoline (29 mg, 0.10 mmol) in 1-methyl-2-pyrrolidinone (250 μL) was added to a vial containing an amine (2 eq) from the table below. The vial was heated in a microwave to 160° C. over a period of 5 minutes, heating at 160° C. was continued for an additional 5 minutes, and then the vial was allowed to cool. The reaction mixture was diluted with methanol (275 μL). The solvent was removed by vacuum centrifugation. The compounds were purified as described in Examples 30-36. The table below shows the amine used for each example, the structure of the resulting compound, and the observed accurate mass for the isolated trifluoroacetate salt.

| Example | Reagent | R | Measured Mass (M + H) |
|---|---|---|---|
| 177 | Pyrrolidine | pyrrolidinyl | 329.1755 |
| 178 | N-Butylamine | CH₃(CH₂)₃NH– | 331.1956 |
| 179 | Cyclopentylamine | cyclopentyl-NH– | 343.1902 |
| 180 | Piperidine | piperidinyl | 343.1889 |
| 181 | Morpholine | morpholinyl | 345.1692 |
| 182 | Cyclohexylamine | cyclohexyl-NH– | 357.2047 |
| 183 | 1-Methylpiperazine | 4-methylpiperazin-1-yl | 358.2006 |
| 184 | Benzylamine | PhCH₂NH– | 365.1740 |
| 185 | 2-(Aminomethyl)pyridine | (pyridin-2-yl)CH₂NH– | 366.1692 |
| 186 | 3-Picolylamine | (pyridin-3-yl)CH₂NH– | 366.1698 |
| 187 | 4-Picolylamine | (pyridin-4-yl)CH₂NH– | 366.1706 |

Compounds of the invention have been found to modulate cytokine biosynthesis by inhibiting production of tumor necrosis factor α (TNF-α) when tested using the method described below.

Cytokine Inhibition in Human Cells

An in vitro human blood cell system is used to assess cytokine inhibition. Activity is based on the measurement of tumor necrosis factor (α) and interleukin-10 (TNF-α and IL-10) secreted into culture medium by peripheral blood mononuclear cells (PBMC) upon stimulation with bacterial lipopolysaccharide (LPS).

Blood Cell Preparation for Culture

Whole blood from healthy human volunteers is collected and peripheral blood mononuclear cells (PBMCs) are separated. PBMCs are separated from whole blood by density gradient centrifugation using Ficoll-Paque Plus (Amersham Biosciences Piscataway, N.J.). Whole blood is placed in Accuspin (Sigma) or LeucoSep (Greiner Bio-One, Inc., Longwood, Fla.) centrifuge frit tubes containing density gradient medium. The PBMC layer is collected and washed twice with DPBS or HBSS and re-suspended at $2.5 \times 10^6$ cells/mL in RPMI complete. The PBMC suspension is added to 96-well flat bottom sterile tissue culture plates.

Compound Preparation

The compounds are solubilized in dimethyl sulfoxide (DMSO). The compounds are generally tested at concentrations ranging from 10 μM-0.005 μM. Controls include cell samples with DMSO only (no compound or LPS), cell samples stimulated with LPS (Fluorescein isothiocyanate-lipopolysaccharide from *Escherichia coli* 0111:B4; Sigma,), cell samples with reference compounds 4-chloro-2-phenyl-1-(2-piperidin-4-ylethyl)-1H-imidazo[4,5-c]quinoline fumarate hydrate (Izumi, et al., "1H-Imidazo[4,5-c]quinoline Derivatives as Novel Potent TNF-α Suppressors: Synthesis and Structure-Activity Relationship of 1-, 2-, and 4-Substituted 1H-Imidazo[4,5-c]quinolines or 1H-Imidazo[4,5-c]pyridines", *Bioorganic & Medicinal Chemistry*, 11 (2003), 2541-2550) at 10 μM, 2-phenyl-1-(2-piperidin-4-ylethyl)-2,5-dihydropyrazolo[3,4-c]quinolin-4-one at the tested concentration range, and 4-chloro-2-phenyl-1-(2-piperidin-4-ylethyl)-2,5-dihydropyrazolo[3,4-c]quinoline at the tested concentration range. The solution of test compound is added at 1.0 mM to the first well of a 384 well dosing plate and serial 3 fold dilutions are made for the 7 subsequent concentrations in 10% DMSO (diluted in water). Each compound is in quadruplicate on each 384 well dosing plate in an 8-point dose response.

Incubation

80 μL of the PBMC suspension is added to each well on a 384 well sterile tissue culture treated plate. Each compound solution (0.9 μl) is transferred from the dosing plate and is added to the 384 well plate containing PBMCs. After 20 minutes, LPS (0.01 μg/mL final concentration) is added. Final compound concentrations are 10 μM-0.005 μM and the DMSO concentration is 0.1%. The plates are covered with sterile plastic lids and incubated for 18 to 20 hours at 37° C. in a 5% carbon dioxide atmosphere.

Tumor Necrosis Factor (α) and Interleukin-10 Analysis

MSD Multi-Spot® plates contain within each well capture antibodies for human TNF-α and human IL-10 that have been pre-coated on specific spots. Each well contains four spots: one human TNF-α capture antibody (MSD) spot, one human IL-10 capture antibody (MSD) spot, and two inactive bovine serum albumin spots. The human TNF-α and IL-10 capture and detection antibody pairs are from MesoScale Discovery. Standards consist of recombinant human TNF-α (MSD) and recombinant human IL-10 (MSD). Samples and separate standards are added at the time of analysis to each MSD plate. The cytokine-specific detection antibodies are labeled with the SULFO-TAG reagent (MSD) and the cytokine standards are added to the wells of the MSD plates. Supernatants from each tissue culture plate are transferred to the MSD plates and incubated for 4 hours at ambient temperature on a shaker, wells are washed with PBS, and MSD Read buffer is added to each well. Electrochemoluminescent levels are read using MSD's SECTOR HTS READER. Results are expressed in pg/mL upon calculation with known cytokine standards on each plate.

The complete disclosures of the patents, patent documents, and publications cited herein are incorporated by reference in their entirety as if each were individually incorporated. The present invention has been described with reference to several embodiments thereof. The foregoing illustrative embodiments and examples have been provided for clarity of understanding only, and no unnecessary limitations are to be understood therefrom. It will be apparent to those skilled in the art that many changes can be made to the described embodiments without departing from the spirit and scope of the invention. Thus, the scope of the invention is intended to be limited only by the claims that follow.

What is claimed is:
1. A compound of the Formula III:

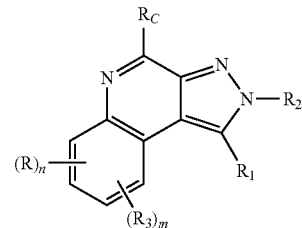

wherein:
$R_C$ is selected from the group consisting of hydrogen, alkyl, alkoxy, phenyl, phenyloxy, heteroaryl, heteroaryloxy, halogen, haloalkyl, hydroxy, cyano, mercapto, nitro, carboxy, alkylamino, dialkylamino, benzylamino, heteroarylmethylamino, and cyclic amino; wherein phenyl, phenoxy, heteroaryl, heteroaryloxy, the phenyl ring of the benzyl group, and heteroaryl in the heteroarylmethylamino group are unsubstituted or substituted by one or more substituents independently selected from the group consisting of methyl, methoxy, bromo, chloro, fluoro, trifluoromethyl, trifluoromethoxy, cyano, nitro, and hydroxy;

R is selected from the group consisting of halogen, hydroxy, alkyl, alkenyl, haloalkyl, alkoxy, alkylthio, and —N(R$_9$)$_2$;

n is an integer from 0 to 4;

$R_1$ is selected from the group consisting of:
—R$_4$,
—X—R$_4$,
—X—Y—X—Y—R$_4$, and
—X—R$_5$;

$R_2$ is selected from the group consisting of hydrogen, halogen, hydroxy, —N(R$_9$), nitro, alkyl, aryl, and heteroaryl wherein the alkyl, aryl, or heteroaryl group is unsubstituted or substituted by one or more substituents independently selected from the group consisting of alkyl, alkoxy, alkylthio, aryl, halogen, haloalkyl, haloalkoxy, cyano, nitro, amino, hydroxy, hydroxyalkyl, hydroxyalkoxy, acetyloxy, and alkoxycarbonylalkoxy;

$R_3$ is selected from the group consisting of:
—Z—R$_4$,
—Z—X—R$_4$,
—Z—X—Y—R$_4$,
—Z—X—Y—X—Y—R4, and
—Z—X—R$_5$;

m is 0 or 1, with the proviso that when m is 1 then n is 0 or 1;

X is selected from the group consisting of alkylene, alkenylene, alkynylene, arylene, heteroarylene, and heterocyclylene wherein the alkylene, alkenylene, and alkynylene groups can be optionally interrupted or terminated by arylene, heteroarylene or heterocyclylene and optionally interrupted by one or more —O— groups;

Y is selected from the group consisting of:

—O—, —S(O)$_{0-2}$—, —S(O)$_2$—N(R$_8$)—,

—C(R$_6$)—, —C(R$_6$)—O—, —O—C(R$_6$)—,

—O—C(O)—O—, —N(R$_8$)—Q—,

—C(R$_6$)—N(R$_8$)—, —O—C(R$_6$)—N(R$_8$)—,

—C(R$_6$)—N(OR$_9$)—, —O—N(R$_8$)—Q—,

—O—N=C(R$_4$)—, —C(=N—O—R$_8$)—,

—C(=N—O—R$_8$)—NH—,

—CH(—N(—O—R$_8$)—Q—R$_4$)—,

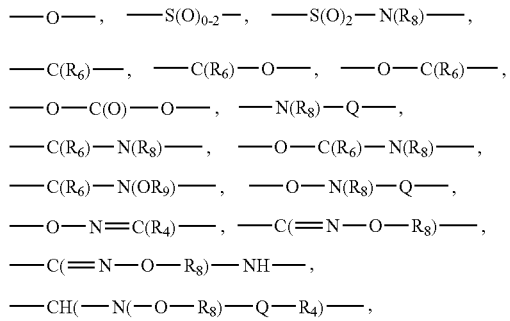

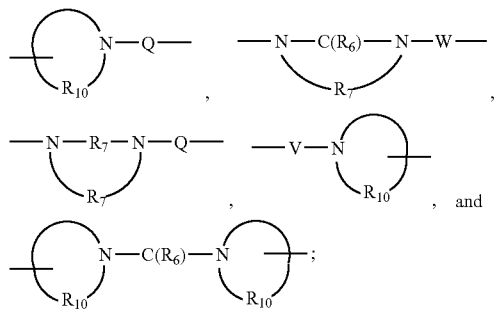

Z is a bond or —O—;

R$_4$ is selected from the group consisting of hydrogen, alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl wherein the alkyl, alkenyl, alkynyl, aryl, arylalkylenyl, aryloxyalkylenyl, alkylarylenyl, heteroaryl, heteroarylalkylenyl, heteroaryloxyalkylenyl, alkylheteroarylenyl, and heterocyclyl groups can be unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of alkyl, alkenyl, alkynyl, and heterocyclyl, oxo, and in the case of heterocyclyl, amidino and oximido;

R$_5$ is selected from the group consisting of:

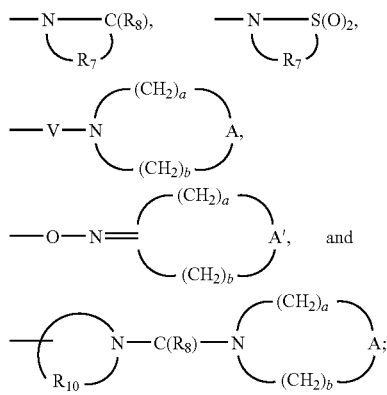

R$_6$ is selected from the group consisting of =O and =S;
R$_7$ is C$_{2-7}$ alkylene;
R$_8$ is selected from the group consisting of hydrogen, alkyl, alkoxyalkylenyl, hydroxyalkylenyl, arylalkylenyl, and heteroarylalkylenyl;
R$_9$ is selected from the group consisting of hydrogen and alkyl;

R$_{10}$ is C$_{3-8}$ alkylene;
A is selected from the group consisting of —O—, —C(O)—, —S(O)$_{0-2}$—, and —N(R$_4$)—;
A' is selected from the group consisting of —O—, —S(O)$_{0-2}$—, —N(-Q-R$_4$)—, and —CH$_2$—;
Q is selected from the group consisting of a bond, —C(R$_6$)—, —C(R$_6$)—C(R$_6$)—, —S(O)$_2$—, —C(R$_6$)—N(R$_8$)—W—, —S(O)$_2$—N(R$_8$)—, —C(R$_8$)—O—, —C(R$_6$)—S—, and —C(R$_6$)—N(OR$_9$)—;
V is selected from the group consisting of —C(R$_6$)—, —O—C(R$_6$)—, —N(R$_8$)—C(R$_6$)—, and —S(O)$_2$—;
W is selected from the group consisting of a bond, —C(O)—, and —S(O)$_2$—; and
a and b are independently integers from 1 to 6 with the proviso that a+b is ≦7;

with the proviso that R$_1$ is other than hydrogen, methyl, or phenyl; and with the further proviso that the compound is other than N-[1,1-dimethyl-2-(2-methyl-2H-pyrazolo[3,4-c]quinolin-1-yl)ethyl]benzamide;
or a pharmaceutically acceptable salt thereof.

2. The compound or salt of claim 1 wherein n is 0.
3. The compound or salt of claim 1 wherein m is 1 and n is 0.
4. The compound or salt of claim 3 wherein m is 0.
5. The compound or salt of claim 1 wherein R$_C$ is selected from the group consisting of hydroxy, halogen, alkyl, haloalkyl, phenyl, phenoxy, heteroaryl, and cyclic amino; wherein phenyl, phenoxy, and heteroaryl are unsubstituted or substituted by one or more substituents independently selected from the group consisting of methyl, methoxy, bromo, chloro, fluoro, trifluoromethyl, trifluoromethoxy, cyano, nitro, and hydroxy.
6. The compound or salt of claim 1 wherein R$_2$ is selected from the group consisting of hydrogen, alkyl, aryl, and heteroaryl, wherein aryl and heteroaryl are unsubstituted or substituted by one or more substituents independently selected from the group consisting of alkyl, alkoxy, alkylthio, aryl, halogen, haloalkyl, haloalkoxy, cyano, nitro, amino, hydroxy, hydroxyalkyl, hydroxyalkoxy, acetyloxy, and alkoxycarbonylalkoxy.
7. The compound or salt of claim 1 wherein R$_1$ is —X—R$_4$.
8. The compound or salt of claim 1 wherein R$_1$ is —X—Y—R$_4$.
9. The compound or salt of any claim 1 wherein R$_1$ is —X—R$_5$.
10. A pharmaceutical composition comprising a therapeutically effective amount of a compound or salt of claim 1 in combination with a pharmaceutically acceptable carrier.
11. The compound or salt of claim 5 wherein R$_c$ is selected from the group consisting of hydroxy, chloro, methyl, trifluoromethyl, phenyl, phenoxy, 1-morpholino, 1-piperidino, 4-methylpiperazin-1-yl, and heteroaryl wherein heteroaryl is a 5 or 6 membered monocyclic ring containing one or two heteroatoms.
12. The compound or salt of claim 6 wherein R$_2$ is C$_{1-4}$ alkyl.
13. The compound or salt of claim 6 wherein R$_2$ is phenyl which is unsubstituted or substituted by one or more substituents independently selected from the group consisting of alkyl, alkoxy, alkylthio, aryl, halogen, haloalkyl, haloalkoxy, cyano, nitro, amino, hydroxy, hydroxyalkyl, hydroxyalkoxy, acetyloxy, and alkoxycarbonylalkoxy.
14. The compound or salt of claim 7 wherein X is —(CH$_2$)$_{1-3}$—, and R$_4$ is aryl, heteroaryl, or heterocyclyl, each of which is unsubstituted or substituted by one or more substituents independently selected from the group consisting of alkyl, alkoxy, hydroxyalkyl, haloalkyl, haloalkoxy, halogen, nitro, hydroxy, mercapto, cyano, aryl, aryloxy, arylalkyleneoxy, heteroaryl, heteroaryloxy, heteroarylalkyleneoxy, heterocyclyl, amino, alkylamino, dialkylamino, (dialkylamino)alkyleneoxy, and in the case of heterocyclyl, oxo, amidino, and oximido.

15. The compound or salt of claim 14 wherein $R_4$ is a saturated, nitrogen-containing heterocyclyl group which is unsubstituted or substituted by oxo, amidino, or oximido.

16. The compound or salt of claim 1 wherein $R_1$ is —X—Y—X—Y—$R_4$.

17. The compound or salt of claim 16 wherein $R_1$ is

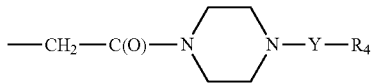

wherein Y is —C(O)—, —S(O)$_2$—, —S(O)$_2$—N($R_8$)—, or —C(O)—N($R_8$)—, and $R_4$ is $C_{1-5}$ alkyl, phenyl, or pyridyl.

18. The compound or salt of claim 9 wherein —X— is —(CH$_2$)$_{1-4}$—, and $R_5$ is

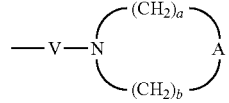

wherein V is —C(O)—, A is —N($R_4$)—, and a and b are both 2.

* * * * *